US007612190B2

(12) United States Patent
Ito et al.

(10) Patent No.: US 7,612,190 B2
(45) Date of Patent: Nov. 3, 2009

(54) METHOD FOR TARGETING A POLYPEPTIDE ONTO CELLULAR SURFACE

(75) Inventors: Makoto Ito, Fukuoka (JP); Motohiro Tani, Fukuoka (JP); Hiroshi Ilda, Fukuoka (JP)

(73) Assignee: Takara Bio Inc., Otsu-shi (JP)

( * ) Notice: Subject to any disclaimer, the term of this patent is extended or adjusted under 35 U.S.C. 154(b) by 0 days.

(21) Appl. No.: 11/882,303

(22) Filed: Jul. 31, 2007

(65) Prior Publication Data

US 2008/0063630 A1 Mar. 13, 2008

Related U.S. Application Data

(62) Division of application No. 10/434,269, filed on May 9, 2003, now Pat. No. 7,326,530.

(30) Foreign Application Priority Data

Jun. 13, 2002 (JP) ............................ 2002-173469

(51) Int. Cl.
*C12Q 1/68* (2006.01)
*C07H 21/04* (2006.01)
*C12N 15/00* (2006.01)

(52) U.S. Cl. ....................... 536/23.1; 435/6; 435/320.1; 435/69.1; 435/69.7; 435/325; 435/252.3; 530/300; 530/350

(58) Field of Classification Search ................ 536/23.1; 435/320.1, 252.3, 325, 69.1, 69.7, 7.1, 6; 530/350, 300
See application file for complete search history.

(56) References Cited

U.S. PATENT DOCUMENTS

| | | | | |
|---|---|---|---|---|
| 2003/0190617 | A1* | 10/2003 | Raymond et al. | 435/6 |
| 2004/0241651 | A1* | 12/2004 | Olek et al. | 435/6 |

FOREIGN PATENT DOCUMENTS

WO WO-2005/056804 A1 6/2005

OTHER PUBLICATIONS

Mitsutake et al. J. Biol. Chem. 276, 26249-26259 (2001).*

T. A. Slimane et al.; Experimental Cell Research, vol. 258, pp. 184-194 (2000).

Nadine Bruneau et al.; The Journal of Biological Chemistry; vol. 272, No. 43, pp. 27353-27361, Oct. 24, 1997.

Laure Monlauzeur et al.; The Journal of Biological Chemistry; vol. 273, No. 46, pp. 30263-30270, Nov. 13, 1998.

Ralf Jacob et al.; The Journal of Biological Chemistry; vol. 275, No. 9, pp. 6566-6572, Mar. 3, 2000.

Motohiro Tani et al.; The Journal of Biological Chemistry; vol. 275, No. 15, pp. 11229-11234, Apr. 14, 2000.

Susumu Mitsutake et al.; The Journal of Biological Chemistry; vol. 276, No. 28, pp. 26249- 26259, Jul. 13, 2001.

Xinglong Zheng et al.; The Journal of Biological Chemistry; vol. 277, No. 9, pp. 6858-6863, Mar. 1, 2002.

Motohiro Tani et al.; The Journal of Biological Chemistry; vol. 278, No. 12, pp. 10523-10530, Mar. 21, 2003.

Charles Yeaman et al.; The Journal of Cell Biology, vol. 139, No. 4, pp. 929-940, Nov. 17, 1997.

Scott Rogers et al.; Science, vol. 234, pp. 364-368, 1986.

Proceedings of the Japanese Conference on the Biochemistry of Lipids, vol. 44, pp. 147-150, 2002, Tokyo. (English translation).

M. Ito, Molecular evolution of endo-glycol ceramidase and ceramidase, Presentation made at the Symposium held on Apr. 27, 2002 in Japan, including partial English translation.

* cited by examiner

*Primary Examiner*—Chih-Min Kam
(74) *Attorney, Agent, or Firm*—Birch, Stewart, Kolasch & Birch, LLP

(57) ABSTRACT

The present invention relates to a polypeptide having an activity for targeting a heterogeneous polypeptide to a surface of cytoplasmic membrane, a nucleic acid encoding the polypeptide, a construct for introducing into a cell, comprising the nucleic acid, a transformant harboring a carrier for introducing into a cell, a method for localizing a polypeptide on a cell surface, a method for detecting the polypeptide or nucleic acid and a kit therefor, and a method for detecting a ligand or receptor for the polypeptide.

11 Claims, 13 Drawing Sheets

SEQUENCE LISTING

<160> NUMBER OF SEQ ID NOS: 27

<210> SEQ ID NO 1
<211> LENGTH: 108
<212> TYPE: DNA
<213> ORGANISM: Rattus norvegicus
<220> FEATURE:
<221> NAME/KEY: CDS
<222> LOCATION: (1)..(108)

<400> SEQUENCE: 1 gat tca ggg aat cac tgg gtt tca acc acc cag ggc ccc aca acc acc 48
Asp Ser Gly Asn His Trp Val Ser Thr Thr Gln Gly Pro Thr Thr Thr
1 5 10 15 cag tcc tct cca acc aca caa act cca acc aca caa act cca gac ctc 96
Gln Ser Ser Pro Thr Thr Gln Thr Pro Thr Thr Gln Thr Pro Asp Leu
20 25 30 cct ccc tct cag 108
Pro Pro Ser Gln
35

<210> SEQ ID NO 2
<211> LENGTH: 36
<212> TYPE: PRT
<213> ORGANISM: Rattus norvegicus

<400> SEQUENCE: 2

Asp Ser Gly Asn His Trp Val Ser Thr Thr Gln Gly Pro Thr Thr Thr
1 5 10 15

Gln Ser Ser Pro Thr Thr Gln Thr Pro Thr Thr Gln Thr Pro Asp Leu
20 25 30

Pro Pro Ser Gln
35

<210> SEQ ID NO 3
<211> LENGTH: 756
<212> TYPE: PRT
<213> ORGANISM: Mouse

<400> SEQUENCE: 3

Met Ala Lys Arg Thr Phe Ser Thr Leu Glu Ala Phe Leu Ile Phe Leu
1 5 10 15

Leu Val Ile Met Thr Val Ile Thr Val Ala Leu Leu Thr Leu Leu Phe
20 25 30

Val Thr Ser Gly Thr Ile Glu Asn His Lys Asp Ser Gly Asn His Trp
35 40 45

Phe Ser Thr Thr Leu Gly Ser Thr Thr Thr Gln Pro Pro Pro Ile Thr
50 55 60

Gln Thr Pro Asn Phe Pro Ser Phe Arg Asn Phe Ser Gly Tyr Tyr Ile
65 70 75 80

Gly Val Gly Arg Ala Asp Cys Thr Gly Gln Val Ser Asp Ile Asn Leu
85 90 95

Met Gly Tyr Gly Lys Asn Gly Gln Asn Ala Arg Gly Leu Leu Thr Arg
100 105 110

Leu Phe Ser Arg Ala Phe Ile Leu Ala Asp Pro Asp Gly Ser Asn Arg
115 120 125

Met Ala Phe Val Ser Val Glu Leu Cys Met Ile Ser Gln Arg Leu Arg
130 135 140

-continued

```
Leu Glu Val Leu Lys Arg Leu Glu Ser Lys Tyr Gly Ser Leu Tyr Arg
145                 150                 155                 160

Arg Asp Asn Val Ile Leu Ser Ala Ile His Thr His Ser Gly Pro Ala
                165                 170                 175

Gly Phe Phe Gln Tyr Thr Leu Tyr Ile Leu Ala Ser Glu Gly Phe Ser
            180                 185                 190

Asn Arg Thr Phe Gln Tyr Ile Val Ser Gly Ile Met Lys Ser Ile Asp
        195                 200                 205

Ile Ala His Thr Asn Leu Lys Pro Gly Lys Ile Phe Ile Asn Lys Gly
    210                 215                 220

Asn Val Ala Asn Val Gln Ile Asn Arg Ser Pro Ser Ser Tyr Leu Leu
225                 230                 235                 240

Asn Pro Gln Ser Glu Arg Ala Arg Tyr Ser Ser Asn Thr Asp Lys Glu
                245                 250                 255

Met Leu Val Leu Lys Leu Val Asp Leu Asn Gly Glu Asp Leu Gly Leu
            260                 265                 270

Ile Ser Trp Phe Ala Ile His Pro Val Ser Met Asn Asn Ser Asn His
        275                 280                 285

Phe Val Asn Ser Asp Asn Met Gly Tyr Ala Ala Tyr Leu Phe Glu Gln
    290                 295                 300

Glu Lys Asn Lys Gly Tyr Leu Pro Gly Gln Gly Pro Phe Val Ala Gly
305                 310                 315                 320

Phe Ala Ser Ser Asn Leu Gly Asp Val Ser Pro Asn Ile Leu Gly Pro
                325                 330                 335

His Cys Val Asn Thr Gly Glu Ser Cys Asp Asn Asp Lys Ser Thr Cys
            340                 345                 350

Pro Asn Gly Gly Pro Ser Met Cys Met Ala Ser Gly Pro Gly Gln Asp
        355                 360                 365

Met Phe Glu Ser Thr His Ile Ile Gly Arg Ile Ile Tyr Gln Lys Ala
    370                 375                 380

Lys Glu Leu Tyr Ala Ser Ala Ser Gln Glu Val Thr Gly Pro Val Leu
385                 390                 395                 400

Ala Ala His Gln Trp Val Asn Met Thr Asp Val Ser Val Gln Leu Asn
                405                 410                 415

Ala Thr His Thr Val Lys Thr Cys Lys Pro Ala Leu Gly Tyr Ser Phe
            420                 425                 430

Ala Ala Gly Thr Ile Asp Gly Val Ser Gly Leu Asn Ile Thr Gln Gly
        435                 440                 445

Thr Thr Glu Gly Asp Pro Phe Trp Asp Thr Leu Arg Asp Gln Leu Leu
    450                 455                 460

Gly Lys Pro Ser Glu Glu Ile Val Glu Cys Gln Lys Pro Lys Pro Ile
465                 470                 475                 480

Leu Leu His Ser Gly Glu Leu Thr Ile Pro His Pro Trp Gln Pro Asp
                485                 490                 495

Ile Val Asp Val Gln Ile Val Thr Val Gly Ser Leu Ala Ile Ala Ala
            500                 505                 510

Ile Pro Gly Glu Leu Thr Thr Met Ser Gly Arg Arg Phe Arg Glu Ala
        515                 520                 525

Ile Lys Lys Glu Phe Ala Leu Tyr Gly Met Lys Asp Met Thr Val Val
    530                 535                 540

Ile Ala Gly Leu Ser Asn Val Tyr Thr His Tyr Ile Thr Thr Tyr Glu
545                 550                 555                 560

Glu Tyr Gln Ala Gln Arg Tyr Glu Ala Ala Ser Thr Ile Tyr Gly Pro
```

-continued

```
                565                 570                 575

His Thr Leu Ser Ala Tyr Ile Gln Leu Phe Arg Asp Leu Ala Lys Ala
            580                 585                 590

Ile Ala Thr Asp Thr Val Ala Asn Met Ser Ser Gly Pro Glu Pro Pro
        595                 600                 605

Phe Phe Lys Asn Leu Ile Ala Ser Leu Ile Pro Asn Ile Ala Asp Arg
    610                 615                 620

Ala Pro Ile Gly Lys His Phe Gly Asp Val Leu Gln Pro Ala Lys Pro
625                 630                 635                 640

Glu Tyr Arg Val Gly Glu Val Val Glu Val Ile Phe Val Gly Ala Asn
                645                 650                 655

Pro Lys Asn Ser Ala Glu Asn Gln Thr His Gln Thr Phe Leu Thr Val
            660                 665                 670

Glu Lys Tyr Glu Asp Ser Val Ala Asp Trp Gln Ile Met Tyr Asn Asp
        675                 680                 685

Ala Ser Trp Glu Thr Arg Phe Tyr Trp His Lys Gly Ile Leu Gly Leu
    690                 695                 700

Ser Asn Ala Thr Ile Tyr Trp His Ile Pro Asp Thr Ala Tyr Pro Gly
705                 710                 715                 720

Ile Tyr Arg Ile Arg Tyr Phe Gly His Asn Arg Lys Gln Glu Leu Leu
                725                 730                 735

Lys Pro Ala Val Ile Leu Ala Phe Glu Gly Ile Ser Ser Pro Phe Glu
            740                 745                 750

Val Val Thr Thr
        755


<210> SEQ ID NO 4
<211> LENGTH: 2456
<212> TYPE: DNA
<213> ORGANISM: Rattus norvegicus
<220> FEATURE:
<221> NAME/KEY: CDS
<222> LOCATION: (70)..(2355)

<400> SEQUENCE: 4

caggattctg catggccatt tggactcccg ggaggtgagg acttgctttg attcacagag      60

tcaggagaa atg gca aag cga acc ttc tcc tcc ttg gag gcg ttc ctc att     111
          Met Ala Lys Arg Thr Phe Ser Ser Leu Glu Ala Phe Leu Ile
            1               5                  10

ttc ctt ctg gta atg atg acg gcc atc aca gtg gcc ctt ctc acc ctc      159
Phe Leu Leu Val Met Met Thr Ala Ile Thr Val Ala Leu Leu Thr Leu
 15                  20                  25                  30

ttg ttc gtc acc agt ggg acc atc gaa aac cac aaa gat tca ggg aat      207
Leu Phe Val Thr Ser Gly Thr Ile Glu Asn His Lys Asp Ser Gly Asn
                 35                  40                  45

cac tgg gtt tca acc acc cag ggc ccc aca acc acc cag tcc tct cca      255
His Trp Val Ser Thr Thr Gln Gly Pro Thr Thr Thr Gln Ser Ser Pro
             50                  55                  60

acc aca caa act cca acc aca caa act cca gac ctc cct ccc tct cag      303
Thr Thr Gln Thr Pro Thr Thr Gln Thr Pro Asp Leu Pro Pro Ser Gln
         65                  70                  75

aac ttc agt ggc tac tac att ggt gtt ggg cga gct gac tgc acc gga      351
Asn Phe Ser Gly Tyr Tyr Ile Gly Val Gly Arg Ala Asp Cys Thr Gly
     80                  85                  90

caa gtg tca gat atc aat ttg atg ggc tat ggc aaa aat ggc cag aac      399
Gln Val Ser Asp Ile Asn Leu Met Gly Tyr Gly Lys Asn Gly Gln Asn
 95                 100                 105                 110
```

-continued

```
gca cag ggt ctc ctc acc agg ctg ttc agc cgc gct ttt atc ttg gcg      447
Ala Gln Gly Leu Leu Thr Arg Leu Phe Ser Arg Ala Phe Ile Leu Ala
                115                 120                 125

gat cca gat ggg tca aat cga atg gca ttt gtg agc gtg gaa cta tgc      495
Asp Pro Asp Gly Ser Asn Arg Met Ala Phe Val Ser Val Glu Leu Cys
            130                 135                 140

atg att tcc caa cga ctc agg ttg gag gtc ttg aag aga cta cag agt      543
Met Ile Ser Gln Arg Leu Arg Leu Glu Val Leu Lys Arg Leu Gln Ser
        145                 150                 155

aaa tat ggc tct ctg tat cga aga gac aac gtt atc ctg agt gcc act      591
Lys Tyr Gly Ser Leu Tyr Arg Arg Asp Asn Val Ile Leu Ser Ala Thr
    160                 165                 170

cac act cac tct ggc cca gca gga ttt ttc caa tat aca ctc tat ata      639
His Thr His Ser Gly Pro Ala Gly Phe Phe Gln Tyr Thr Leu Tyr Ile
175                 180                 185                 190

ctt gcc agc gag gga ttc agc aac cgg acc ttt cag tac ata gtc tct      687
Leu Ala Ser Glu Gly Phe Ser Asn Arg Thr Phe Gln Tyr Ile Val Ser
                195                 200                 205

ggg atc gtg aag agc att gat ata gca cac aca aat ctt aaa ccg ggc      735
Gly Ile Val Lys Ser Ile Asp Ile Ala His Thr Asn Leu Lys Pro Gly
            210                 215                 220

aaa gtc ctt atc aac aaa gga aat gtt gct aat gtg cag atc aac cgc      783
Lys Val Leu Ile Asn Lys Gly Asn Val Ala Asn Val Gln Ile Asn Arg
        225                 230                 235

agt ccc tcc tct tac ctt cag aat cca cct tcg gag aga gca agg tat      831
Ser Pro Ser Ser Tyr Leu Gln Asn Pro Pro Ser Glu Arg Ala Arg Tyr
    240                 245                 250

tct tcc gac acg gac aag gaa atg gtc gtc ttg aaa ctg gtg gat ttg      879
Ser Ser Asp Thr Asp Lys Glu Met Val Val Leu Lys Leu Val Asp Leu
255                 260                 265                 270

aat gga gaa gac ttg ggc ctt atc agc tgg ttt gcc gtc cac ccc gtg      927
Asn Gly Glu Asp Leu Gly Leu Ile Ser Trp Phe Ala Val His Pro Val
                275                 280                 285

agc atg aac aac agt aac cac ctc gtc aac agt gac aat atg ggc tac      975
Ser Met Asn Asn Ser Asn His Leu Val Asn Ser Asp Asn Met Gly Tyr
            290                 295                 300

gcg gct tac ctt ttc gag caa gaa aag aac aga ggc tat ctg cct gga     1023
Ala Ala Tyr Leu Phe Glu Gln Glu Lys Asn Arg Gly Tyr Leu Pro Gly
        305                 310                 315

cag gga cca ttc gta gca ggc ttt gct tca tca aat ctc gga gac gtg     1071
Gln Gly Pro Phe Val Ala Gly Phe Ala Ser Ser Asn Leu Gly Asp Val
    320                 325                 330

tcg ccc aac att ctt ggc cca cat tgt gtc aac aca ggg gag tct tgt     1119
Ser Pro Asn Ile Leu Gly Pro His Cys Val Asn Thr Gly Glu Ser Cys
335                 340                 345                 350

gac aac gac aaa agc acc tgt ccc agt ggt ggg cct agc atg tgc atg     1167
Asp Asn Asp Lys Ser Thr Cys Pro Ser Gly Gly Pro Ser Met Cys Met
                355                 360                 365

gcc agt gga ccc gga caa gat atg ttt gag agc aca cac att ata gga     1215
Ala Ser Gly Pro Gly Gln Asp Met Phe Glu Ser Thr His Ile Ile Gly
            370                 375                 380

cgg gtc atc tat cag aaa gcc aag gag ctg cat gcc tct gcc tcc cag     1263
Arg Val Ile Tyr Gln Lys Ala Lys Glu Leu His Ala Ser Ala Ser Gln
        385                 390                 395

gaa gtg acc ggc cca gtg ctc aca gct cac cag tgg gtg aac atg acg     1311
Glu Val Thr Gly Pro Val Leu Thr Ala His Gln Trp Val Asn Met Thr
    400                 405                 410

gat gtg agc gtc caa ctc aat gcc aca cac aca gtg aag acg tgt aaa     1359
Asp Val Ser Val Gln Leu Asn Ala Thr His Thr Val Lys Thr Cys Lys
415                 420                 425                 430
```

-continued

```
gcc gcc ctg ggc tac agt ttt gcc gca ggc aca att gat gga gtt tcg      1407
Ala Ala Leu Gly Tyr Ser Phe Ala Ala Gly Thr Ile Asp Gly Val Ser
                435                 440                 445

ggc ctc aat att aca cag gga aca aca gaa ggg aat cta ttt tgg gac      1455
Gly Leu Asn Ile Thr Gln Gly Thr Thr Glu Gly Asn Leu Phe Trp Asp
            450                 455                 460

act ctt cgg gac cag ctc ttg gga aaa cca tct gaa gaa atc ata gaa      1503
Thr Leu Arg Asp Gln Leu Leu Gly Lys Pro Ser Glu Glu Ile Ile Glu
        465                 470                 475

tgc cag aaa cct aaa cca atc cta atc cac acg gga gag ctg aca aaa      1551
Cys Gln Lys Pro Lys Pro Ile Leu Ile His Thr Gly Glu Leu Thr Lys
    480                 485                 490

cct cat cct tgg caa cca gat att gtt gat att cag atc gtt act ctt      1599
Pro His Pro Trp Gln Pro Asp Ile Val Asp Ile Gln Ile Val Thr Leu
495                 500                 505                 510

ggt tcg ttg gcc ata gct gct atc cct ggg gaa ttt aca acc atg tca      1647
Gly Ser Leu Ala Ile Ala Ala Ile Pro Gly Glu Phe Thr Thr Met Ser
                515                 520                 525

ggt cga aga ctt cgt gag gca gtt aaa aaa gaa ttt gca ctt tat ggg      1695
Gly Arg Arg Leu Arg Glu Ala Val Lys Lys Glu Phe Ala Leu Tyr Gly
            530                 535                 540

atg aag gat atg act gtc gtt atc gca ggg ctg agc aat gtt tat acc      1743
Met Lys Asp Met Thr Val Val Ile Ala Gly Leu Ser Asn Val Tyr Thr
        545                 550                 555

cat tac att acc aca tat gaa gaa tac cag gct cag cgg tat gag gca      1791
His Tyr Ile Thr Thr Tyr Glu Glu Tyr Gln Ala Gln Arg Tyr Glu Ala
    560                 565                 570

gca tct acg att tat gga cca cac acc ctg tct gcg tac atc cag ctc      1839
Ala Ser Thr Ile Tyr Gly Pro His Thr Leu Ser Ala Tyr Ile Gln Leu
575                 580                 585                 590

ttc aga gcc ctt gct aag gcc att gct acg gat aca gta gcc aac atg      1887
Phe Arg Ala Leu Ala Lys Ala Ile Ala Thr Asp Thr Val Ala Asn Met
                595                 600                 605

agc agc ggt cct gag cct cca ttc ttc aaa aac ctg ata ggt tca ctt      1935
Ser Ser Gly Pro Glu Pro Pro Phe Phe Lys Asn Leu Ile Gly Ser Leu
            610                 615                 620

att cct aat att gcg gat aga gca cca ata ggc aaa caa ttt ggg gat      1983
Ile Pro Asn Ile Ala Asp Arg Ala Pro Ile Gly Lys Gln Phe Gly Asp
        625                 630                 635

gtc ctg cag cca gca aaa cct gaa tac aga gtg gga gaa gtg gtt gaa      2031
Val Leu Gln Pro Ala Lys Pro Glu Tyr Arg Val Gly Glu Val Val Glu
    640                 645                 650

gtt gtc ttt gta ggc gct aac cca aag aat tca gca gaa aac cag acc      2079
Val Val Phe Val Gly Ala Asn Pro Lys Asn Ser Ala Glu Asn Gln Thr
655                 660                 665                 670

cat caa acc ttc ctc act gtg gag aaa tac gag gac tct gta gcc aac      2127
His Gln Thr Phe Leu Thr Val Glu Lys Tyr Glu Asp Ser Val Ala Asn
                675                 680                 685

tgg cag ata atg cat aac gat gcc tcc tgg gag acg aga ttt tat tgg      2175
Trp Gln Ile Met His Asn Asp Ala Ser Trp Glu Thr Arg Phe Tyr Trp
            690                 695                 700

cac aag gga gta ctg ggt ctg agc aat gca aca ata cat tgg cat att      2223
His Lys Gly Val Leu Gly Leu Ser Asn Ala Thr Ile His Trp His Ile
        705                 710                 715

cca gat act gcc ctc cct gga gtc tac aga atc aga tat ttt gga cac      2271
Pro Asp Thr Ala Leu Pro Gly Val Tyr Arg Ile Arg Tyr Phe Gly His
    720                 725                 730

aat cgg aag cag gaa ctt cta aag cct gct gtc ata cta gca ttt gaa      2319
Asn Arg Lys Gln Glu Leu Leu Lys Pro Ala Val Ile Leu Ala Phe Glu
```

-continued

```
735                 740                 745                 750

gga att tct tcc cct ttt gaa att gtc act act tag tgaaaagttg          2365
Gly Ile Ser Ser Pro Phe Glu Ile Val Thr Thr
                755                 760

acagatcttg aagaacagct tttctctgtg cacattatag agtgatttca cacaaatgtg   2425

aactaccagt ttaaaaaaaa aaaaaaaaaa a                                  2456


<210> SEQ ID NO 5
<211> LENGTH: 761
<212> TYPE: PRT
<213> ORGANISM: Rattus norvegicus

<400> SEQUENCE: 5

Met Ala Lys Arg Thr Phe Ser Ser Leu Glu Ala Phe Leu Ile Phe Leu
  1               5                  10                  15

Leu Val Met Met Thr Ala Ile Thr Val Ala Leu Leu Thr Leu Leu Phe
             20                  25                  30

Val Thr Ser Gly Thr Ile Glu Asn His Lys Asp Ser Gly Asn His Trp
         35                  40                  45

Val Ser Thr Thr Gln Gly Pro Thr Thr Thr Gln Ser Ser Pro Thr Thr
     50                  55                  60

Gln Thr Pro Thr Thr Gln Thr Pro Asp Leu Pro Pro Ser Gln Asn Phe
 65                  70                  75                  80

Ser Gly Tyr Tyr Ile Gly Val Gly Arg Ala Asp Cys Thr Gly Gln Val
                 85                  90                  95

Ser Asp Ile Asn Leu Met Gly Tyr Gly Lys Asn Gly Gln Asn Ala Gln
            100                 105                 110

Gly Leu Leu Thr Arg Leu Phe Ser Arg Ala Phe Ile Leu Ala Asp Pro
        115                 120                 125

Asp Gly Ser Asn Arg Met Ala Phe Val Ser Val Glu Leu Cys Met Ile
    130                 135                 140

Ser Gln Arg Leu Arg Leu Glu Val Leu Lys Arg Leu Gln Ser Lys Tyr
145                 150                 155                 160

Gly Ser Leu Tyr Arg Arg Asp Asn Val Ile Leu Ser Ala Thr His Thr
                165                 170                 175

His Ser Gly Pro Ala Gly Phe Phe Gln Tyr Thr Leu Tyr Ile Leu Ala
            180                 185                 190

Ser Glu Gly Phe Ser Asn Arg Thr Phe Gln Tyr Ile Val Ser Gly Ile
        195                 200                 205

Val Lys Ser Ile Asp Ile Ala His Thr Asn Leu Lys Pro Gly Lys Val
    210                 215                 220

Leu Ile Asn Lys Gly Asn Val Ala Asn Val Gln Ile Asn Arg Ser Pro
225                 230                 235                 240

Ser Ser Tyr Leu Gln Asn Pro Pro Ser Glu Arg Ala Arg Tyr Ser Ser
                245                 250                 255

Asp Thr Asp Lys Glu Met Val Val Leu Lys Leu Val Asp Leu Asn Gly
            260                 265                 270

Glu Asp Leu Gly Leu Ile Ser Trp Phe Ala Val His Pro Val Ser Met
        275                 280                 285

Asn Asn Ser Asn His Leu Val Asn Ser Asp Asn Met Gly Tyr Ala Ala
    290                 295                 300

Tyr Leu Phe Glu Gln Glu Lys Asn Arg Gly Tyr Leu Pro Gly Gln Gly
305                 310                 315                 320

Pro Phe Val Ala Gly Phe Ala Ser Ser Asn Leu Gly Asp Val Ser Pro
```

-continued

```
                325                 330                 335

Asn Ile Leu Gly Pro His Cys Val Asn Thr Gly Glu Ser Cys Asp Asn
            340                 345                 350

Asp Lys Ser Thr Cys Pro Ser Gly Gly Pro Ser Met Cys Met Ala Ser
        355                 360                 365

Gly Pro Gly Gln Asp Met Phe Glu Ser Thr His Ile Ile Gly Arg Val
    370                 375                 380

Ile Tyr Gln Lys Ala Lys Glu Leu His Ala Ser Ala Ser Gln Glu Val
385                 390                 395                 400

Thr Gly Pro Val Leu Thr Ala His Gln Trp Val Asn Met Thr Asp Val
                405                 410                 415

Ser Val Gln Leu Asn Ala Thr His Thr Val Lys Thr Cys Lys Ala Ala
            420                 425                 430

Leu Gly Tyr Ser Phe Ala Ala Gly Thr Ile Asp Gly Val Ser Gly Leu
        435                 440                 445

Asn Ile Thr Gln Gly Thr Thr Glu Gly Asn Leu Phe Trp Asp Thr Leu
    450                 455                 460

Arg Asp Gln Leu Leu Gly Lys Pro Ser Glu Glu Ile Ile Glu Cys Gln
465                 470                 475                 480

Lys Pro Lys Pro Ile Leu Ile His Thr Gly Glu Leu Thr Lys Pro His
                485                 490                 495

Pro Trp Gln Pro Asp Ile Val Asp Ile Gln Ile Val Thr Leu Gly Ser
            500                 505                 510

Leu Ala Ile Ala Ala Ile Pro Gly Glu Phe Thr Thr Met Ser Gly Arg
        515                 520                 525

Arg Leu Arg Glu Ala Val Lys Lys Glu Phe Ala Leu Tyr Gly Met Lys
    530                 535                 540

Asp Met Thr Val Val Ile Ala Gly Leu Ser Asn Val Tyr Thr His Tyr
545                 550                 555                 560

Ile Thr Thr Tyr Glu Glu Tyr Gln Ala Gln Arg Tyr Glu Ala Ala Ser
                565                 570                 575

Thr Ile Tyr Gly Pro His Thr Leu Ser Ala Tyr Ile Gln Leu Phe Arg
            580                 585                 590

Ala Leu Ala Lys Ala Ile Ala Thr Asp Thr Val Ala Asn Met Ser Ser
        595                 600                 605

Gly Pro Glu Pro Pro Phe Phe Lys Asn Leu Ile Gly Ser Leu Ile Pro
    610                 615                 620

Asn Ile Ala Asp Arg Ala Pro Ile Gly Lys Gln Phe Gly Asp Val Leu
625                 630                 635                 640

Gln Pro Ala Lys Pro Glu Tyr Arg Val Gly Glu Val Val Glu Val Val
                645                 650                 655

Phe Val Gly Ala Asn Pro Lys Asn Ser Ala Glu Asn Gln Thr His Gln
            660                 665                 670

Thr Phe Leu Thr Val Glu Lys Tyr Glu Asp Ser Val Ala Asn Trp Gln
        675                 680                 685

Ile Met His Asn Asp Ala Ser Trp Glu Thr Arg Phe Tyr Trp His Lys
    690                 695                 700

Gly Val Leu Gly Leu Ser Asn Ala Thr Ile His Trp His Ile Pro Asp
705                 710                 715                 720

Thr Ala Leu Pro Gly Val Tyr Arg Ile Arg Tyr Phe Gly His Asn Arg
                725                 730                 735

Lys Gln Glu Leu Leu Lys Pro Ala Val Ile Leu Ala Phe Glu Gly Ile
            740                 745                 750
```

-continued

Ser Ser Pro Phe Glu Ile Val Thr Thr
755 760

<210> SEQ ID NO 6
<211> LENGTH: 714
<212> TYPE: PRT
<213> ORGANISM: Dictyostelium discoideum

<400> SEQUENCE: 6

Met Lys Arg Ser Ile Val Phe Ile Tyr Ser Leu Val Ile Leu Leu Leu
1 5 10 15

Ser Val Gly Phe Ile Asp Ala Phe Lys Ile Ser Ile Glu Asn His Ile
20 25 30

Lys Leu Ser Asp Asp Ser Ser Tyr Gln Ile Gly Thr Gly Ile Tyr Asp
35 40 45

Ile Thr Gly Pro Gly Ala Glu Thr Asn Met Met Gly Tyr Ala Met Pro
50 55 60

Gly Gln Ile Thr Gly Gly Ile His Phe Arg Gln Arg Ala Arg Ala Phe
65 70 75 80

Val Phe Ile Asp Ser Glu Gly Asn Arg Ala Val Tyr Val Ser Thr Asp
85 90 95

Ser Cys Met Ile Phe Gln Glu Val Lys Ile Gln Val Ile Gln Asp Leu
100 105 110

Gln Glu Ile Phe Gly Pro Thr Leu Tyr Thr His Asp Asn Val Leu Leu
115 120 125

Ser Gly Thr His Thr His Ser Gly Pro Ala Gly Phe Ser Glu Tyr Ala
130 135 140

Leu Tyr Gly Ile Thr Ala Leu Gly Phe Tyr Lys Lys Asn Phe Asp Thr
145 150 155 160

Ile Cys Asp Gly Ile Val Gln Ala Ile Val Lys Ala His Lys Ser Val
165 170 175

Gln Pro Ala Arg Met Leu Thr Gln Gln Gly Glu Leu Trp Asn Ser Asn
180 185 190

Ile Asn Arg Ser Pro Tyr Ala Tyr Asp Asn Asn Pro Glu Glu Glu Lys
195 200 205

Ala Met Tyr Asp Ala Asn Val Asp Lys Asn Met Thr Val Ile Arg Ile
210 215 220

Glu Asp Met Ser Gly Asn Pro Phe Ala Ala Ile Ser Phe Phe Gly Val
225 230 235 240

His Cys Thr Ser Met Asn Asn Thr Asn His Leu Ile Ser Gly Asp Asn
245 250 255

Lys Gly Tyr Ala Ser Tyr Leu Trp Glu Lys His Ala Asn Gly Gln Ser
260 265 270

Ser Leu Pro Gly Thr Gly Pro Phe Ile Ala Ala Phe Gly Gln Ser Asn
275 280 285

Glu Gly Asp Val Ser Pro Asn Thr Arg Gly Pro Thr Cys Arg Asp Gly
290 295 300

Lys Pro Cys Asp Tyr Lys Thr Ser Thr Cys Asn Gly Lys Val Glu Glu
305 310 315 320

Cys Trp Ala Leu Gly Pro Gly Thr Asp Gly Asp Met Phe Glu Ser Thr
325 330 335

Gln Ile Ile Gly Gly Asn Gln Phe Asn Lys Ala Leu Glu Leu Phe Asn
340 345 350

-continued

Asn Ala Thr Ile Gln Val Ser Gly Lys Ile Gln Tyr Arg His Thr Trp
355 360 365

Lys Pro Phe Thr Asn Val Ser Val Glu Ala Pro Tyr Asn Ser Gly Val
370 375 380

Glu Gly Ala Thr Thr Cys Arg Gly Ala Met Gly Tyr Ser Phe Ala Gly
385 390 395 400

Gly Thr Thr Asp Gly Pro Gly Ala Phe Asn Phe Ile Gln Gly Asp Asn
405 410 415

Ser Thr Thr Asn Pro Phe Trp Asn Phe Ile Gly Gly Ile Ile Ala Lys
420 425 430

Pro Thr Pro Gln Gln Thr Ala Cys Gln Ala Pro Lys Pro Ile Leu Ile
435 440 445

Asp Val Gly Met Val Glu Pro Ile Pro Trp Val Pro Asp Val Met Pro
450 455 460

Leu Gln Ile Ile Thr Leu Gly Gln Ile Val Leu Val Ala Val Pro Gly
465 470 475 480

Glu Phe Thr Thr Met Ser Gly Arg Arg Leu Arg Asn Thr Val Arg Glu
485 490 495

Ile Ile Gly Gln Ser Ile Glu Asn Pro Ile Val Leu Ile Ala Gly Leu
500 505 510

Ala Asn Thr Tyr Ser Gly Tyr Ile Ala Thr Phe Glu Glu Phe Gln Val
515 520 525

Gln Arg Tyr Glu Gly Ala Ser Thr Val Phe Gly Pro His Thr Leu Gly
530 535 540

Ala Tyr Gln Gln Glu Phe Ala Asn Leu Ala Gln Ser Ile Val Asp Gly
545 550 555 560

Ser Gln Ala Asp Pro Gly Thr Phe Pro Arg Asn Met Ser Gly His Thr
565 570 575

Pro Phe Phe Leu Pro Pro Val Ile Val Asp Val Ala Pro Lys Phe Asp
580 585 590

Asp Phe Gly Asp Ile Tyr Thr Asp Val Ser Thr Thr Thr Pro Tyr Ser
595 600 605

Ile Asn Gln Thr Val Thr Val Ile Phe Tyr Gly Ala Asn Leu Arg Asn
610 615 620

Asn Phe Met Thr Glu Ser Ser Phe Leu Thr Val Asp Gln Leu Gln Ser
625 630 635 640

Asn Gly Gln Trp Thr Thr Ile Leu Asn Asp Gly Asp Trp Asp Thr Lys
645 650 655

Leu Tyr Trp Lys Met His Asp Leu Gly Phe Ser Leu Ile Thr Val Asp
660 665 670

Trp Thr Ile Ser Pro Ile Thr Gln Pro Gly Thr Tyr Arg Ile Thr His
675 680 685

Ser Gly Tyr Ala Lys Lys Asn Pro Phe Ser Asp Asn Leu Thr Phe Tyr
690 695 700

Gln Gly Ile Ser Ser Asn Phe Asn Val Gln
705 710

<210> SEQ ID NO 7
<211> LENGTH: 670
<212> TYPE: PRT
<213> ORGANISM: Pseudomonas aeruginosa

<400> SEQUENCE: 7

Met Ser Arg Ser Ala Phe Thr Ala Leu Leu Leu Ser Cys Val Leu Leu
1 5 10 15

-continued

```
Ala Leu Ser Met Pro Ala Arg Ala Asp Asp Leu Pro Tyr Arg Phe Gly
                20                  25                  30

Leu Gly Lys Ala Asp Ile Thr Gly Glu Ala Ala Glu Val Gly Met Met
            35                  40                  45

Gly Tyr Ser Ser Leu Glu Gln Lys Thr Ala Gly Ile His Met Arg Gln
        50                  55                  60

Trp Ala Arg Ala Phe Val Ile Glu Glu Ala Ala Ser Gly Arg Arg Leu
65                  70                  75                  80

Val Tyr Val Asn Thr Asp Leu Gly Met Thr Phe Gln Ala Val His Leu
                85                  90                  95

Lys Val Leu Ala Arg Leu Lys Ala Lys Tyr Pro Gly Val Tyr Asp Glu
            100                 105                 110

Asn Asn Val Met Leu Ala Ala Thr His Thr His Ser Gly Pro Gly Gly
        115                 120                 125

Phe Ser His Tyr Ala Met Tyr Asn Leu Ser Val Leu Gly Phe Gln Glu
    130                 135                 140

Lys Thr Phe Asn Ala Ile Val Asp Gly Ile Val Arg Ser Ile Glu Arg
145                 150                 155                 160

Ala Gln Ala Arg Leu Gln Pro Gly Arg Leu Phe Tyr Gly Ser Gly Glu
                165                 170                 175

Leu Arg Asn Ala Ser Arg Asn Arg Ser Leu Leu Ser His Leu Lys Asn
            180                 185                 190

Pro Asp Ile Ala Gly Tyr Glu Asp Gly Ile Asp Pro Gln Met Ser Val
        195                 200                 205

Leu Ser Phe Val Asp Ala Asn Gly Glu Leu Ala Gly Ala Ile Ser Trp
    210                 215                 220

Phe Pro Val His Ser Thr Ser Met Thr Asn Ala Asn His Leu Ile Ser
225                 230                 235                 240

Pro Asp Asn Lys Gly Tyr Ala Ser Tyr His Trp Glu His Asp Val Ser
                245                 250                 255

Arg Lys Ser Gly Phe Val Ala Ala Phe Ala Gln Thr Asn Ala Gly Asn
            260                 265                 270

Leu Ser Pro Asn Leu Asn Leu Lys Pro Gly Ser Gly Pro Phe Asp Asn
        275                 280                 285

Glu Phe Asp Asn Thr Arg Glu Ile Gly Leu Arg Gln Phe Ala Lys Ala
    290                 295                 300

Tyr Glu Ile Ala Gly Gln Ala Gln Glu Glu Val Leu Gly Glu Leu Asp
305                 310                 315                 320

Ser Arg Phe Arg Phe Val Asp Phe Thr Arg Leu Pro Ile Arg Pro Glu
                325                 330                 335

Phe Thr Asp Gly Gln Pro Arg Gln Leu Cys Thr Ala Ala Ile Gly Thr
            340                 345                 350

Ser Leu Ala Ala Gly Ser Thr Glu Asp Gly Pro Gly Pro Leu Gly Leu
        355                 360                 365

Glu Glu Gly Asn Asn Pro Phe Leu Ser Ala Leu Gly Gly Leu Leu Thr
    370                 375                 380

Gly Val Pro Pro Gln Glu Leu Val Gln Cys Gln Ala Glu Lys Thr Ile
385                 390                 395                 400

Leu Ala Asp Thr Gly Asn Lys Lys Pro Tyr Pro Trp Thr Pro Thr Val
                405                 410                 415

Leu Pro Ile Gln Met Phe Arg Ile Gly Gln Leu Glu Leu Leu Gly Ala
            420                 425                 430
```

-continued

Pro Ala Glu Phe Thr Val Met Ala Gly Val Arg Ile Arg Arg Ala Val
435 440 445

Gln Ala Ala Ser Glu Ala Ala Gly Ile Arg His Val Val Phe Asn Gly
450 455 460

Tyr Ala Asn Ala Tyr Ala Ser Tyr Val Thr Thr Arg Glu Glu Tyr Ala
465 470 475 480

Ala Gln Glu Tyr Glu Gly Gly Ser Thr Leu Tyr Gly Pro Trp Thr Gln
485 490 495

Ala Ala Tyr Gln Gln Leu Phe Val Asp Met Ala Val Ala Leu Arg Glu
500 505 510

Arg Leu Pro Val Glu Thr Ser Ala Ile Ala Pro Asp Leu Ser Cys Cys
515 520 525

Gln Met Asn Phe Gln Thr Gly Val Val Ala Asp Asp Pro Tyr Ile Gly
530 535 540

Lys Ser Phe Gly Asp Val Leu Gln Gln Pro Arg Glu Ser Tyr Arg Ile
545 550 555 560

Gly Asp Lys Val Thr Val Ala Phe Val Thr Gly His Pro Lys Asn Asp
565 570 575

Leu Arg Thr Glu Lys Thr Phe Leu Glu Val Val Asn Ile Gly Lys Asp
580 585 590

Gly Lys Gln Thr Pro Val Thr Val Ala Thr Asp Asn Asp Trp Asp Thr
595 600 605

Gln Tyr Arg Trp Glu Arg Val Gly Ile Ser Ala Ser Lys Ala Thr Ile
610 615 620

Ser Trp Ser Ile Pro Pro Gly Thr Glu Pro Gly His Tyr Tyr Ile Arg
625 630 635 640

His Tyr Gly Asn Ala Lys Asn Phe Trp Thr Gln Lys Ile Ser Glu Ile
645 650 655

Gly Gly Ser Thr Arg Ser Phe Glu Val Leu Gly Thr Thr Pro
660 665 670

<210> SEQ ID NO 8
<211> LENGTH: 637
<212> TYPE: PRT
<213> ORGANISM: Mycobacterium tuberculosis

<400> SEQUENCE: 8

Met Leu Ser Val Gly Arg Gly Ile Ala Asp Ile Thr Gly Glu Ala Ala
1 5 10 15

Asp Cys Gly Met Leu Gly Tyr Gly Lys Ser Asp Gln Arg Thr Ala Gly
20 25 30

Ile His Gln Arg Leu Arg Ser Arg Ala Phe Val Phe Arg Asp Asp Ser
35 40 45

Gln Asp Gly Asp Ala Arg Leu Leu Leu Ile Val Ala Glu Leu Pro Leu
50 55 60

Pro Met Gln Asn Val Asn Glu Glu Val Leu Arg Arg Leu Ala Asp Leu
65 70 75 80

Tyr Gly Asp Thr Tyr Ser Glu Gln Asn Thr Leu Ile Thr Ala Thr His
85 90 95

Thr His Ala Gly Pro Gly Gly Tyr Cys Gly Tyr Leu Leu Tyr Asn Leu
100 105 110

Thr Thr Ser Gly Phe Arg Pro Ala Thr Phe Ala Ala Ile Val Asp Gly
115 120 125

Ile Val Glu Ser Val Glu His Ala His Ala Asp Val Ala Pro Ala Glu
130 135 140

-continued

```
Val Ser Leu Ser His Gly Glu Leu Tyr Gly Ala Ser Ile Asn Arg Ser
145                 150                 155                 160

Pro Ser Ala Phe Asp Arg Asn Pro Pro Ala Asp Lys Ala Phe Phe Pro
                165                 170                 175

Lys Arg Val Asp Pro His Thr Thr Leu Val Arg Ile Asp Arg Gly Glu
            180                 185                 190

Ala Thr Val Gly Val Ile His Phe Phe Ala Thr His Gly Thr Ser Met
        195                 200                 205

Thr Asn Arg Asn His Leu Ile Ser Gly Asp Asn Lys Gly Phe Ala Ala
    210                 215                 220

Tyr His Trp Glu Arg Thr Val Gly Gly Ala Asp Tyr Leu Ala Gly Gln
225                 230                 235                 240

Pro Asp Phe Ile Ala Ala Phe Ala Gln Thr Asn Pro Gly Asp Met Ser
                245                 250                 255

Pro Asn Val Asp Gly Pro Leu Ser Pro Glu Ala Pro Pro Asp Arg Glu
            260                 265                 270

Phe Asp Asn Thr Arg Arg Thr Gly Leu Cys Gln Phe Glu Asp Ala Phe
        275                 280                 285

Thr Gln Leu Ser Gly Ala Thr Pro Ile Gly Ala Gly Ile Asp Ala Arg
    290                 295                 300

Phe Thr Tyr Val Asp Leu Gly Ser Val Leu Val Arg Gly Glu Tyr Thr
305                 310                 315                 320

Pro Asp Gly Glu Glu Arg Arg Thr Gly Arg Pro Met Phe Gly Ala Gly
                325                 330                 335

Ala Met Ala Gly Thr Asp Glu Gly Pro Gly Phe His Gly Phe Arg Gln
            340                 345                 350

Gly Arg Asn Pro Phe Trp Asp Arg Leu Ser Arg Ala Met Tyr Arg Leu
        355                 360                 365

Ala Arg Pro Thr Ala Ala Ala Gln Ala Pro Lys Gly Ile Val Met Pro
    370                 375                 380

Ala Arg Leu Pro Asn Arg Ile His Pro Phe Val Gln Glu Ile Val Pro
385                 390                 395                 400

Val Gln Leu Val Arg Ile Gly Arg Leu Tyr Leu Ile Gly Ile Pro Gly
                405                 410                 415

Glu Pro Thr Ile Val Ala Gly Leu Arg Leu Arg Arg Met Val Ala Ser
            420                 425                 430

Ile Val Gly Ala Asp Leu Ala Asp Val Leu Cys Val Gly Tyr Thr Asn
        435                 440                 445

Ala Tyr Ile His Tyr Val Thr Thr Pro Glu Glu Tyr Leu Glu Gln Arg
    450                 455                 460

Tyr Glu Gly Gly Ser Thr Leu Phe Gly Arg Trp Glu Leu Cys Ala Leu
465                 470                 475                 480

Met Gln Thr Val Ala Glu Leu Ala Glu Ala Met Arg Asp Gly Arg Pro
                485                 490                 495

Val Thr Leu Gly Arg Arg Pro Arg Pro Thr Arg Glu Leu Ser Trp Val
            500                 505                 510

Arg Gly Ala Pro Ala Asp Ala Gly Ser Phe Gly Ala Val Ile Ala Glu
        515                 520                 525

Pro Ser Ala Thr Tyr Arg Pro Gly Gln Ala Val Glu Ala Val Phe Val
    530                 535                 540

Ser Ala Leu Pro Asn Asn Asp Leu Arg Arg Gly Gly Thr Tyr Leu Glu
545                 550                 555                 560
```

-continued

```
Val Val Arg Arg Glu Gly Ala Ser Trp Val Arg Ile Ala Asp Asp Gly
                565                 570                 575

Asp Trp Ala Thr Ser Phe Arg Trp Gln Arg Gln Gly Arg Ala Gly Ser
            580                 585                 590

His Val Ser Ile Arg Trp Asp Val Pro Gly Asp Thr Thr Pro Gly Gln
        595                 600                 605

Tyr Arg Ile Val His His Gly Thr Ala Arg Asp Arg Asn Gly Met Leu
    610                 615                 620

Thr Ala Phe Ser Ala Thr Thr Arg Glu Phe Thr Val Val
625                 630                 635


<210> SEQ ID NO 9
<211> LENGTH: 704
<212> TYPE: PRT
<213> ORGANISM: Drosophila melanogaster

<400> SEQUENCE: 9

Met Ala Asn Ser Lys Met Ala Phe Leu Ala Phe Leu Ala Val Ser Phe
  1               5                  10                  15

Leu Cys Gly Leu Val Ser Ala Thr Tyr Lys Val Gly Val Gly Arg Ala
             20                  25                  30

Asp Ile Thr Gly Pro Pro Val Glu Ile Asn Phe Met Gly Tyr Ala Asn
         35                  40                  45

Ile Lys Gln Val Gly Arg Gly Ile His Thr Arg Val Phe Ala Arg Ala
     50                  55                  60

Phe Val Val Glu Asp Glu Lys Gly Asn Arg Val Ala Phe Val Ser Ala
 65                  70                  75                  80

Asp Ala Gly Met Met Gly Tyr Gly Leu Lys Arg Glu Val Ile Lys Arg
                 85                  90                  95

Leu Gln Ala Arg Tyr Gly Asn Ile Tyr His Asn Asp Asn Val Ala Ile
            100                 105                 110

Ser Gly Thr His Thr His Gly Ala Pro Gly Gly Phe Leu Met His Leu
        115                 120                 125

Leu Tyr Asp Ile Ser Ile Leu Gly Phe Val Pro Gln Thr Phe Glu Val
    130                 135                 140

Met Ala Gln Gly Leu Tyr Leu Cys Ile Lys Arg Ala Thr Asp Asn Leu
145                 150                 155                 160

Val Asp Gly Arg Ile Leu Leu Ser Lys Thr Thr Val Leu Asn Val Asn
                165                 170                 175

Ile Asn Arg Ser Pro Ser Ser Tyr Leu Arg Asn Pro Ala Glu Glu Arg
            180                 185                 190

Ala Gln Tyr Glu His Asp Thr Asp Lys Thr Leu Thr Gln Leu Arg Phe
        195                 200                 205

Val Asp Leu Glu Asn Asn Leu Leu Gly Ala Phe Asn Trp Tyr Ala Val
    210                 215                 220

His Ala Thr Ser Met Asn Asn Thr Asn Arg Leu Val Thr Ser Asp Asn
225                 230                 235                 240

Val Gly Tyr Ala Ala Leu Leu Leu Glu Lys Glu Tyr Asn Pro Asn Lys
                245                 250                 255

Met Pro Gly Lys Gly Lys Phe Val Gly Ala Phe Cys Ser Ser Asn Leu
            260                 265                 270

Gly Asp Val Ser Pro Asn Ile Met Gly Pro Lys Cys Ser Ile Ser Gly
        275                 280                 285

Asn Glu Cys Asp Leu Leu Thr Ser Arg Cys Pro Thr Gly Glu Gly Asp
    290                 295                 300
```

-continued

```
Cys Phe Ala Ser Gly Pro Gly Lys Asp Met Phe Glu Ser Thr Gln Ile
305                 310                 315                 320

Leu Gly Gln Arg Leu Ala Asp Ala Ala Leu Gly Leu Leu Asn Glu Gln
                325                 330                 335

Ser Gln Glu Ser Thr Ala Arg Glu Val Thr Gly Asp Val Arg Phe Ile
            340                 345                 350

His Gln Phe Val Asp Met Pro Asn Tyr Asn Gly Ser Thr Tyr Asn Pro
        355                 360                 365

Leu Ser Arg Lys Val Asp Lys Ile Arg Gly Cys Gln Pro Ala Met Gly
    370                 375                 380

Tyr Ser Phe Ala Ala Gly Thr Thr Asp Gly Pro Gly Ala Phe Ser Phe
385                 390                 395                 400

Glu Gln Gly Thr Thr Thr Asp Asn Pro Met Trp Asn Phe Val Arg Asp
                405                 410                 415

Phe Ile Ala Ala Pro Thr Gln Glu Asp Ile Lys Cys His Glu Pro Lys
            420                 425                 430

Pro Ile Leu Leu Ala Thr Gly Arg Ala Thr Phe Pro Tyr Glu Trp Gln
        435                 440                 445

Pro Lys Ile Val Ser Asp Gln Leu Leu Lys Ile Gly Asp Val Ile Ile
    450                 455                 460

Ala Ala Val Pro Cys Glu Phe Thr Thr Met Ala Gly Arg Arg Leu Arg
465                 470                 475                 480

Asn Gln Ile Arg Ala Ala Ala Ser Ala Val Gly Gly Ile Asp Thr Glu
                485                 490                 495

Val Ile Ile Ala Gly Leu Thr Asn Ile Tyr Thr Ser Tyr Thr Val Thr
            500                 505                 510

Pro Glu Glu Tyr Gln Ala Gln Arg Tyr Glu Ala Ala Ser Thr Ile Phe
        515                 520                 525

Gly Pro His Thr His Ser Ile Tyr Met Asp Val Phe Glu Arg Leu Thr
    530                 535                 540

Lys Ala Met Met Arg Asn Glu Thr Val Asp Ala Gly Pro Ser Pro Pro
545                 550                 555                 560

Tyr Met Asn Asp Val Met Leu Ser Leu Asn Thr Gly Val Leu Phe Asp
                565                 570                 575

Gly His Pro Ile Asn Thr Asp Phe Gly Tyr Val Lys Ser Gln Pro Asn
            580                 585                 590

Lys Glu Tyr Gly Ile Asn Glu Thr Val Lys Val Thr Tyr Ile Ser Gly
        595                 600                 605

Asn Pro Arg Asn Asn Leu Phe Thr Glu Lys Thr Tyr Phe Thr Ile Glu
    610                 615                 620

Arg Lys Ile Asn Glu Asp Arg Trp Lys Val Ala Tyr Thr Asp Ala Ser
625                 630                 635                 640

Trp Glu Thr Lys Met Val Trp His Arg Thr Asn Thr Ile Leu Gly Phe
                645                 650                 655

Ser Glu Met Asp Ile Tyr Trp Asp Ile Ser Pro Gln Thr Leu Pro Gly
            660                 665                 670

Glu Tyr Arg Ile Arg His Ser Gly Glu Tyr Lys Tyr Ile Leu Gly Gly
        675                 680                 685

Lys Tyr Pro Tyr Glu Gly Leu Thr His Ser Phe Thr Val Lys Glu Asp
    690                 695                 700
```

<210> SEQ ID NO 10
<211> LENGTH: 705

-continued

<212> TYPE: PRT
<213> ORGANISM: Arabidopsis thaliana

<400> SEQUENCE: 10

```
Met Thr Arg Trp Ser Met Ser Met His Cys Thr Leu Phe Leu Leu Phe
  1               5                  10                  15

Leu Leu Arg Leu Thr Cys Ile Phe Ser Asp Ser Asp Tyr Leu Met Gly
             20                  25                  30

Leu Gly Ser Tyr Asp Ile Thr Gly Pro Ala Ala Asp Val Asn Met Met
         35                  40                  45

Gly Tyr Ala Asn Met Glu Gln Val Ala Ser Gly Val His Phe Arg Leu
     50                  55                  60

Arg Ala Arg Ala Phe Ile Val Ala Glu Pro Tyr Lys Glu Asn Val Ala
 65                  70                  75                  80

Ile Ser Gly Thr His Thr His Ala Gly Pro Gly Gly Tyr Leu Gln Tyr
                 85                  90                  95

Ile Leu Tyr Leu Val Thr Ser Leu Gly Phe Val His Gln Ser Phe Asn
            100                 105                 110

Ala Leu Val Asp Gly Ile Glu Gln Ser Ile Ile Gln Ala His Glu Asn
        115                 120                 125

Leu Arg Pro Gly Ser Ile Leu Ile Asn Lys Gly Glu Leu Leu Asp Ala
    130                 135                 140

Gly Val Asn Arg Ser Pro Ser Ala Tyr Leu Asn Asn Pro Ala His Glu
145                 150                 155                 160

Arg Ser Lys Tyr Glu Tyr Asp Val Asp Lys Glu Met Thr Leu Val Lys
                165                 170                 175

Phe Val Asp Asp Gln Trp Gly Pro Val Gly Ser Phe Asn Cys Gly Asp
            180                 185                 190

Asn Lys Gly Thr Ala Ala Arg Ile Met Glu Asp Trp Phe Glu Arg Glu
        195                 200                 205

Asn Gly Cys Arg Ser Val Asp Val Glu Ser Pro Arg Arg Val Ser Ser
    210                 215                 220

Ile Ile Ser Asp Pro Tyr Gly Glu His Gln Asp Leu Met Glu Met Ala
225                 230                 235                 240

Ser Ser Leu Leu Ser Thr Gly Gly Lys Thr Val Thr Arg Met Ser Ser
                245                 250                 255

Val Ala Arg Arg Val Arg Ser Arg Phe Arg His Ala Asp Lys Pro Arg
            260                 265                 270

Phe Val Ser Ala Phe Cys Gln Thr Asn Cys Gly Asp Val Ser Pro Asn
        275                 280                 285

Val Leu Gly Ala Phe Cys Ile Asp Thr Gly Leu Pro Cys Glu Phe Asn
    290                 295                 300

Gln Ser Thr Cys Gly Gly Lys Asn Glu Gln Cys Tyr Gly Arg Gly Pro
305                 310                 315                 320

Gly Tyr Pro Asp Glu Phe Glu Ser Thr Arg Ile Ile Gly Glu Arg Gln
                325                 330                 335

Phe Lys Lys Ala Ala Asp Leu Phe Thr Lys Ala Ser Glu Glu Ile Gln
            340                 345                 350

Gly Lys Val Asp Tyr Arg His Ala Tyr Val Asp Phe Ser Gln Leu Glu
        355                 360                 365

Val Thr Ile Asn Gly Gln Asn Gly Gly Ser Glu Val Val Lys Thr Cys
    370                 375                 380

Pro Ala Ala Met Gly Phe Gly Phe Ala Ala Gly Thr Thr Asp Gly Pro
385                 390                 395                 400
```

-continued

Gly Ala Phe Asp Phe Lys Gln Gly Asp Asp Gln Gly Asn Pro Phe Trp
405 410 415

Arg Leu Val Arg Asn Leu Leu Lys Asn Pro Thr Glu Glu Gln Val Arg
420 425 430

Cys Gln Arg Pro Lys Pro Ile Leu Leu Asp Thr Gly Glu Met Lys Gln
435 440 445

Pro Tyr Asp Trp Ala Ile Leu Arg Ile Gly Gln Leu Val Ile Leu Cys
450 455 460

Val Pro Gly Glu Phe Thr Thr Met Ala Gly Arg Arg Leu Arg Asp Ala
465 470 475 480

Val Lys Thr Val Leu Lys Glu Gly Ser Asn Gly Arg Glu Phe Ser Val
485 490 495

Val Ile Ala Gly Leu Thr Asn Ser Tyr Ser Gln Tyr Ile Ala Thr Phe
500 505 510

Glu Glu Tyr Gln Val Gln Arg Tyr Glu Gly Ala Ser Thr Leu Tyr Gly
515 520 525

Pro His Thr Leu Ser Gly Tyr Ile Gln Glu Phe Lys Lys Leu Ala Asn
530 535 540

Asp Leu Leu Ser Ala Gln Thr Thr Asp Pro Gly Pro Gln Pro Pro Asp
545 550 555 560

Leu Leu His Lys Gln Ile Ser Leu Leu Thr Pro Val Val Ala Asp Met
565 570 575

Thr Pro Ile Gly Thr Ala Phe Gly Asp Val Thr Ser Asp Val Pro Arg
580 585 590

Leu Ser Lys Phe Arg Lys Gly Ala Asp Ile Val Arg Val Gln Phe Arg
595 600 605

Ser Ala Asn Pro Arg Asn Asp Leu Met Thr Glu Gly Thr Phe Ala Leu
610 615 620

Val Glu Arg Trp Leu Glu Gly Arg Glu Thr Trp Val Pro Val Tyr Asp
625 630 635 640

Asp Asp Asp Phe Cys Leu Arg Phe Lys Trp Ser Arg Pro Phe Lys Leu
645 650 655

Ser Thr Gln Ser Thr Ala Thr Ile Glu Trp Arg Ile Pro Glu Thr Ala
660 665 670

Ser Pro Gly Val Tyr Arg Ile Thr His Phe Gly Ser Ala Lys Thr Pro
675 680 685

Ile Ser Ser Ile His His Phe Ser Gly Ser Ser Ser Ala Phe Val Val
690 695 700

Tyr
705

<210> SEQ ID NO 11
<211> LENGTH: 42
<212> TYPE: PRT
<213> ORGANISM: Rattus norvegicus

<400> SEQUENCE: 11

Met Ala Lys Arg Thr Phe Ser Ser Leu Glu Ala Phe Leu Ile Phe Leu
1 5 10 15

Leu Val Met Met Thr Ala Ile Thr Val Ala Leu Leu Thr Leu Leu Phe
20 25 30

Val Thr Ser Gly Thr Ile Glu Asn His Lys
35 40

-continued

<210> SEQ ID NO 12
<211> LENGTH: 683
<212> TYPE: PRT
<213> ORGANISM: Rattus norvegicus

<400> SEQUENCE: 12

```
Asn Phe Ser Gly Tyr Tyr Ile Gly Val Gly Arg Ala Asp Cys Thr Gly
  1               5                  10                  15

Gln Val Ser Asp Ile Asn Leu Met Gly Tyr Gly Lys Asn Gly Gln Asn
             20                  25                  30

Ala Gln Gly Leu Leu Thr Arg Leu Phe Ser Arg Ala Phe Ile Leu Ala
         35                  40                  45

Asp Pro Asp Gly Ser Asn Arg Met Ala Phe Val Ser Val Glu Leu Cys
     50                  55                  60

Met Ile Ser Gln Arg Leu Arg Leu Glu Val Leu Lys Arg Leu Gln Ser
 65                  70                  75                  80

Lys Tyr Gly Ser Leu Tyr Arg Arg Asp Asn Val Ile Leu Ser Ala Thr
                 85                  90                  95

His Thr His Ser Gly Pro Ala Gly Phe Phe Gln Tyr Thr Leu Tyr Ile
            100                 105                 110

Leu Ala Ser Glu Gly Phe Ser Asn Arg Thr Phe Gln Tyr Ile Val Ser
        115                 120                 125

Gly Ile Val Lys Ser Ile Asp Ile Ala His Thr Asn Leu Lys Pro Gly
    130                 135                 140

Lys Val Leu Ile Asn Lys Gly Asn Val Ala Asn Val Gln Ile Asn Arg
145                 150                 155                 160

Ser Pro Ser Ser Tyr Leu Gln Asn Pro Pro Ser Glu Arg Ala Arg Tyr
                165                 170                 175

Ser Ser Asp Thr Asp Lys Glu Met Val Val Leu Lys Leu Val Asp Leu
            180                 185                 190

Asn Gly Glu Asp Leu Gly Leu Ile Ser Trp Phe Ala Val His Pro Val
        195                 200                 205

Ser Met Asn Asn Ser Asn His Leu Val Asn Ser Asp Asn Met Gly Tyr
    210                 215                 220

Ala Ala Tyr Leu Phe Glu Gln Glu Lys Asn Arg Gly Tyr Leu Pro Gly
225                 230                 235                 240

Gln Gly Pro Phe Val Ala Gly Phe Ala Ser Ser Asn Leu Gly Asp Val
                245                 250                 255

Ser Pro Asn Ile Leu Gly Pro His Cys Val Asn Thr Gly Glu Ser Cys
            260                 265                 270

Asp Asn Asp Lys Ser Thr Cys Pro Ser Gly Gly Pro Ser Met Cys Met
        275                 280                 285

Ala Ser Gly Pro Gly Gln Asp Met Phe Glu Ser Thr His Ile Ile Gly
    290                 295                 300

Arg Val Ile Tyr Gln Lys Ala Lys Glu Leu His Ala Ser Ala Ser Gln
305                 310                 315                 320

Glu Val Thr Gly Pro Val Leu Thr Ala His Gln Trp Val Asn Met Thr
                325                 330                 335

Asp Val Ser Val Gln Leu Asn Ala Thr His Thr Val Lys Thr Cys Lys
            340                 345                 350

Ala Ala Leu Gly Tyr Ser Phe Ala Ala Gly Thr Ile Asp Gly Val Ser
        355                 360                 365

Gly Leu Asn Ile Thr Gln Gly Thr Thr Glu Gly Asn Leu Phe Trp Asp
    370                 375                 380
```

-continued

Thr Leu Arg Asp Gln Leu Leu Gly Lys Pro Ser Glu Glu Ile Ile Glu
385 390 395 400

Cys Gln Lys Pro Lys Pro Ile Leu Ile His Thr Gly Glu Leu Thr Lys
405 410 415

Pro His Pro Trp Gln Pro Asp Ile Val Asp Ile Gln Ile Val Thr Leu
420 425 430

Gly Ser Leu Ala Ile Ala Ala Ile Pro Gly Glu Phe Thr Thr Met Ser
435 440 445

Gly Arg Arg Leu Arg Glu Ala Val Lys Lys Glu Phe Ala Leu Tyr Gly
450 455 460

Met Lys Asp Met Thr Val Val Ile Ala Gly Leu Ser Asn Val Tyr Thr
465 470 475 480

His Tyr Ile Thr Thr Tyr Glu Glu Tyr Gln Ala Gln Arg Tyr Glu Ala
485 490 495

Ala Ser Thr Ile Tyr Gly Pro His Thr Leu Ser Ala Tyr Ile Gln Leu
500 505 510

Phe Arg Ala Leu Ala Lys Ala Ile Ala Thr Asp Thr Val Ala Asn Met
515 520 525

Ser Ser Gly Pro Glu Pro Pro Phe Phe Lys Asn Leu Ile Gly Ser Leu
530 535 540

Ile Pro Asn Ile Ala Asp Arg Ala Pro Ile Gly Lys Gln Phe Gly Asp
545 550 555 560

Val Leu Gln Pro Ala Lys Pro Glu Tyr Arg Val Gly Glu Val Val Glu
565 570 575

Val Val Phe Val Gly Ala Asn Pro Lys Asn Ser Ala Glu Asn Gln Thr
580 585 590

His Gln Thr Phe Leu Thr Val Glu Lys Tyr Glu Asp Ser Val Ala Asn
595 600 605

Trp Gln Ile Met His Asn Asp Ala Ser Trp Glu Thr Arg Phe Tyr Trp
610 615 620

His Lys Gly Val Leu Gly Leu Ser Asn Ala Thr Ile His Trp His Ile
625 630 635 640

Pro Asp Thr Ala Leu Pro Gly Val Tyr Arg Ile Arg Tyr Phe Gly His
645 650 655

Asn Arg Lys Gln Glu Leu Leu Lys Pro Ala Val Ile Leu Ala Phe Glu
660 665 670

Gly Ile Ser Ser Pro Phe Glu Ile Val Thr Thr
675 680

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: a sequence for primer

<400> SEQUENCE: 13
agggtaccga aatggcaaag cgaaccttct cc 32

<210> SEQ ID NO 14
<211> LENGTH: 47
<212> TYPE: DNA
<213> ORGANISM: Artificial Sequence
<220> FEATURE:
<223> OTHER INFORMATION: Description of Artificial Sequence: a sequence for primer -continued

<400> SEQUENCE: 14
acaccaatgt agtagccact gaagtttttg tggttttcga tggtccc 47

<210> SEQ ID NO 15
<211> LENGTH: 47
<212> TYPE: DNA
<213> ORGANISM: Artificial Sequence
<220> FEATURE:
<223> OTHER INFORMATION: Description of Artificial Sequence: a sequence for primer

<400> SEQUENCE: 15
gggaccatcg aaaaccacaa aaacttcagt ggctactaca ttggtgt 47

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: a sequence for primer

<400> SEQUENCE: 16
gccgctcgag agtagtgaca atttcaaaag gggaaga 37

<210> SEQ ID NO 17
<211> LENGTH: 78
<212> TYPE: PRT
<213> ORGANISM: Rattus norvegicus

<400> SEQUENCE: 17

Met Ala Lys Arg Thr Phe Ser Ser Leu Glu Ala Phe Leu Ile Phe Leu
1 5 10 15

Leu Val Met Met Thr Ala Ile Thr Val Ala Leu Leu Thr Leu Leu Phe
20 25 30

Val Thr Ser Gly Thr Ile Glu Asn His Lys Asp Ser Gly Asn His Trp
35 40 45

Val Ser Thr Thr Gln Gly Pro Thr Thr Thr Gln Ser Ser Pro Thr Thr
50 55 60

Gln Thr Pro Thr Thr Gln Thr Pro Asp Leu Pro Pro Ser Gln
65 70 75

<210> SEQ ID NO 18
<211> LENGTH: 32
<212> TYPE: DNA
<213> ORGANISM: Artificial Sequence
<220> FEATURE:
<223> OTHER INFORMATION: Description of Artificial Sequence: a sequence for primer

<400> SEQUENCE: 18
agggtaccga aatggcaaag cgaaccttct cc 32

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: a sequence for primer

<400> SEQUENCE: 19
ccacggatcc cctgagaggg agggaggtct gg 32

-continued

<210> SEQ ID NO 20
<211> LENGTH: 32
<212> TYPE: DNA
<213> ORGANISM: Artificial Sequence
<220> FEATURE:
<223> OTHER INFORMATION: Description of Artificial Sequence: a sequence for primer

<400> SEQUENCE: 20
ttccggatcc ctttgtggtt ttcgatggtc cc 32

<210> SEQ ID NO 21
<211> LENGTH: 35
<212> TYPE: PRT
<213> ORGANISM: Rattus norvegicus

<400> SEQUENCE: 21

Ser Pro Thr Pro Thr Ser Asn Ser Thr Pro Thr Ser Thr Pro Thr Ser
1 5 10 15

Thr Ser Thr Pro Thr Ser Thr Ser Thr Pro Ser Pro Gly Lys Cys Pro
20 25 30

Pro Glu Gln
35

<210> SEQ ID NO 22
<211> LENGTH: 30
<212> TYPE: PRT
<213> ORGANISM: Homo sapiens

<400> SEQUENCE: 22

Thr Thr Pro Ser Pro Thr Thr Thr Pro Ser Ser Pro Ile Thr Thr Thr
1 5 10 15

Thr Thr Pro Ser Ser Thr Thr Thr Pro Ser Pro Pro Pro Thr
20 25 30

<210> SEQ ID NO 23
<211> LENGTH: 35
<212> TYPE: PRT
<213> ORGANISM: Insect intestial mucin

<400> SEQUENCE: 23

Thr Thr Thr Thr Gln Ala Pro Thr Thr Thr Gln Ala Pro Thr Thr Thr
1 5 10 15

Gln Ala Pro Thr Thr Thr Gln Ala Pro Thr Thr Thr Thr Gln Ala Pro
20 25 30

Thr Thr Thr
35

<210> SEQ ID NO 24
<211> LENGTH: 32
<212> TYPE: DNA
<213> ORGANISM: Artificial Sequence
<220> FEATURE:
<223> OTHER INFORMATION: Description of Artificial Sequence: a sequence for primer

<400> SEQUENCE: 24
agggtaccga aatggcaaag cgaaccttct cc 32

<210> SEQ ID NO 25
<211> LENGTH: 45
<212> TYPE: DNA
<213> ORGANISM: Artificial Sequence -continued

```
<220> FEATURE:
<223> OTHER INFORMATION: Description of Artificial Sequence: a sequence
      for primer

<400> SEQUENCE: 25

cgcctgggtg gtttgcgttt cctgagaggg agggaggtct ggagt                  45


<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: a sequence
      for primer

<400> SEQUENCE: 26

actccagacc tccctccctc tcaggaaacg caaaccaccc aggcg                  45


<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence: a sequence
      for primer

<400> SEQUENCE: 27

actcgagtgg gcttctgcgc gctccca                                      27
```

METHOD FOR TARGETING A POLYPEPTIDE ONTO CELLULAR SURFACE

This application is a Divisional of application Ser. No. 10/434,269, filed on May 9, 2003, now U.S. Pat. No. 7,326, 530, the entire contents of which are hereby incorporated by reference and for which priority is claimed under 35 U.S.C. § 120. The Ser. No. 10/434,269 application claims priority under 35 U.S.C. § 119(a)-(d) on Patent Application No(s). 2002-173469 filed in JAPAN on Jun. 13, 2002, which is herein incorporated by reference.

BACKGROUND OF THE INVENTION

1. Technical Field

The present invention relates to a polypeptide having an activity for targeting a heterogeneous polypeptide to a surface of cytoplasmic membrane, a nucleic acid encoding the polypeptide, a method for localizing a polypeptide on a cell surface, and a method for detecting the polypeptide or the nucleic acid. More specifically, the present invention relates to a polypeptide having an activity for targeting a heterogeneous polypeptide to a surface of cytoplasmic membrane, and a nucleic acid encoding the polypeptide, which are useful for constructing a protein expression system useful in analyzing functions of the protein; a method for localizing a polypeptide on a surface of cytoplasmic membrane, which is useful for detecting an enzyme, a peptide hormone, various growth factors, a cytokine, a chemokine, an antibody molecule, a complement molecule, a serum protein, a cell adhesion factor, a nucleic acid-binding protein, a neurotrophic factor, a receptor or a ligand; and a method for detecting the polypeptide or a glycosylated polypeptide thereof, or a nucleic acid, which is useful for functional analysis of a protein, a delivery of a cell expressing the polypeptide to a target site in vivo, preparation of an antibody against the polypeptide, preparation of a vaccine using the polypeptide as an antigen, a gene therapy of cancer by which the polypeptide, or the like is targeted.

2. Discussion of the Related Art

With the advancement in sugar chain biology in recent years, the findings concerning the structures and functions of sugar chains of glycoproteins have been accumulated. However, with regard to the structures and functions of O-glycans, i.e., which are so-called mucin type sugar chains, since a convenient analytic method for sugar chain structures has not been established, the analyses have been delayed at present.

In particular, there are only few reports on the biological significance of O-glycosylation of secreted proteins. For instance, there has been reported that O-glycosylation in a C-terminal tandem repeat sequence of rat pancreatic bile salt-dependent lipase regulates the secretion of the lipase. Also, it has also been reported that even in the above rat pancreatic bile salt-dependent lipase, a region rich in proline, glutamic acid, serine, and threonine [referred to as PEST region, *Science,* 234, 364-368 (1986)] masked by O-glycosylation, thereby resulting in the delivery of the lipase to the pathway of the secretion system, not the degradation system [*Journal of Biological Chemistry,* 272, 27353-27361 (1997)].

Furthermore, it has been reported that protein targeting to the apical surface of polar cells is prevented by inhibiting O-glycosylation by mutagenesis in the mucin-like sequence or the mucin box or by means of a metabolism inhibitor or the like [For instance, please see literatures *Journal of Biological Chemistry,* 275, 6566-6572 (2000) for sucrase isomaltase; *Experimental Cell Research,* 258, 184-194 (2000) for dipeptidyl peptidase IV; *Journal of Cell Biology,* 139, 929-940 (1997) and *Journal of Biological Chemistry,* 273, 30263-30270 (1998) for neutrophin receptor and the like]. However, in the above literatures, a sequence necessary for targeting to a surface of the cell membrane or a signal itself has not been specified at present.

SUMMARY OF THE INVENTION

An object of the present invention is to provide a polypeptide having an activity for targeting a heterogeneous polypeptide to a surface of the cytoplasmic membrane, wherein the polypeptide is capable of localizing on a surface of the cytoplasmic membrane a polypeptide not being localized on the surface of the cytoplasmic membrane in nature. Another object of the present invention is to provide a nucleic acid capable of performing preparation of a construct for targeting a heterogeneous polypeptide to a surface of the cytoplasmic membrane, alteration of glycosylation pattern or physicochemical properties of the above polypeptide, facilitation in obtaining the polypeptide of the present invention by genetic engineering, and the like. Still another object of the present invention is to provide a construct for introducing into a cell or a transformant capable of achieving at least one of localization of a polypeptide on the surface of the cytoplasmic membrane, wherein the polypeptide is otherwise not localized on the surface of the cytoplasmic membrane, obtainment of a polypeptide having an activity for targeting a heterogeneous polypeptide to the surface of the cytoplasmic membrane, screening for a receptor or ligand for a polypeptide to be tested, a delivery of a cell to a target site and the like. Still another object of the present invention is to provide a method for localizing a polypeptide on the surface of the cytoplasmic membrane and a kit therefor, which are capable of localizing a polypeptide on the surface of the cytoplasmic membrane otherwise not localized on the surface of the cytoplasmic membrane. Still another object of the present invention is to provide an oligonucleotide probe, a pair of primers, and a kit for detecting a nucleic acid encoding a polypeptide having an activity for targeting a heterogeneous polypeptide to the surface of the cytoplasmic membrane, which are capable of easily detecting the polypeptide or nucleic acid of the present invention, and usable for searching a cytoplasmic membrane-localized protein or deducing the protein from the nucleotide sequence, further searching for a cytoplasmic membrane-localized signal, constructing a vector for expressing a protein comprising the gene encoding the signal, and the like; a method for detecting the nucleic acid; an antibody or fragment thereof capable of specifically binding to the polypeptide or a glycosylated polypeptide thereof; and a method for detecting the polypeptide or a glycosylated polypeptide thereof, or a kit therefor. Still another object of the present invention is to provide a method for detecting a ligand or receptor for a polypeptide, which can be utilized for screening a new ligand or receptor.

Concretely, the gist of the present invention relates to:

[1] a polypeptide comprising an amino acid sequence selected from the group consisting of the following (a) to (c):

(a) the amino acid sequence shown in SEQ ID NO: 2;

(b) an amino acid sequence having at least 40% sequence identity with SEQ ID NO: 2; and (c) an amino acid sequence having at least one mutation in SEQ ID NO: 2 selected from the group consisting of the following (1) to (35):

(1) substitution of an amino acid residue at position 1 to T, (2) substitution of an amino acid residue at position 2 to T, (3) substitution of an amino acid residue at position 3 to P or T, (4) substitution of an amino acid residue at position 4 to T,
(5) substitution of an amino acid residue at position 5 to Q,
(6) substitution of an amino acid residue at position 6 to A,
(7) substitution of an amino acid residue at position 7 to F or P,
(8) substitution of an amino acid residue at position 8 to T,
(9) substitution of an amino acid residue at position 9 to P,
(10) substitution of an amino acid residue at position 11 to L, S or P,
(11) substitution of an amino acid residue at position 12 to N, S or A,
(12) substitution of an amino acid residue at position 13 to S,
(13) substitution of an amino acid residue at position 15 to P,
(14) substitution of an amino acid residue at position 17 to S or P,
(15) substitution of an amino acid residue at position 18 to P, T or A,
(16) substitution of an amino acid residue at position 19 to P,
(17) substitution of an amino acid residue at position 20 to T,
(18) substitution of an amino acid residue at position 21 to S or I,
(19) substitution of an amino acid residue at position 23 to S or T,
(20) substitution of an amino acid residue at position 24 to P or A,
(21) substitution of an amino acid residue at position 25 to T,
(22) substitution of an amino acid residue at position 26 to I,
(23) substitution of an amino acid residue at position 27 to S,
(24) substitution of an amino acid residue at position 28 to S,
(25) substitution of an amino acid residue at position 29 to T,
(26) substitution of an amino acid residue at position 30 to T or Q,
(27) substitution of an amino acid residue at position 31 to N, S, T or A,
(28) substitution of an amino acid residue at position 32 to F or C,
(29) substitution of an amino acid residue at position 33 to R,
(30) substitution of an amino acid residue at position 34 to T,
(31) substitution of an amino acid residue at position 35 to E or T,
(32) substitution of an amino acid residue at position 36 to T,
(33) deletion of a sequence consisting of amino acids at positions 1 to 8,
(34) deletion of a sequence consisting of amino acids at positions 1 to 7, and
(35) deletion of a sequence consisting of amino acids at positions 32 to 36, wherein the polypeptide has an activity for targeting a heterogeneous polypeptide to a surface of cytoplasmic membrane;

[2] a nucleic acid encoding the polypeptide of the above [1], wherein the nucleic acid has a nucleotide sequence selected from the group consisting of the following (A) to (C):

(A) a nucleotide sequence encoding an amino acid sequence selected from the group consisting of the following (a) to (c):
(a) the amino acid sequence shown in SEQ ID NO: 2;
(b) an amino acid sequence having at least 40% sequence identity with SEQ ID NO: 2; and
(c) an amino acid sequence having at least one mutation in SEQ ID NO: 2 selected from the group consisting of the following (1) to (35):
(1) substitution of an amino acid residue at position 1 to T,
(2) substitution of an amino acid residue at position 2 to T,
(3) substitution of an amino acid residue at position 3 to P or T,
(4) substitution of an amino acid residue at position 4 to T,
(5) substitution of an amino acid residue at position 5 to Q,
(6) substitution of an amino acid residue at position 6 to A,
(7) substitution of an amino acid residue at position 7 to F or P,
(8) substitution of an amino acid residue at position 8 to T,
(9) substitution of an amino acid residue at position 9 to P,
(10) substitution of an amino acid residue at position 11 to L, S or P,
(11) substitution of an amino acid residue at position 12 to N, S or A,
(12) substitution of an amino acid residue at position 13 to S,
(13) substitution of an amino acid residue at position 15 to P,
(14) substitution of an amino acid residue at position 17 to S or P,
(15) substitution of an amino acid residue at position 18 to P, T or A,
(16) substitution of an amino acid residue at position 19 to P,
(17) substitution of an amino acid residue at position 20 to T,
(18) substitution of an amino acid residue at position 21 to S or I,
(19) substitution of an amino acid residue at position 23 to S or T,
(20) substitution of an amino acid residue at position 24 to P or A,
(21) substitution of an amino acid residue at position 25 to T,
(22) substitution of an amino acid residue at position 26 to I,
(23) substitution of an amino acid residue at position 27 to S,
(24) substitution of an amino acid residue at position 28 to S,
(25) substitution of an amino acid residue at position 29 to T,
(26) substitution of an amino acid residue at position 30 to T or Q,
(27) substitution of an amino acid residue at position 31 to N, S, T or A,
(28) substitution of an amino acid residue at position 32 to F or C,
(29) substitution of an amino acid residue at position 33 to R,

(30) substitution of an amino acid residue at position 34 to T,
(31) substitution of an amino acid residue at position 35 to E or T,
(32) substitution of an amino acid residue at position 36 to T,
(33) deletion of a sequence consisting of amino acids at positions 1 to 8,
(34) deletion of a sequence consisting of amino acids at positions 1 to 7, and
(35) deletion of a sequence consisting of amino acids at positions 32 to 36;

(B) a nucleotide sequence having at least 27% sequence identity with the nucleotide sequence shown in SEQ ID NO: 1, wherein a polypeptide encoded by the nucleotide sequence has an activity for targeting a heterogeneous polypeptide to a surface of cytoplasmic membrane; and (C) a nucleotide sequence of a nucleic acid capable of hybridizing to an antisense nucleic acid of the nucleic acid consisting of the nucleotide sequence shown in SEQ ID NO: 1 under stringent conditions, wherein a polypeptide encoded by the nucleotide sequence has an activity for targeting a heterogeneous polypeptide to a surface of cytoplasmic membrane;

[3] a construct for introducing into a cell for localizing a heterogeneous polypeptide on a cell surface, comprising one nucleotide sequence selected from the group consisting of the following (A) to (C):

(A) a nucleotide sequence encoding an amino acid sequence selected from the group consisting of the following (a) to (c):
(a) the amino acid sequence shown in SEQ ID NO: 2;
(b) an amino acid sequence having at least 40% sequence identity with SEQ ID NO: 2; and
(c) an amino acid sequence having at least one mutation in SEQ ID NO: 2 selected from the group consisting of the following (1) to (35):
(1) substitution of an amino acid residue at position 1 to T,
(2) substitution of an amino acid residue at position 2 to T,
(3) substitution of an amino acid residue at position 3 to P or T,
(4) substitution of an amino acid residue at position 4 to T,
(5) substitution of an amino acid residue at position 5 to Q,
(6) substitution of an amino acid residue at position 6 to A,
(7) substitution of an amino acid residue at position 7 to F or P,
(8) substitution of an amino acid residue at position 8 to T,
(9) substitution of an amino acid residue at position 9 to P,
(10) substitution of an amino acid residue at position 11 to L, S or P,
(11) substitution of an amino acid residue at position 12 to N, S or A,
(12) substitution of an amino acid residue at position 13 to S,
(13) substitution of an amino acid residue at position 15 to P,
(14) substitution of an amino acid residue at position 17 to S or P,
(15) substitution of an amino acid residue at position 18 to P, T or A,
(16) substitution of an amino acid residue at position 19 to P,
(17) substitution of an amino acid residue at position 20 to T,
(18) substitution of an amino acid residue at position 21 to S or I,
(19) substitution of an amino acid residue at position 23 to S or T,
(20) substitution of an amino acid residue at position 24 to P or A,
(21) substitution of an amino acid residue at position 25 to T,
(22) substitution of an amino acid residue at position 26 to I,
(23) substitution of an amino acid residue at position 27 to S,
(24) substitution of an amino acid residue at position 28 to S,
(25) substitution of an amino acid residue at position 29 to T,
(26) substitution of an amino acid residue at position 30 to T or Q,
(27) substitution of an amino acid residue at position 31 to N, S, T or A,
(28) substitution of an amino acid residue at position 32 to F or C,
(29) substitution of an amino acid residue at position 33 to R,
(30) substitution of an amino acid residue at position 34 to T,
(31) substitution of an amino acid residue at position 35 to E or T,
(32) substitution of an amino acid residue at position 36 to T,
(33) deletion of a sequence consisting of amino acids at positions 1 to 8,
(34) deletion of a sequence consisting of amino acids at positions 1 to 7, and
(35) deletion of a sequence consisting of amino acids at positions 32 to 36;

(B) a nucleotide sequence having at least 27% sequence identity with the nucleotide sequence shown in SEQ ID NO: 1, wherein a polypeptide encoded by the nucleotide sequence has an activity for targeting a heterogeneous polypeptide to a surface of cytoplasmic membrane; and (C) a nucleotide sequence of a nucleic acid capable of hybridizing to an antisense nucleic acid of the nucleic acid consisting of the nucleotide sequence shown in SEQ ID NO: 1 under stringent conditions, wherein a polypeptide encoded by the nucleotide sequence has an activity for targeting a heterogeneous polypeptide to a surface of cytoplasmic membrane;

[4] a transformant harboring the construct for introducing a cell of the above [3];

[5] a method for localizing a polypeptide on a surface of a cytoplasmic membrane, characterized in that the method comprises culturing a transformant harboring the construct for introducing into a cell of the above [3], thereby localizing a heterogeneous polypeptide to be expressed on the surface of cytoplasmic membrane of the resulting cultured cells;

[6] a fusion protein obtained by performing the method of the above [5], consisting of a polypeptide having an activity for targeting a heterogeneous protein to a surface of cytoplasmic membrane, and the heterogeneous protein;

[7] a kit for expressing a heterogeneous polypeptide to be expressed on cytoplasmic membrane, comprising the construct for introducing a cell of the above [3];

[8] an oligonucleotide probe capable of hybridizing to a nucleic acid consisting of the nucleotide sequence shown in SEQ ID NO: 1 or an antisense nucleic acid thereof under stringent conditions, wherein the oligonucleotide probe consists of 15 to 150 nucleotides in length;

[9] a pair of primers consisting of an oligonucleotide capable of hybridizing to a nucleic acid consisting of the nucleotide sequence shown in SEQ ID NO: 1 under stringent conditions, wherein the oligonucleotide consists of 8 to 50 nucleotides in length; and an oligonucleotide capable of hybridizing to an antisense nucleic acid consisting of the nucleotide sequence shown in SEQ ID NO: 1 under stringent conditions, wherein the oligonucleotide consists of 8 to 50 nucleotides in length;

[10] a kit used for detecting a nucleic acid encoding a polypeptide having an activity for targeting a heterogeneous polypeptide to a surface of cytoplasmic membrane, comprising the oligonucleotide probe of the above [8] and/or the pair of primers of the above [9];

[11] a method for detecting a nucleic acid encoding a polypeptide having an activity for targeting a heterogeneous polypeptide to a surface of cytoplasmic membrane, characterized by carrying out the steps of: detecting with a use of the oligonucleotide probe of the above [8] a hybrid therewith; and/or detecting an amplified product by a nucleic acid amplification method using the pair of primers of the above [9] and a nucleic acid to be detected;

[12] an antibody or a fragment thereof, capable of specifically binding to the polypeptide of the above [1], or a glycosylated polypeptide thereof;

[13] a method for detecting a polypeptide having an activity for targeting a heterogeneous polypeptide to a surface of cytoplasmic membrane, characterized in that the method comprises detecting with a use of a substance capable of specifically binding to the polypeptide of the above [1] or a glycosylated polypeptide thereof, and detecting a polypeptide capable of binding to the substance from a sample to be tested;

[14] a kit used for detecting a polypeptide having an activity for targeting a heterogeneous polypeptide to a surface of cytoplasmic membrane, comprising at least one member selected from the group consisting of the antibody or a fragment thereof of the above [12], lectin specific to a mucin type sugar chain, an antibody against Tn antigen or a fragment thereof, and an antibody against T antigen or a fragment thereof;

[15] a method for detecting a ligand or receptor for a polypeptide, characterized in that the method comprises contacting a cultured cell of a transformant with a substance to be tested, wherein the transformant harbors the construct for introducing into a cell of the above [3], and a heterogeneous polypeptide to be expressed is localized on cytoplasmic membrane, and detecting a substance bound to a heterogeneous polypeptide on a surface of the cytoplasmic membrane of the cultured cell;

[16] a kit for detecting a ligand or receptor for a polypeptide by the method of the above [15], comprising a transformant harboring the construct for introducing into a cell of the above [3]; and

[17] a method for delivery of a cell to a target site, characterized in that the method comprises introducing to an individual a transformant harboring the construct for introducing into a cell of the above [3].

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Figure 1A:
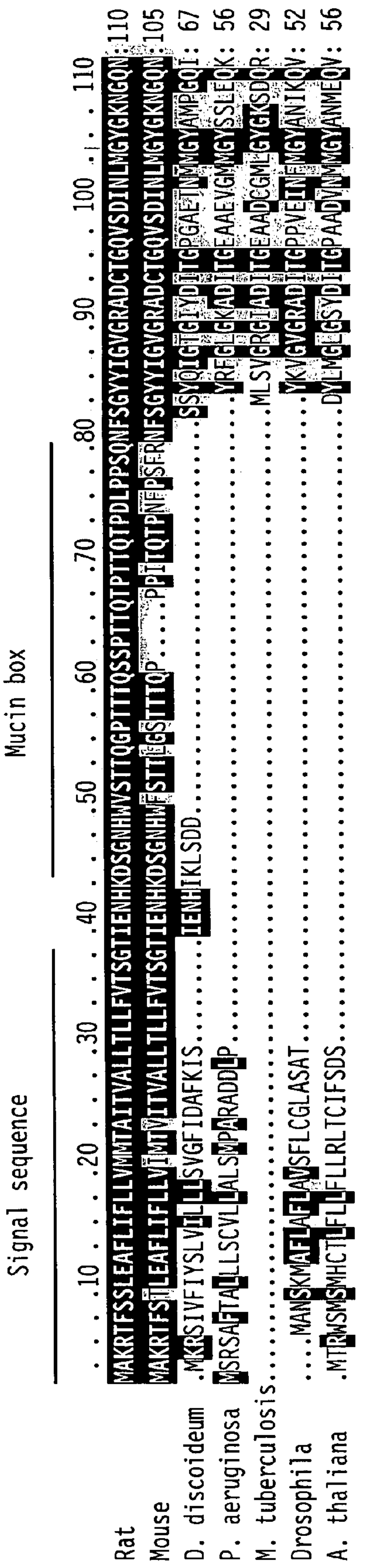
FIG. 1 is a comparative view of the amino acid sequences of neutral ceramidases. Panel A is a comparative view of the N-terminal amino acid sequences deduced from the nucleotide sequences between neutral ceramidases of rat (amino acid nos: 1-110 of SEQ ID NO: 5), mouse (amino acid nos: 1-105 of SEQ ID NO: 3), and neutral ceramidases of other organisms [*Dictyostelium discoideum* (amino acid nos: 1-67 of SEQ ID NO: 6), *Pseudomonas aeruginosa* (amino acid nos: 1-56 of SEQ ID NO: 7), *Mycobacterium tuberculosis* (amino acid nos: 1-29 of SEQ ID NO: 8), *Drosophila melanogaster* (amino acid nos: 1-52 of SEQ ID NO: 9), and *Arabidopsis thaliana* (amino acid nos: 1-56 of SEQ ID NO: 10)]. Panel B shows comparison between the amino acid sequences for the mucin boxes of the neutral ceramidases of rat (SEQ ID NO: 2), mouse (amino acid nos: 43-73 of SEQ ID NO: 3), and the amino acid sequences of other mucin type glycoproteins [rat sucrase isomaltase (SEQ ID NO: 21), human MUC (SEQ ID NO: 22), insect mesenteric mucin (SEQ ID NO: 23)].

The present invention is based on the findings by the present inventors that among the ceramidases which are key enzymes in sphingolipid metabolism, a neutral ceramidase is distributed in endosome-like organelle in rat hepatocyte, but expressed on the raft at the apical membrane of the renal proximal/distal tubules and collecting duct in the kidney. In other words, the present invention is based on the findings by the present inventors that there is an amino acid sequence of a polypeptide having an activity for targeting the ceramidase to the cytoplasmic membrane in the intracellular localization of the above ceramidase. In addition, the present invention is based on a surprising finding by the present inventors that a desired protein can be localized by the polypeptide on the plasma membrane when the desired protein is expressed in an animal cell.

Incidentally, in the present specification, an amino acid residue may be expressed by a single character representation of the amino acid according to the commonly used biochemical nomenclature.

According to the present invention, there is provided a polypeptide comprising an amino acid sequence selected from the group consisting of the following (a) to (c):

(a) the amino acid sequence shown in SEQ ID NO: 2;

(b) an amino acid sequence having at least 40% sequence identity with SEQ ID NO: 2; and (c) an amino acid sequence having at least one mutation in SEQ ID NO: 2 selected from the group consisting of the following (1) to (35):

(1) substitution of an amino acid residue at position 1 to T;
(2) substitution of an amino acid residue at position 2 to T;
(3) substitution of an amino acid residue at position 3 to P or T;
(4) substitution of an amino acid residue at position 4 to T;
(5) substitution of an amino acid residue at position 5 to Q;
(6) substitution of an amino acid residue at position 6 to A;
(7) substitution of an amino acid residue at position 7 to F or P;
(8) substitution of an amino acid residue at position 8 to T;
(9) substitution of an amino acid residue at position 9 to P;
(10) substitution of an amino acid residue at position 11 to L, S or P;
(11) substitution of an amino acid residue at position 12 to N, S or A;
(12) substitution of an amino acid residue at position 13 to S;
(13) substitution of an amino acid residue at position 15 to P;
(14) substitution of an amino acid residue at position 17 to S or P;
(15) substitution of an amino acid residue at position 18 to P, T or A;
(16) substitution of an amino acid residue at position 19 to P;
(17) substitution of an amino acid residue at position 20 to T;
(18) substitution of an amino acid residue at position 21 to S or I;
(19) substitution of an amino acid residue at position 23 to S or T;
(20) substitution of an amino acid residue at position 24 to P or A;
(21) substitution of an amino acid residue at position 25 to T;
(22) substitution of an amino acid residue at position 26 to I;
(23) substitution of an amino acid residue at position 27 to S;
(24) substitution of an amino acid residue at position 28 to S;
(25) substitution of an amino acid residue at position 29 to T;
(26) substitution of an amino acid residue at position 30 to T or Q;
(27) substitution of an amino acid residue at position 31 to N, S, T or A;
(28) substitution of an amino acid residue at position 32 to F or C;
(29) substitution of an amino acid residue at position 33 to R;
(30) substitution of an amino acid residue at position 34 to T;
(31) substitution of an amino acid residue at position 35 to E or T;
(32) substitution of an amino acid residue at position 36 to T;
(33) deletion of a sequence consisting of amino acids at positions 1 to 8;
(34) deletion of a sequence consisting of amino acids at positions 1 to 7; and
(35) deletion of a sequence consisting of amino acids at positions 32 to 36, wherein the polypeptide has an activity for targeting a heterogeneous polypeptide to a surface of cytoplasmic membrane.

Since the polypeptide of the present invention comprises the above amino acid sequence, there is exhibited an excellent effect that when a heterogeneous polypeptide is linked downstream the polypeptide, the heterogeneous polypeptide is targeted to the surface of the cytoplasmic membrane.

The term "heterogeneous polypeptide" as used herein means a polypeptide to be expressed not comprising any of the amino acid sequences of the above (a) to (c) as a portion thereof, for instance, a polypeptide other than the rat kidney ceramidase. Concretely, there are included enzymes, peptide hormones, various growth factors, cytokines, chemokines, antibody molecules, complement molecules, serum proteins, cell adhesion factors, nucleic acid-binding proteins, neurotrophic factors, receptors, ligands and the like.

As mentioned above, the term "polypeptide having an activity for targeting (a heterogeneous polypeptide) to the surface of the cytoplasmic membrane" as used herein refers to a polypeptide having necessary and sufficient abilities of localizing a heterogeneous polypeptide on the surface of the cytoplasmic membrane.

The amino acid sequence shown in the above SEQ ID NO: 2 is a mucin box found at an N-terminal portion of rat kidney ceramidase [*Journal of Biological Chemistry,* 276, 26249-26259 (2001)], which is a sequence having little sequence homology with the mucin-like domain found in enteropeptidase [*Journal of Biological Chemistry,* 277, 6858-6863 (2002)]. Although it has been suggested that the mucin-like domain of the above enteropeptidase is a signal for directing the sorting to the apical face in MDCK cell from dog kidney, modification by O-glycan is not considered to be necessary for the targeting.

In the above mucin box, there exists a "site to which O-glycan can be added" shown in amino acid nos: 10, 14, 15, 16, 18, 19, 21, 22, 24, 26, 27 and 29 in the amino acid sequence shown in SEQ ID NO: 2. The "site to which O-glycan can be added" includes those having sequence identity of at least 40%, preferably at least 50%, more preferably at least 60%, and still more preferably at least 70% to the amino acid sequence shown in SEQ ID NO: 2. The amino acid residue in the above site is not particularly limited, as long as O-glycan can be added thereto, and is preferably, for instance, threonine (T) or serine.

The above "activity for targeting a heterogeneous polypeptide to the surface of the cytoplasmic membrane" (hereinafter referred to as "targeting activity") can be evaluated by a method for determining the activity comprising expressing a polypeptide to be evaluated (e.g., the polypeptide of the present invention) with a vector tagged with, for example, a fluorescent protein like *Aequoria Victoria* green fluorescent protein (GFP), histidine (His) tag, or a particular epitope, and determining the expression level and localization with the fluorescent protein, His tag, epitope, or the like as a reporter. The vectors used in the evaluation method include, for instance, N-terminal fusion protein expression vectors such as pDsRed2-N1, pECFP-N1, pEGFP-N1, pEGFP-N2, pEGFP-N3 and pEYFP-N1 vectors (manufactured by Clontech); and pcDNA vectors tagged with His tag or a myc tag, such as pcDNA3.1/Myc-his(+) (manufactured by Invitrogen).

In the present invention, in addition to the mucin box polypeptide consisting of a naturally occurring amino acid sequence (the above SEQ ID NO: 2), the polypeptide may also be a polypeptide comprising an amino acid sequence having sequence identity of at least 40% to the amino acid sequence shown in SEQ ID NO: 2, which is a naturally occurring amino acid sequence, as long as similar targeting activity is found when determined by the above method for determining the activity. In the present invention, it is desired that the above sequence identity is at least 40%, preferably 50% or more, more preferably 60% or more, still more preferably 65% or more, still more preferably 70% or more.

The term "sequence identity" as used herein refers to sequence similarity of residues between two molecules, concretely between two polypeptides or between two nucleic acids. The above "sequence identity" can be determined by comparing the two sequences aligned in an optimal state over the sequence region to be compared. Here, the polypeptide or nucleic acid to be compared may have addition or deletion (for instance, gap and the like) as compared to a reference sequence (for instance, consensus sequence and the like) for an optimal alignment of the two sequences. The numerical value (percentage) of the sequence identity can be calculated by determining the same residues existing in both the sequences, determining the number of matching sites, subsequently dividing the number of the above matching sites by the total number of residues within the sequence region to be compared, and multiplying the obtained quotient by 100. Although it is not particularly limited, when the homology of the amino acid sequence is 40%, it can be considered that two bases in the codon coincide on a DNA level, and the identity of the nucleotide sequence can be calculated to be 40(%)× ⅔≈27%.

The algorithms for obtaining the optimal alignment and homology include, for instance, the local homology algorithm of Smith et al. [*Add. APL. Math.,* 2, 482 (1981)], the homology alignment algorithm of Needleman et al. [*J. Mol. Biol.,* 48, 443 (1970)], the homology search method of Pearson et al. *[Proc. Natl. Acad. Sci. USA,* 85, 2444 (1988)], and the multiple alignment by the ClustalW method of Higgins et al.; more concretely, there are included the dynamic programming method, the gap penalty method, the Smith-Waterman algorithm, the Good-Kanehisa algorithm, the BLAST algorithm, the FASTA algorithm and the like. All teachings of these literatures are incorporated herein by reference.

The sequence identity is, for instance, determined by using sequence analysis software, concretely BLASTP or the like for polypeptides and BLASTN or the like for nucleic acids. The BLAST algorithm is used under conditions in common use, with the conditions made stricter as appropriate, including, for instance, an expect value of 10, a word size of 3, and a gap cost (existence: 11, extension: 1). The above BLASTP and BLASTN are generally available on the internet at the web page of the National Center for Biotechnology Information [NCBI], National Library of Medicine [NLM], National Institutes of Health [NIH].

Furthermore, in addition to the mucin box polypeptide consisting of a naturally occurring amino acid sequence (the above SEQ ID NO: 2), the present invention encompasses a polypeptide comprising an amino acid sequence having at least one mutation selected from the group consisting of the above (1) to (35) in the amino acid sequence shown in SEQ ID NO: 2, which is a naturally occurring amino acid sequence, as long as similar targeting activity is found when determined by the above method for determining the activity. In addition, in the present invention, the polypeptide may be a polypeptide comprising an amino acid sequence having two or more mutations selected from the group consisting of the above (1) to (35), as long as the resulting polypeptide has the targeting activity. Here, the above "amino acid sequence having a mutation" includes all naturally occurring variants and amino acid sequences into which an artificial mutation thereinto is introduced. The introduction of a mutation into the polypeptide can be carried out by a commonly used method for introducing a mutation using the nucleic acid of the present invention described below.

The polypeptide of the present invention can also be obtained by synthesizing by a commonly used chemical synthesis method using a peptide synthesizer or the like, or by expressing the nucleic acid of the present invention described below by a commonly used genetic engineering technique.

The above chemical synthesis methods include, for instance, the methods described in *Peptide Synthesis*, Interscience, New York (1966); *Pepuchido Gosei* (*Peptide Synthesis*), Maruzen (1975); *Pepuchido Gosei no Kiso to Jikken* (*Fundamentals and Experimentation of Peptide Synthesis*), Maruzen, and the like. The genetic engineering techniques include, for instance, the methods described in *Molecular Cloning: A Laboratory Manual,* 3rd Ed., Cold Spring Harbor Laboratory Press (2001) and the like. All teachings of these literatures are incorporated herein by reference.

According to the present invention, there is further provided a nucleic acid encoding the polypeptide of the present invention. The nucleic acid of the present invention is a gene encoding the above polypeptide having an activity for targeting signal to the surface of the cytoplasmic membrane, and hence referred to a nucleic acid having a nucleotide sequence encoding the amino acid sequence of a mucin box. Concrete examples of the nucleic acid of the present invention include one nucleotide sequence selected from the group consisting of the following (A) to (C):

(A) a nucleotide sequence encoding an amino acid sequence selected from the group consisting of the above (a) to (c);

(B) a nucleotide sequence having at least 27% sequence identity with the nucleotide sequence shown in SEQ ID NO: 1, wherein a polypeptide encoded by the nucleotide sequence has an activity for targeting a heterogeneous polypeptide to a surface of cytoplasmic membrane; and (C) a nucleotide sequence of a nucleic acid capable of hybridizing to an antisense nucleic acid of the nucleic acid consisting of the nucleotide sequence shown in SEQ ID NO: 1 under stringent conditions, wherein a polypeptide encoded by the nucleotide sequence has an activity for targeting a heterogeneous polypeptide to a surface of cytoplasmic membrane.

According to the nucleic acid of the present invention, there is exhibited an excellent effect that the heterogeneous polypeptide can be targeted to the surface of the cytoplasmic membrane by arranging a nucleic acid encoding the heterogeneous polypeptide to be expressed downstream of the nucleic acid of the present invention, or optionally arranging a nucleic acid encoding a secretion signal and a nucleic acid encoding the heterogeneous polypeptide to be expressed downstream of the nucleic acid of the present invention, and expressing the resulting product. Furthermore, according to the nucleic acid of the present invention, there is exhibited an excellent effect that a construct for targeting a heterogeneous polypeptide to the surface of the cytoplasmic membrane, for instance, an expression vector or the like, can be prepared. In addition, since the nucleic acid of the present invention encodes the polypeptide of the present invention, while the polypeptide of the present invention has a targeting signal to the surface of the cytoplasmic membrane, the nucleic acid of the present invention exhibits an excellent effect that the glycosylation pattern and physicochemical properties can be modified. Moreover, the nucleic acid of the present invention exhibits an excellent effect that the polypeptide of the present invention can be obtained by genetic engineering.

Figure 1B:
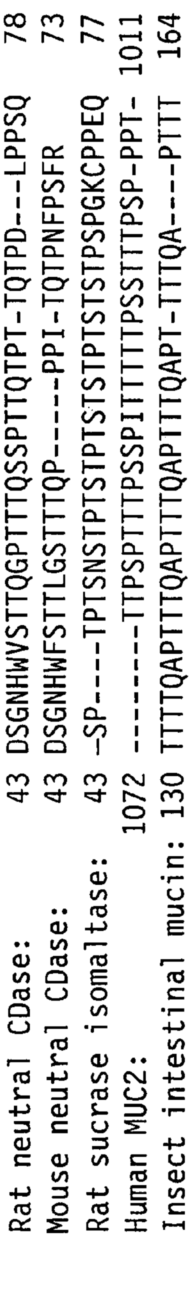

With regard to the above nucleotide sequence (A), concrete examples of the nucleic acid encoding a polypeptide comprising the above amino acid sequence (a) include the nucleotide sequence shown in SEQ ID NO: 1 and a nucleotide sequence differing from the nucleotide sequence of SEQ ID NO: 1 via degeneracy. The nucleic acid encoding a polypeptide comprising the above amino acid sequence (a) can, for instance, be obtained as described below. Concretely, DNA encoding a rat kidney ceramidase may be obtained, to obtain DNA corresponding to a polypeptide having an activity for targeting a heterogeneous polypeptide to the surface of the cytoplasmic membrane. Here, since the amino acid sequence of rat kidney ceramidase has been found to be very highly homologous to mouse liver ceramidase (SEQ ID NO: 3), a mouse kidney ceramidase gene can be obtained by carrying out PCR with a commercially available rat kidney cDNA library as a template and colony hybridization, using a pair of primers and a probe designed on the basis of the information of the nucleotide sequence of the mouse liver ceramidase [*Journal of Biological Chemistry,* 275, 11229-11234 (2000)] in accordance with the method described in *Journal of Biological Chemistry,* 276, 26249-26259 (2001). The entire nucleotide sequence of the DNA thus obtained encoding a rat kidney ceramidase is shown in SEQ ID NO: 4. Also, the amino acid sequence of the ceramidase deduced from the nucleotide sequence shown in the above SEQ ID NO: 4 is shown in SEQ ID NO: 5. By comparing the amino acid sequence shown in the above SEQ ID NO: 5, the N-terminal amino acid sequence of mouse liver ceramidase shown in SEQ ID NO: 3, and the N-terminal amino acid sequences of each of the neutral ceramidases of *Dictyostelium discoideum, Pseudomonas aeruginosa, Mycobacterium tuberculosis, Drosophila melanogaster*, and *Arabidopsis thaliana*, respectively, shown in each of SEQ ID NOs: 6, 7, 8, 9 and 10, it is found that a serine, threonine and proline-rich repeat sequence, which does not exist in the ceramidases of other bacteria and non-vertebrate animals, namely, a mucin box exists immediately downstream of the N-terminal signal sequences of the rat and mouse neutral ceramidases. FIG. 1 shows the deduced N-terminal structures of various neutral ceramidases. The nucleic acid encoding a polypeptide comprising the amino acid sequence of the above (a) can be obtained from the DNA obtained by a commonly used method.

In the above nucleotide sequence (A), the nucleic acid encoding a polypeptide comprising the amino acid sequence of the above (b) or (c) can be obtained by introducing a desired mutation into a nucleic acid encoding a polypeptide comprising the amino acid sequence of the above (a) by a commonly used method of mutagenesis.

The method for introducing a mutation includes, for instance, a method for generating a transition mutation in which cytosine base is substituted with uracil base by a chemical treatment using sodium hydrogen sulfite [*Proceedings of the National Academy of Sciences of the USA,* 79, 1408-1412 (1982)], a method comprising carrying out PCR in a manganese-containing reaction mixture to lower the accuracy of the nucleotide uptake during DNA synthesis [*Anal. Biochem.,* 224, 347-353 (1995)] and the like for a method for introducing a random mutation; and includes, for instance, a method utilizing an amber mutation [gapped duplex method, *Nucleic Acids Research,* 12, 9441-9456 (1984)], a method utilizing a host lacking both the dut (dUTPase) and ung (uracil-DNA glycosylase) genes [Kunkel method, *Proceedings of the National Academy of Sciences of the USA,* 82, 488-492 (1985)], and a method according to PCR utilizing an amber mutation (WO 98/02535) for a method for introducing site-directed mutagenesis; and the like. All teachings of these literatures are incorporated herein by reference. Various kits for introducing site-directed mutation in the desired gene by these methods are commercially available. By utilizing the kit, a gene into which a mutation corresponding to the desired amino acid mutation is introduced can be obtained, to obtain a polypeptide comprising an amino acid sequence having the desired mutation. The nucleic acid of the present invention can be obtained by using the appearance of the targeting activity as an index by expressing a polypeptide encoded by the resulting nucleic acid by a commonly used genetic engineering technique, and determining the activity of the polypeptide by the above method for determining the targeting activity.

In the present invention, the nucleic acid may be a nucleic acid having a nucleotide sequence of the above (B), namely one having a nucleotide sequence having a sequence identity of at least 27%, preferably 50% or more, more preferably 70% by weight or more to the nucleotide sequence shown in SEQ ID NO: 1, as long as its encoded polypeptide is a polypeptide having an activity for targeting a heterogeneous polypeptide to the surface of cytoplasmic membrane.

In addition, in the present invention, the nucleic acid may be a nucleic acid having a nucleotide sequence of the above (C), namely one having a nucleotide sequence capable of hybridizing to an antisense nucleic acid of a nucleic acid consisting of the nucleotide sequence shown in SEQ ID NO: 1 under stringent conditions, as long as its encoded polypeptide is a polypeptide having an activity for targeting a heterogeneous polypeptide to the surface of cytoplasmic membrane.

Here, the hybridization can be carried out in accordance with the method described, for instance, in the above *Molecular Cloning: A Laboratory Manual,* 3rd Ed. (all teachings of which are incorporated herein by reference). Also, the conditions for hybridization include, for instance, conditions of carrying out incubation at 65° C. overnight together with a probe in a solution containing 6×SSC (the composition of 1×SSC: 0.15 M NaCl, 0.015 M sodium citrate, pH 7.0), 0.5% SDS, 5×Denhardt's, and 100 μg/ml herring sperm DNA.

In addition, a nucleic acid having a sequence identity of at least about 27% to the nucleotide sequence shown in SEQ ID NO: 1, more strictly 50% or more, still more strictly 70% or more can be obtained by carrying out the hybridization under the conditions of a lower ionic strength, for instance, conditions of 5×SSC, 3×SSC or the like and/or hybridization at a higher temperature, for instance, 25° C. below a Tm value of the nucleic acid used, more stringently 22° C. below a Tin, still more stringently 20° C. below a Tm, or the like, concretely, although it may differ depending upon the Tm value of the nucleic acid used, at 65° C. or higher, more stringently at 67° C. or higher, still more stringently at 70° C. or higher, or the like, from the viewpoint of further increasing the accuracy in the hybridization under the stringent conditions; carrying out more strict washing conditions, concretely using a buffer with a low ionic strength, for instance, 2×SSC, more strictly 1×SSC, still more strictly 0.5×SSC, and carrying out washing at a higher temperature, for instance, 40° C. below a Tin value of the nucleic acid used, more strictly 30° C. below a Tm, still more strictly 25° C. below a Tm, and concretely although it may differ depending upon the Tin value of the nucleic acid used, washing at 30° C. or higher, more strictly at 37° C. or higher, still more strictly at 42° C. or higher, still more strictly at 45° C. or higher. Here, $T_m$ of the oligonucleotide probe or primer can be calculated, for instance, by the following equation:

$$T_m=81.5-16.6(\log_{10}[Na^+])+0.41(\% G+C)-(600/N).$$

The nucleic acid of the present invention can be obtained by expressing the polypeptide encoded by the resulting nucleic acid by a commonly used genetic engineering technique, and by using the appearance of a targeting activity for the polypeptide as an index as determined by the above method for determining the activity.

The nucleic acid of the present invention can be expressed in various hosts by ligating the nucleic acid to a known vector or the like. The codon usage differs depending upon hosts into which the nucleic acid of the present invention is introduced, and the expression may be suppressed in some cases. In this case, the codon used in the nucleic acid of the present invention may be changed by another codon matching each of hosts to be used.

According to the nucleic acid of the present invention, there is provided a construct for introducing into a cell for localizing a heterogeneous polypeptide on the cell surface, i.e., a construct for introducing the nucleic acid of the present invention into a cell. One of the significant features of the construct of the present invention for introducing into a cell resides in that the construct comprises a nucleotide sequence selected from the group consisting of the above (A) to (C).

Therefore, according to the construct of the present invention for introducing into a cell, a nucleic acid encoding a fusion protein formed between a heterogeneous polypeptide to be targeted to the surface of the cytoplasmic membrane and the polypeptide of the present invention can be easily obtained by operably arranging (linking) a nucleic acid encoding a heterogeneous polypeptide to be expressed downstream of a nucleotide sequence selected from the group consisting of (A) to (C) in the construct of the present invention for introducing into a cell, or optionally downstream of a nucleic acid encoding a secretion signal and one nucleotide sequence selected from the group consisting of (A) to (C). Also, according to the construct for introducing into a cell, there is exhibited an excellent effect that a nucleic acid encoding the fusion protein can be easily introduced into a cell used as a host. Furthermore, according to the construct of the present invention for introducing into a cell, there is exhibited an excellent effect that a heterogeneous polypeptide can be targeted to the surface of the cytoplasmic membrane.

Here, the term "operably (linked)" means that a heterogeneous polypeptide to be expressed and its physiological activity can be expressed in a host cell, and that the heterogeneous polypeptide is linked so that it is expressed as a fusion protein with the polypeptide of the present invention.

The construct of the present invention for introducing into a cell may further comprise a nucleotide sequence for operably linking a nucleic acid encoding a heterogeneous polypeptide downstream one nucleotide sequence selected from the group consisting of the above (A) to (C).

The construct of the present invention for introducing into a cell includes a construct introducing into a cell in which a nucleic acid encoding a heterogeneous polypeptide to be expressed is operably linked downstream of a nucleotide sequence selected from the group consisting of the above (A) to (C), or optionally downstream of a nucleic acid encoding a secretion signal and a nucleotide sequence selected from the group consisting of the above (A) to (C); and a construct for introducing into a cell in which a nucleic acid encoding a heterogeneous polypeptide to be expressed is operably linked downstream of a nucleotide sequence selected from the group consisting of the above (A) to (C), or optionally downstream of a nucleic acid encoding the secretion signal and a nucleotide sequence selected from the group consisting of the above (A) to (C), via a nucleotide sequence for operably linking the nucleic acid encoding the heterogeneous polypeptide [i.e., a construct for introducing into a cell wherein the construct further comprises a nucleotide sequence for operably linking a nucleic acid encoding a heterogeneous polypeptide downstream one nucleotide sequence selected from the group consisting of the above (A) to (C), and wherein the nucleic acid encoding a heterogeneous polypeptide to be expressed is operably linked to the nucleotide sequence for operably linking the heterogeneous gene].

The forms of the above "construct for introducing into a cell" include naked-DNA consisting of a nucleotide sequence selected from the group consisting of the above (A) to (C), and a nucleotide sequence for operably linking a heterogeneous gene downstream of the one nucleotide sequence; an expression vector comprising a nucleotide sequence selected from the group consisting of the above (A) to (C), and a nucleotide sequence for operably linking a heterogeneous gene downstream of the one nucleotide sequence; a construct in which the naked-DNA is supported by a carrier such as liposome or a gold particle. Here, the above expression vector is not limited to plasmid-derived vectors alone, and may be a vector derived from phage, cosmid, or the like, as long as the objects of the present invention would not be hindered. From the viewpoint of easily and massively producing the polypeptide of the present invention, it is desirable that the above expression vector is a vector capable of inducing expression of an exogenous gene, a vector capable of expressing as a fusion protein with a reporter gene product, or the like.

According to the construct of the present invention for introducing into a cell, there is exhibited an excellent effect that the heterogeneous polypeptide to be expressed can be targeted to the surface of the cytoplasmic membrane by introducing the construct into a host capable of adding an O-glycan thereto as a posttranslational modification. Therefore, the construct of the present invention for introducing into a cell can, for instance, be used for localization of a polypeptide to be expressed to the surface of the cytoplasmic membrane, screening for a receptor or ligand for a polypeptide to be tested, delivery of a cell to a target site, preparation of an antibody against the polypeptide, preparation of a vaccine with the polypeptide as an antigen, and cancer gene therapy with the polypeptide as a target.

According to the present invention, in order to target the heterogeneous polypeptide to be expressed to the surface of the cytoplasmic membrane, the heterogeneous protein be expressed may be expressed in a cell as a fusion protein by linking a mucin box having a signal for targeting to the surface of the cytoplasmic membrane, i.e., the polypeptide of the present invention to the N-terminal of the heterogeneous polypeptide to be expressed.

In the present invention, the polypeptide of the present invention can be linked alone to the N-terminal of a heterogeneous polypeptide to be expressed. It is desired that preferably both the secretion signal sequence and the polypeptide of the present invention are added to the N-terminal of the heterogeneous polypeptide to be expressed.

As the above secretion signal sequence, in the case where the heterogeneous polypeptide to be expressed is a secretory protein, a secretion signal sequence of the heterogeneous polypeptide can be used. For instance, a secretion signal sequence for rat kidney ceramidase and a secretion signal sequence for mouse liver ceramidase can be generally used. In addition, when the heterogeneous polypeptide to be expressed is a membrane-bound protein, both a secretion signal sequence and a mucin box can be added to the N-terminal thereof after removing the transmembrane region. Concrete examples of the secretion signal sequences include, for instance, but are not particularly limited to, amino acid nos: 1-36 of SEQ ID NO: 11, amino acid nos: 1-36 of SEQ ID NO: 3 and the like.

A method for constructing a plasmid vector type construct for introducing into a cell will be hereinafter described, in a case where the heterogeneous polypeptide to be expressed is green fluorescent protein (GFP). GFP to which both the polypeptide of the present invention and a secretion signal sequence are added (S-M-GPF) is designed using amino acid nos: 1-78 (methionine at position 1-glutamine at position 78) of SEQ ID NO: 17 and amino acid nos: 1-42 (methionine at position 1-lysine at position 42) of SEQ ID NO: 11. Gene fragments encoding these fragments are amplified by PCR respectively using:

a pair of primers consisting of 5'-primer 5 having KpnI recognition site (SEQ ID NO: 18, 5'-AGGGTACCGAAATGGCAAAGCGAACCTTCTCC-3') and 3'-primer 6 having BamHI recognition site (SEQ ID NO: 19, 5'-CCACGGATCCCCTGAGAGGGAGGGAGGTCTGG-3') for amino acid nos: 1-78 of SEQ ID NO: 17, and a pair of primers consisting of 5'-primer 5 (the above SEQ ID NO: 18) and 3'-primer 7 having BamHI recognition site (SEQ ID NO: 20, 5'-TTCCGGATCCCTTTGTGGTTTTCGATGGTCCC-3') for amino acid nos: 1-42 of SEQ ID NO: 11.

Figure 2:
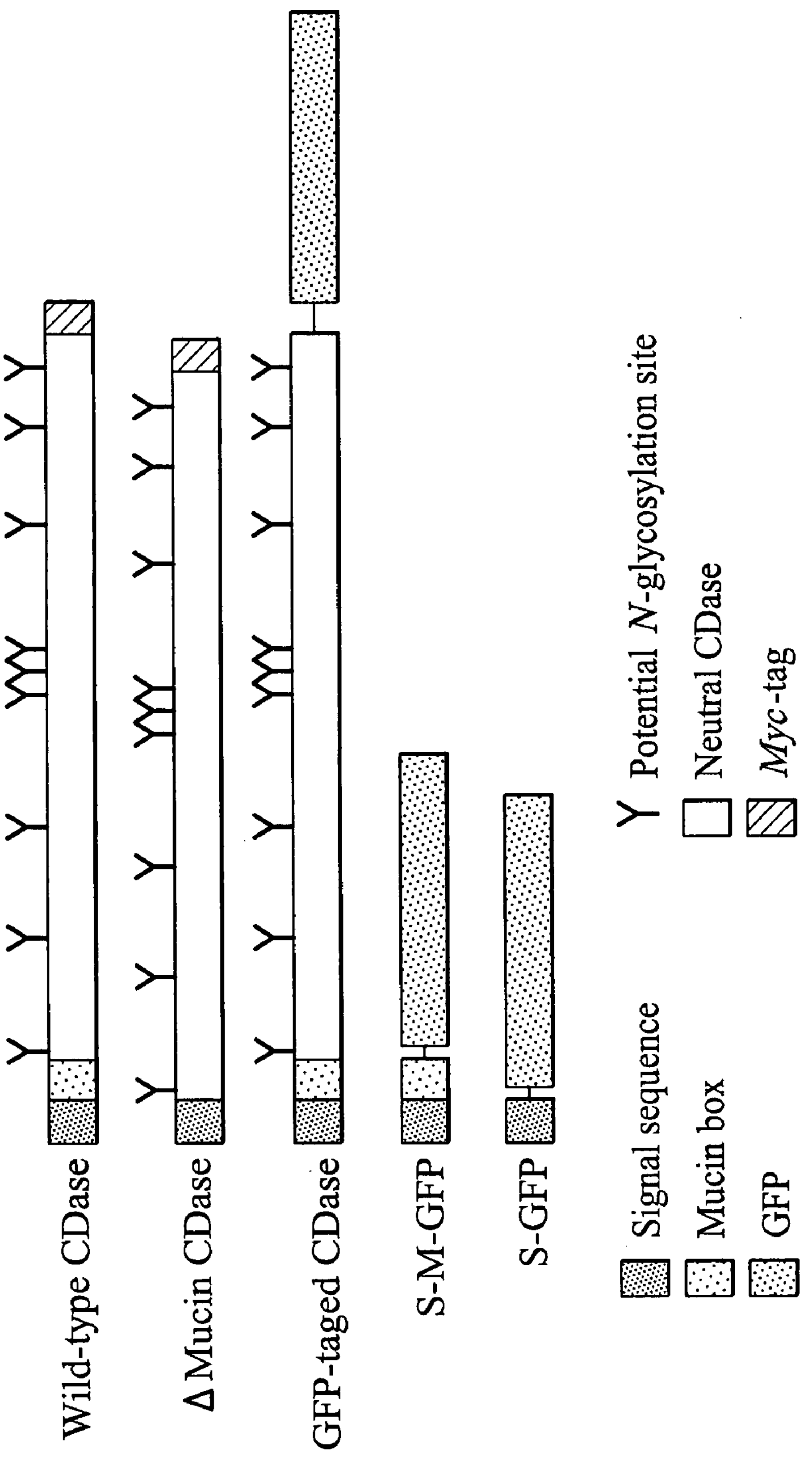
FIG. 2 shows the domain structure of rat neutral CDase and the structures of various mutants. The schematic view shows a wild-type neutral ceramidase (Wild-type CDase in the figure), a mucin box-deleted mutant (Δmucin CDase in the figure), a C-terminal GFP-tagged ceramidase (GFP-tagged CDase in the figure), a signal sequence-mucin box-GFP fusion protein (S-M-GFP in the figure), and a signal sequence fused GFP (S-GFP in the figure).

The resulting amplified products are subcloned into a vector, for instance, pEGFP-N2 (trade name, manufactured by Clontech). A construct having the desired nucleotide sequence can be obtained as the construct of the present invention for introducing into a cell (plasmid vector) by confirming the nucleotide sequence for all the constructs obtained using a DNA sequencer (trade name: Model 377, manufactured by Applied Biosystems). The schematic diagram of the above plasmid vector is shown in FIG. 2.

Furthermore, the transformant of the present invention can be obtained by introducing (transforming or transfecting) into a host the construct of the present invention for introducing into a cell. One of the features of the transformant of the present invention resides in that the transformant harbors the construct of the present invention for introducing into a cell, specifically a construct for introducing into a cell, comprising a nucleic acid encoding a heterogeneous polypeptide to be expressed. According to the transformant of the present invention, there is exhibited an excellent characteristic that a heterogeneous polypeptide to be expressed is targeted to the surface of the cytoplasmic membrane. Therefore, the transformant of the present invention can, for example, e.g., be used for localization of the polypeptide to be expressed on the surface of the cytoplasmic membrane, screening for a receptor or ligand for a polypeptide to be tested, preparation of an antibody against the polypeptide, preparation of a vaccine with the polypeptide as an antigen, cancer gene therapy with the polypeptide as a target, and the like.

The hosts include animal cells, plant cells and the like. Also, in order to express the heterogeneous polypeptide to be expressed on the surface of the cytoplasmic membrane, it is necessary that a portion of the polypeptide of the present invention undergoes modification by O-glycan. Accordingly, as the above host, there may generally be used a cell expressing a group of glucosyltransferases necessary for O-glycosylation, and also expressing a glycoprotein having a mucin type sugar chain. The glucosyltransferase for the above O-glycosylation product includes, for instance, polypeptide N-acetylgalactosaminyltransferase (EC 2.4.1.41), glycoprotein-N-acetylgalactosamine 3-β-galactosyltransferase (EC 2.4.1.122), N-acetyllactosaminide-β-1,3-N-acetylglucosaminyltransferase (EC 2.4.1.149)], (α-N-acetyl-neuraminyl-2,3-β-galactosyl-1,3)-N-acetylgalactosaminide α-2,6-sialyltransferase (EC 2.4.99.7), β-galactosamide α-2,6-sialyltransferase (EC 2.4.99.1), β-galactoside α-2,3-sialyltransferase (EC 2.4.99.4), N-acetyllactosamine synthase (EC 2.4.1.90), N-acetyllactosaminide β-1,3-N-acetylglucosaminyltransferase (EC 2.4.1.149), β-1,3-galactosyltransferase and the like. The host used in the present invention may be a cell expressing appropriately the group of these enzymes, and processing a glycoprotein accurately in the endoplasmic reticulum and Golgi apparatus, to express a glycoprotein having O-glycan. More concrete examples of the above host include, but are not limited to, HEK293 cell, CHOP cell, MDCK cell from dog kidney and the like.

Concretely, the transformant of the present invention can be obtained by carrying out the steps of:

(I) operably linking downstream a nucleotide sequence selected from the group consisting of the above (A) to (C) a nucleic acid encoding a heterogeneous polypeptide to be expressed in the construct for introducing into a cell, and (II) introducing the product obtained in the above step (I) into a host capable of adding an O-glycan thereto as a posttranslational modification, to give a transformant harboring the construct of the present invention for introducing a cell, concretely a construct for introducing into a cell, comprising a nucleic acid encoding a heterogeneous polypeptide to be expressed.

According to the transformant of the present invention, there may also be provided a method for delivering a cell to a target site, characterized in that the method comprises introducing a transformant to an individual.

According to the present invention, there is provided a method for localizing a polypeptide on the surface of the cytoplasmic membrane. One of the significant features of the localization method of the present invention resides in that the transformant of the present invention is cultured, to thereby localize a heterogeneous polypeptide to be expressed on the plasma membrane of the cultured cell obtained. Therefore, according to the localization method of the present invention, there is exhibited a surprisingly excellent effect that a polypeptide which would not be localized on the surface of the cytoplasmic membrane in nature can be localized to the surface of the cytoplasmic membrane.

In the localization method of the present invention, the heterogeneous polypeptide to be expressed can be localized on the surface of the cytoplasmic membrane having a signal for targeting to the surface of the cytoplasmic membrane as a fusion protein formed between the polypeptide of the present invention and the heterogeneous polypeptide to be expressed, by culturing the transformant of the present invention under the conditions appropriate for the host and the heterogeneous polypeptide to be expressed. When the transformant is a cultured cell, each heterogeneous polypeptide to be expressed can be efficiently expressed by determining the optimal conditions for expression of the heterogeneous polypeptide to be expressed on the surface of the cytoplasmic membrane with respect to the amount of inducer used, duration of its use, and the like, as well as medium composition, medium pH, culturing temperature, and culturing time.

Here, the confirmation of the fusion protein formed between the polypeptide of the present invention and the heterogeneous polypeptide to be expressed can be made by determining expression using an antibody against the polypeptide of the present invention. Alternatively, the confirmation can be carried out by determining expression of the heterogeneous polypeptide to be expressed on the surface of the cytoplasmic membrane. The determination of the activity can be carried out by using a protein, an antibody, or the like capable of specifically binding to the heterogeneous polypeptide to be expressed. For example, the expression on the cell surface can be determined by using an antibody against the tag sequence in a case where the construct for introducing into a cell used comprises a tag sequence, using a chelating resin or the like in a case where the tag sequence is a histidine tag, or the like. In addition, in the case where a tag itself emits fluorescence such as GFP, expression on the cell surface can be confirmed by directly determining the fluorescence signal. The determination methods include a method comprising immunostaining an expressed cell with a primary antibody specific to the heterogeneous polypeptide to be expressed, the tag sequence, or the like, and a fluorescently-labeled secondary antibody, and observing the fluorescence signal on the cell surface using a confocal laser fluorescence microscope; a method comprising measuring stained cells by flow cytometry; and the like. In addition, there are included preparing a cytoplasmic membrane fraction, and carrying out Western blotting with an antibody against the heterogeneous polypeptide to be expressed or a specific antibody against the tag, and a labeled secondary antibody; and the like.

Furthermore, the present invention encompasses a fusion protein consisting of the polypeptide of the present invention and a heterogeneous polypeptide, obtained by carrying out the above localization method.

According to the present invention, there is provided a kit useful for carrying out the localization method of the present invention, i.e., a kit for expressing a heterogeneous polypeptide to be expressed on the cytoplasmic membrane, wherein the kit comprises the construct of the present invention for introducing into a cell (referred to as a kit for the localization method). In addition, the above kit for the localization method may be a kit further comprising a host capable of adding an O-glycan thereto as a posttranslational modification. The kit for localization method may further comprise a reagent for carrying out the localization method of the present invention by using the construct of the present invention for introducing into a cell as a host capable of adding an O-glycan thereto as a posttranslational modification. The reagent includes, for instance, a reagent for introducing a nucleic acid into a cell, ligase and a buffer therefor, a reagent for detecting a heterogeneous polypeptide to be expressed on the surface of the cytoplasmic membrane (reagent used for determination of an activity), a medium for cultivation of a host, and the like. Also, the kit of the present invention for the localization method contains an instruction manual describing the procedures for carrying out the localization method of the present invention using the kit of the present invention for localization method, a means for providing the information on the procedures, and the like.

According to the nucleic acid of the present invention, there are provided an oligonucleotide probe and a pair of primers specific to the nucleic acid. The oligonucleotide probe and the pair of primers include 1) the nucleic acid shown in SEQ ID NO: 1 or a fragment thereof, 2) a nucleic acid having the nucleotide sequence complementary to the nucleic acid or a fragment thereof, or 3) a nucleic acid capable of hybridizing to a nucleic acid having the nucleotide sequence complementary to the nucleic acid or a fragment thereof under stringent conditions. Here, the nucleic acid having a complementary nucleotide sequence is understood to be of the same meaning as an antisense nucleic acid, antisense strand, or the like.

The oligonucleotide probe of the present invention is concretely an oligonucleotide probe capable of hybridizing to a nucleic acid comprising the nucleotide sequence shown in SEQ ID NO: 1 or an antisense nucleic acid thereof under stringent conditions, wherein the oligonucleotide probe has 15 to 150 nucleotides in length. In addition, the pair of primers of the present invention are, concretely, a pair of primers consisting of an oligonucleotide capable of hybridizing to a nucleic acid consisting of the nucleotide sequence shown in SEQ ID NO: 1 under stringent conditions, wherein the oligonucleotide has 8 to 50 nucleotides in length, and another oligonucleotide capable of hybridizing to an antisense nucleic acid consisting of the nucleotide sequence shown in SEQ ID NO: 1 under stringent conditions, wherein the oligonucleotide has 8 to 50 nucleotides in length.

The term "stringent conditions" as used herein with regard to the oligonucleotide probe and the pair of primers of the present invention refers to, for instance, but is not particularly limited to, conditions of carrying out overnight incubation at a temperature ["$T_m$−25° C." of oligonucleotide probe and pair of primers] in a solution containing 6×SSC, 0.5% SDS, 5×Denhardt's, and 100 mg/mL herring sperm DNA.

As the above temperature conditions, the stringency can be increased by, for instance, having a value closer to $T_m$ value (for instance, $T_m$−24° C., $T_m$−22° C., $T_m$−20° C., and the like). The stringency can also be increased by hybridization at a greater ionic strength, for instance, under the conditions of 5×SSC, 4×SSC or the like.

Furthermore, a nucleic acid having sequence identity of at least about 80%, preferably 90% or more, and more preferably 95% or more to the antisense nucleic acid shown of SEQ ID NO: 1 can be obtained as the primer and/or probe, by washing under more stringent conditions, concretely using a buffer of a low ionic strength, for instance, 2×SSC, 1×SSC, or 0.5×SSC, and at a higher temperature, for instance, a temperature lower by 40° C., more stringently by 30° C., and still more stringently by 25° C., than the $T_m$ value of the nucleic acid used, concretely at a temperature of 37° C. or higher, more stringently 42° C. or higher, and still more stringently 45° C. or higher, depending on the $T_m$ value of the nucleic acid used.

$T_m$ of the oligonucleotide probe or primers can be calculated, for instance, by the following equation:

$$T_m=81.5-16.6(\log_{10}[Na^+])+0.41(\%\,G+C)-(600/N)$$

wherein N is a strand length of the oligonucleotide probe or primer; and % G+C is a content of guanine and cytosine residues in the oligonucleotide probe or primer.

In addition, when the strand length of the oligonucleotide probe or primer is shorter than 18 bases, $T_m$ can be deduced from a sum of a product of the contents of A+T (adenine+thymine) residues multiplied by 2° C., with a sum of a product of the contents of G+C residues multiplied by 4° C. [(A+T)×2+(G+C)×4].

The above oligonucleotide probe can be prepared by, for instance, designing on the basis of the nucleotide sequence of the nucleic acid of the present invention, and chemically synthesizing, and the like. The strand length of the above oligonucleotide probe is not particularly limited. It is preferable that the strand length is 15 nucleotides in length or more, more preferably 18 nucleotides in length or more, from the viewpoint of preventing nonspecific hybridization. One example of the oligonucleotide probe having the strand length include a probe having a nucleotide sequence of 15 continuous nucleotides in length or more in the nucleotide sequence shown in SEQ ID NO: 1 or in a sequence complementary to the nucleotide sequence, and the like.

In addition, the pair of primers of the present invention include nucleic acids having the same nucleotide sequence as those of the above oligonucleotide probe. The pair of primers can be prepared by, for instance, designing on the basis of the gene of the present invention, and chemically synthesizing the gene, and the like. The strand length of the primer is not particularly limited. For instance, the primer having a strand length of 15 to 40 nucleotides in length can be used, especially one having a strand length of 17 to 30 nucleotides in length can be suitably used. The above primer can be used for various gene amplification methods such as polymerase chain reaction (PCR) method, whereby the mucin box gene of the present invention can be detected. One example of the pair of primers having the strand length includes, for instance, a pair of primers consisting of primers each having a nucleotide sequence of continuous 15 to 40 nucleotides in the nucleotide sequence shown in SEQ ID NO: 1 or in the sequence complementary to the nucleotide sequence.

A sequence suitable for the above oligonucleotide probe and primers can be obtained using a commercially available software or the like which can anticipate the secondary structure formation on the bases of, for instance, the above Tm value, strand length and the like. The software includes OLIGO Primer Analysis Software (manufactured by TAKARA BIO INC.) or the like. One of ordinary skill in the art can select a sequence suitable for the oligonucleotide probe or primer from a portion having low homology with a known gene or a portion characteristic to SEQ ID NO: 1 by selecting a sequence having sequence identity of 30% or less, preferably 20% or less, more preferably 10% or less, still more preferably 5% or less, especially preferably 0% throughout known genes using the above software.

In addition, as the above oligonucleotide probe and pair of primers, there may be used a nucleic acid obtained by fragmenting a nucleic acid encoding a naturally occurring mucin box by an enzyme treatment such as restriction endonuclease treatment or exo-nuclease treatment, a physical treatment such as ultrasonication, or the like, and separating and purifying the resulting fragment by various nucleic acid separation methods represented by agarose gel or the like. It is desired that the nucleic acid obtained in the manner as described above is derived from a region having a sequence characteristic to the nucleic acid of the present invention.

The oligonucleotide probe and pair of primers of the present invention may have various labels suitable for the detection of the probe or the pair of primers, for instance, a fluorescent labeling, a radioactive labeling, a ligand such as biotin or digoxigenin, or the like. The oligonucleotide probe and pair of primers having the label can be used for detection of the nucleic acid of the present invention. Therefore, according to the present invention, there is provided a kit for detecting a nucleic acid encoding a polypeptide having an activity for targeting a heterogeneous polypeptide to a surface of the cytoplasmic membrane (referred to as a kit for detecting a nucleic acid).

One of the significant features of the kit of the present invention for detecting a nucleic acid resides in that the kit comprises the oligonucleotide probe and pair of primers of the present invention.

Therefore, the kit of the present invention for detecting a nucleic acid can be used for detecting a nucleic acid encoding a polypeptide having an activity for targeting a heterogeneous polypeptide to the surface of the cytoplasmic membrane, whereby the detection can be conveniently made.

The kit of the present invention for detecting a nucleic acid may further comprise various reagents for hybridization represented by a membrane for immobilizing a nucleic acid, a hybridization buffer, and the like, PCR reagents represented by a thermostable DNA polymerase, a dNTP mixture, a PCR buffer, and the like, a reagent for detection of probes or amplified DNA, a medium for proliferating a cell, a reagent for extracting a nucleic acid from a sample, and the like.

In addition, according to the present invention, there is provided a method for detecting a nucleic acid encoding a polypeptide having an activity for targeting a heterogeneous polypeptide to the surface of the cytoplasmic membrane.

One of the significant features of the method of the present invention for detecting a nucleic acid resides in that the method is carried out by the steps of: detecting with a use of the oligonucleotide probe of the present invention a hybrid therewith; and/or detecting an amplified product by a nucleic acid amplification method using the pair of primers of the present invention and a nucleic acid to be detected.

Therefore, according to the method of the present invention for detecting a nucleic acid, there is exhibited an excellent effect that a nucleic acid encoding a polypeptide having an activity for targeting a heterogeneous polypeptide to the surface of the cytoplasmic membrane can be detected. Also, the method of the present invention for detecting a nucleic acid is useful for searching of a nucleic acid encoding a protein for localizing on the surface of the cytoplasmic membrane, anticipation of protein localization on the surface of the cytoplasmic membrane from a nucleotide sequence, searching of a localization signal, and the like.

In the detection method of the present invention, the gene detection may be carried out by a hybridization method or the like using the above oligonucleotide probe. Alternatively, the gene detection may be carried out by a DNA amplification method such as PCR, using the above primers.

When the oligonucleotide probe is used, the sample used for detection includes, for instance, a sample such as a tissue section or a cultured cell, DNA or RNA immobilized on a membrane, wherein the DNA or RNA is contained in these samples, DNA or RNA extracted from these samples, and the like. From the viewpoint of the stability of the sample, DNA immobilized on a membrane or extracted DNA is preferred. When the oligonucleotide probe is used, gene detection can be carried out by the known hybridization methods or the like, as described in *Molecular Cloning: A Laboratory Manual, 3rd Ed.* (all teachings of which are incorporated herein by reference) and the like.

The conditions for the above hybridization can be appropriately determined according to the $T_m$ value of the probe used, the GC content of target DNA, and the like. For instance, the conditions described in the above *Molecular Cloning: A Laboratory Manual,* 3rd Ed. can be applied.

When the pair of primers are used, the sample used for detection includes, for instance, a sample derived from living bodies such as skin, tissue, or tissue section, or a tissue culture sample.

The sample used for detection when using the above pair of primers for instance, a solid sample such as tissue, can be used in the form of an extract or suspension. Supernatants of these samples, or samples prepared by subjecting these samples to a cytolytic treatment such as a treatment with a surfactant, and supernatants thereof can also be used. Furthermore, the sample may be subjected to a procedure for removing other components in the sample, as long as the nucleic acid to be detected is not affected.

When the detection is carried out by PCR using the above pair of primers, PCR conditions can be appropriately selected depending on the $T_m$ value of each primer in the pair of primers used, the length of the region to be amplified and detected, and the like.

When the above pair of primers is used, the detection can be made by amplifying the gene by a DNA amplification method such as PCR, and confirming the presence or absence of an amplified product for PCR. The method for confirming the presence or absence of amplification is not subject to particular limitation. The confirmation can be made by subjecting a reaction mixture for nucleic acid amplification to agarose gel electrophoresis, staining the gel with an appropriate nucleic acid staining reagent, for instance, ethidium bromide, SYBER Green I or the like, and detecting the presence or absence of the band generated from ultraviolet irradiation. The band can be detected by macroscopic observation, or the band can be detected with, for instance, a fluorescence image analyzer.

In the method of the present invention for detecting a nucleic acid, in order to increase the detection sensitivity, the detection using the above probe and the detection using the pair of primers may be used together. For instance, the detection can be carried out highly sensitively and accurately by amplifying a "nucleic acid encoding a polypeptide having an activity for targeting a heterogeneous polypeptide to the surface of the cytoplasmic membrane" existing in a trace amount in the sample by PCR using the above pair of primers, and then hybridizing the amplified product to the nucleic acid using a probe.

There can be carried out quantifying the intensity of the signal ascribed to the hybridized probe, the fluorescence intensity of the band from the product amplified using a primer, or the like, when the detection of a "nucleic acid encoding a polypeptide having an activity for targeting a heterogeneous polypeptide to the surface of the cytoplasmic membrane" is carried out by the method of the present invention for detecting a nucleic acid, to determine an expression level thereof.

Furthermore, according to the polypeptide of the present invention, there is provided an antibody or a fragment thereof capable of specifically binding to a polypeptide having an activity for targeting a heterogeneous polypeptide to the surface of the cytoplasmic membrane.

The antibody or a fragment thereof of the present invention is not particularly limited, as long as the antibody or a fragment thereof possesses an ability of specifically binding to the polypeptide of the present invention or the glycosylated polypeptide thereof, namely a polypeptide having an activity for targeting a heterogeneous polypeptide to the surface of the cytoplasmic membrane. The antibody may be any of polyclonal antibodies and monoclonal antibodies. Further, antibodies modified by known techniques or antibody derivatives, for instance, chimeric antibodies, humanized antibodies, Fv fragments, $F(ab')_2$ fragments, disulfide cross-linked Fv fragments, Fab fragments, single-chain antibodies, and the like, can also be used. The antibody of the present invention can be readily prepared by appropriately immunizing a rabbit, a mouse or the like using all or a part of the polypeptide of the present invention in accordance with the method described in, for instance, *Current Protocols in Immunology*, edited by John E. Coligan, published by John Weily & Sons, Inc., 1992. Also, an antibody can be prepared by genetic engineering means. All teachings of the literature are incorporated herein by reference. Also, there is encompassed an antibody or a fragment thereof capable of specifically binding to a partial fragment of the polypeptide.

Furthermore, the resulting antibody is purified and thereafter treated with a peptidase or the like, to give a fragment of an antibody. As use for the resulting antibody or a fragment thereof, there can be considered detection of mucin box, detection of mucin box-added protein, affinity chromatography, screening of various libraries (genomic DNA or cDNA), pharmaceuticals, diagnostic agents, reagents for researches, and the like.

Further, the antibody or a fragment thereof of the present invention may be subjected to various modifications in order to facilitate the detection by enzyme immunoassay, fluoroimmunoassay, luminescent immunoassay, or the like.

Here, it is desired that the antibody or a fragment thereof of the present invention has very high avidity against the polypeptide of the present invention or the glycosylated polypeptide thereof.

The polypeptide of the present invention or the glycosylated polypeptide thereof can be detected with a substance capable of specifically binding to the polypeptide of the present invention or the glycosylated polypeptide thereof, such as the above antibody or a fragment thereof. The present invention encompasses a method for detecting the polypeptide of the present invention or the glycosylated polypeptide thereof, i.e., the polypeptide having an activity for targeting a heterogeneous polypeptide to the surface of the cytoplasmic membrane.

One of the significant features of the method of the present invention for detecting a polypeptide or a glycosylated polypeptide thereof resides in that the method comprises detecting with a use of a substance capable of specifically binding to the polypeptide of the present invention or a glycosylated polypeptide thereof, a polypeptide or a glycosylated polypeptide thereof, capable of binding to the substance from a sample to be tested.

Therefore, according to the method of the present invention for detecting a polypeptide or a glycosylated polypeptide thereof, there is exhibited an excellent effect that a polypeptide having an activity for targeting a heterogeneous polypeptide to the surface of the cytoplasmic membrane can be detected. Also, the method of the present invention for detecting a polypeptide or a glycosylated polypeptide thereof is useful for searching of a protein localized on the surface of the cytoplasmic membrane, anticipation of a protein localized on the surface of the cytoplasmic membrane, searching of a localization signal, and the like.

In the present invention, as the sample to be tested, there can be used, for instance, a protein sample such as a cultured cell, a tissue, a membrane fraction of the cultured cell, a membrane fraction of the tissue, or a membrane to which a protein derived from the cultured cell or a protein derived from the cultured cell is immobilized.

The substance capable of specifically binding to the polypeptide of the present invention or a glycosylated polypeptide thereof includes the antibody or a fragment thereof of the present invention, a lectin specific to a mucin type sugar chain, an antibody against Tn antigen, a fragment of an antibody against the Tn antigen, an antibody against T antigen, a fragment of an antibody against the T antigen and the like.

In the detection for a specific binding of the antibody or a fragment thereof of the present invention to the polypeptide of the present invention or a glycosylated polypeptide thereof, a known method can be employed, and the detection can be made by, for instance, enzyme immunoassay, fluorescence immunoassay, or luminescence immunoassay.

When the cultured cell or tissue is used directly, the above binding can be determined using immunostaining and microscopy or flow cytometry. Furthermore, a protein sample to be tested may be subjected to electrophoresis using a polyacrylamide gel and then the above binding can be detected by Western blotting using the antibody or a fragment thereof of the present invention.

According to the method of the present invention for detecting a polypeptide or a glycosylated polypeptide thereof, a fusion protein localized by the localization method of the present invention can also be detected. For instance, in order to increase detection specificity and sensitivity, the detection can be made by previously immunoprecipitating a mucin box-added protein from the sample using a specific antibody against the desired protein or the polypeptide of the present invention or a tag sequence.

The above lectin specific to a mucin type sugar chain is one of the proteins capable of specifically recognizing an O-glycan linked to a mucin box. Concrete examples include peanut lectin (PNA), jacalin lectin, which are capable of specifically recognizing Galβ1, 3GalNAc, each representing a type 1 core structure of an O-glycan and the like. Also, an antibody or a fragment thereof against the above Tn antigen (NeuAcα2, 3Galβ1, 3GalNAcα1-Ser/Thr), and an antibody against T antigen (Galβ1, 3GalNAcα1-Ser/Thr) are antibodies against the core structure of an O-glycan, and commercially available antibodies can be used.

According to the present invention, there is provided a kit used for the method of the present invention for detecting the polypeptide of the present invention or a glycosylated polypeptide thereof, i.e., a kit for detecting a polypeptide having an activity for targeting a heterogeneous polypeptide to the surface of the cytoplasmic membrane (referred to as a kit for detecting a polypeptide). One of the features of the kit of the present invention for detecting a polypeptide resides in that the kit comprises at least one member selected from the group consisting of the antibody or a fragment thereof of the present invention, the above lectin specific to a mucin type sugar chain, the above antibody against Tn antigen, the above fragment of an antibody against the Tn antigen, the above antibody against T antigen, and the above fragment of an antibody against the T antigen.

Therefore, according to the kit of the present invention for detecting a polypeptide, there is exhibited an excellent effect that a polypeptide having an activity for targeting a heterogeneous polypeptide to the surface of the cytoplasmic membrane can be conveniently detected. Furthermore, the kit of the present invention for detecting a polypeptide can be used for detection of a heterogeneous polypeptide expressed in a form linked to the polypeptide of the present invention on the surface of the cytoplasmic membrane.

The kit of the present invention for detecting a polypeptide may further comprise a reaction buffer, a labeled secondary antibody, a color developing reagent, or the like.

According to the localization method of the present invention, when the heterogeneous polypeptide is a receptor or ligand in the transformant in which a heterogeneous polypeptide is localized on the surface of the cytoplasmic membrane, a ligand for the above receptor contained in the sample to be tested or a receptor for the above ligand can be detected by using the transformant. The method for detecting a ligand or receptor for a polypeptide is also encompassed in the present invention.

One of the significant features of the method of the present invention for detecting a ligand or receptor resides in that the method comprises contacting a cultured cell of a transformant with a substance to be tested, wherein the transformant harbors the above construct for introducing into a cell, and a heterogeneous polypeptide to be expressed is localized on the plasma membrane, and detecting the substance bound to the heterogeneous polypeptide on a surface of the cytoplasmic membrane of the cultured cell. Concrete examples include a method comprising carrying out the localization method of the present invention, for instance, carrying out the above steps (I) and (II) and then carrying out the steps (III) and (IV):

(III) contacting the obtained cultured cell with the sample to be tested; and (IV) detecting the substance bound to the heterogeneous polypeptide on a surface of the cytoplasmic membrane of the cultured cell.

In the above step (III), a transformant previously prepared may be used.

The sample to be tested in the above step (III) includes, for instance, a cell, a tissue, a membrane fraction of the cell, a membrane fraction of the tissue, a protein derived from the cell, a protein derived from the tissue and the like.

In the above step (IV), the detection of the substance bound to the heterogeneous polypeptide on the surface of the cytoplasmic membrane of the cultured cell, i.e., a ligand or receptor, can be made by, for instance, a method comprising immunostaining the expressed cell with a fluorescent-labeled antibody specific to the ligand, receptor, or the like, and detecting the fluorescence signal on the cell surface with a confocal laser fluorescence microscope; and a method comprising measuring the stained cell by flow cytometry. Also, the detection of the substance bound to the heterogeneous polypeptide on the surface of the cytoplasmic membrane of the cultured cell, i.e., a ligand or receptor, can also be carried out by a method comprising preparing a cytoplasmic membrane fraction and carrying out Western blotting with a specific antibody; and a method of directly determining the activity of the ligand or receptor.

The method of the present invention for detecting a ligand or receptor can be carried out more conveniently by using a kit for detecting a ligand or receptor for a polypeptide, comprising the transformant of the present invention. The kit is also encompassed in the present invention.

The present invention will be more specifically described by means of Examples, without intending to limit the present invention thereto. Also, unless specified otherwise, the experimental procedures were appropriately modified in accordance with the above *Molecular Cloning, Third Edition*, or the like.

EXAMPLE 1

Construction of Plasmids for Expression of Each of Rat-Derived Neutral Ceramidase, Mucin Box-Deleted Mutant, and Mucin Box-Containing Construct Vector pcDNA3.1/Myc-his(+) containing a full length rat neutral ceramidase (hereinafter referred to as CDase) gene contained in pcDNAkCD, was prepared in accordance with the method of Mitsutake et al. [*Journal of Biological Chemistry,* 276, 26249-26259 (2001)]. Concretely, plasmid pcDNAkCD was treated with restriction endonucleases KpnI and XhoI, and the fragment obtained was then subcloned into pBluescript IISK (trade name, manufactured by STRATAGENE). Thereafter, the full length neutral CDase gene was digested with KpnI and SmaI, and the product obtained was then cloned into pEGFP-N2 (trade name, manufactured by Clontech), whereby a plasmid for expression of a rat neutral CDase with GFP tag (hereinafter referred to as a "plasmid for expression of wild-type CDase") was obtained.

On the other hand, a mucin box-deleted mutant (Δmucin) was constructed by ligating an N-terminal fragment (Met1-Lys42) (SEQ ID NO: 11) and a C-terminal fragment (Asn79-Thr761) (SEQ ID NO: 12). First, PCR was carried out using a 5'-primer 1 having KpnI recognition site (SEQ ID NO: 13, 5'-AGGGTACCGAAATGGCAAAGCGAACCTTCTCC-3') and a 3'-primer 2 (SEQ ID NO: 14, 5'-ACACCAATGTAGTAGCCACTGAAGTTTTTGTGGTTTTCGATGGTCCC-3'), to give a nucleic acid encoding the above N-terminal fragment. PCR was also carried out using a 5'-primer 3 (SEQ ID NO: 15, 5'-GGGACCATCGAAAACCACAAAAACTTCAGTGGCTACTACATTGGTGT-3') and a 3'-primer 4 having XhoI recognition site (SEQ ID NO: 16, 5'-GCCGCTCGAGAGTAGTGACAATTTCAAAAGGGGAAGA-3') to give a nucleic acid encoding the above C-terminal fragment. Each of the resulting products was extended using Pyrobest DNA polymerase, and subcloned into vector pcDNA3.1/Myc-his(+) (trade name, manufactured by Invitrogen) to give a plasmid for expression of Δmucin.

In addition, a GFP in which both the mucin box and the secretion signal sequence were added (S-M-GFP) and a GFP in which only the secretion signal was added (S-GFP) were designed as described below using two N-terminal fragments of rat neutral CDase, i.e., Met1-Gln78 (SEQ ID NO: 17) and Met1-Lys42 (SEQ ID NO: 11).

PCR was carried out using a pair of primers consisting of a 5'-primer 5 having KpnI recognition site (SEQ ID NO: 18, 5'-AGGGTACCGAAATGGCAAAGCGAACCTTCTCC-3') and a 3'-primer 6 having BamHI recognition site (SEQ ID NO: 19, 5'-CCACGGATCCCCTGAGAGGGAGGGAGGTCTGG-3'), and using the 5'-primer 5 (SEQ ID NO: 18) and a 3'-primer 7 having BamHI recognition site (SEQ ID NO: 20, 5'-TTCCGGATCCCTTTGTGGTTTTCGATGGTCCC-3'), to give each of a fragment encoding the above Met1-Gln78 (SEQ ID NO: 17) and a fragment encoding Met1-Lys42 (SEQ ID NO: 11).

Each of the resulting fragments was subcloned to pEGFP-N2, to give a plasmid for expression of S-M-GFP and a plasmid for expression of S-GFP.

The nucleotide sequence of each of the resulting plasmids was confirmed by using a DNA sequencer (trade name: Model 377, manufactured by Applied Biosystems). The schematic views of the plasmids are shown in FIG. 2. The CDase activity was determined in accordance with the method described in *Journal of Biological Chemistry,* 275, 3462-3468 (2000) with C12-NBD-Cer as a substrate.

EXAMPLE 2

Analysis for Expression of Mucin Box-Deleted Mutant (Δmucin)

Each of the plasmid for expression of Δmucin and the plasmid for expression of wild-type CDase obtained in Example 1 was transfected to HEK293 cells from human embryonic kidney using LipofectAMINE Plus (trade name, manufactured by Invitrogen). HEK293 cells from the human embryonic kidney were cultured by the method described in *Journal of Biological Chemistry,* 276, 26249-26259 (2001). Concretely, the cultivation was carried out in a Dulbecco's modified Eagle medium containing 10% (v/v) fetal bovine serum and 60 μg/ml kanamycin in an incubator at a concentration of 5% $CO_2$.

After 18 hours from the transfection, the cells were harvested, and the medium was replaced with serum-free Opti-MEM (trade name, manufactured by Invitrogen). Thereafter, the medium was added to a 24-well plate at 0.5 ml per well, and the cultivation was continued for additional 24 hours. The culture supernatant was then collected and centrifuged at 15000 rotations for 5 minutes.

A 1/10 (v/v) volume of 200 mM Tris-HCl, pH 7.5, containing 1% Triton™ X-100 and a 3.3 μg/ml protease inhibitor cocktail (leupeptin, pepstatin, chymostatin) was added to the supernatant obtained by the centrifugation. The solution obtained was used as the culture supernatant. The cells attached to the culture plate were washed with PBS and then lysed by the addition of 10 mM Tris-HCl (pH 7.5) containing 0.5% (v/v) Triton™ X-100 and 3.3 μg/ml protease inhibitor cocktail (leupeptin, pepstatin, chymostatin). The cell lysate obtained was collected by a pipette, and used in the following experiment.

Figure 3:
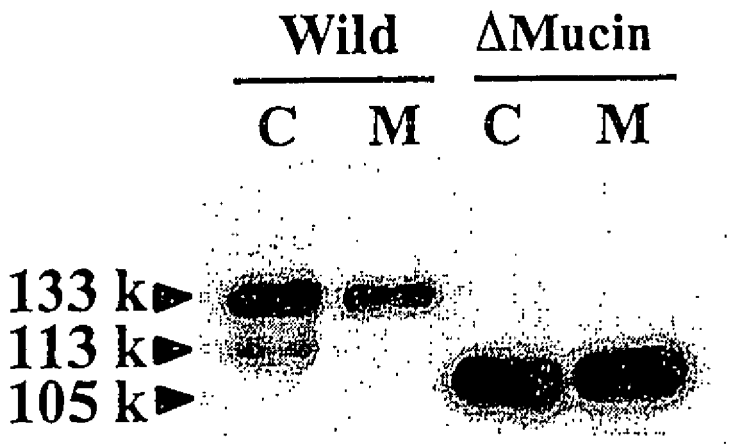
FIG. 3 shows the results of Western blotting of the ceramidase expressed in HEK293 cell, wherein C represents a cell lysate and M represents a conditioned medium culture supernatant.

The culture supernatant and the cell lysate were subjected to SDS-PAGE using 7.5% (w/v) gel in accordance with the method of Laemmli (*Nature* 227, 680-685, all teachings of which are incorporated herein by reference), followed by Western blotting. The transfer onto PVDF membrane was carried out using TransBlot SD (trade name, manufactured by Bio-Rad). The transferred PVDF membrane was blocked for 1 hour in T-TBS [Tris-buffered saline (TBS) containing 0.1% (v/v) Tween 20] containing 3% (w/v) skim milk, and the blocked membrane was then incubated with anti-Myc antibody (manufactured by Invitrogen), which was a primary antibody, at 4° C. for 1 day. Thereafter, the membrane was washed with T-TBS above, and incubated with a horseradish peroxidase (HRP)-labeled secondary antibody (anti-mouse IgG antibody, manufactured by nacalai tesque) for 2 hours. After the membrane was washed with T-TBS, the membrane was subjected to chemiluminescence with ECL-plus (trade name, manufactured by Amersham-Pharmacia). The resulting luminescent signal was analyzed by using STORM (trade name, manufactured by Amersham-Pharmacia). The results are shown in FIG. 3. In the figure, C represents the cell lysate and M represents the culture supernatant.

As shown in FIG. 3, in the case of the wild-type CDase, as a result of Western blotting, a 133-kDa band and a 113-kDa band were detected for the cell lysate, and a 133-kDa band was detected in the culture supernatant. These molecular species are considered to have undergone modification by glycosylation in Golgi apparatus and endoplasmic reticulum, respectively.

On the other hand, in the case of Δmucin, an about 105-kDa band was detected in both the cell lysate and the culture supernatant.

EXAMPLE 3

Analysis of O-Glycosylation of Δmucin

Figure 4:
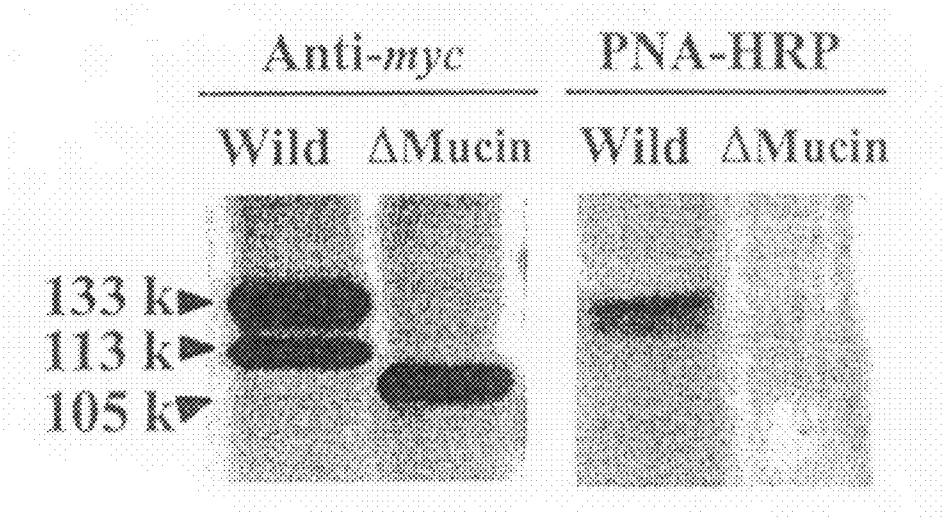
FIG. 4 shows the analytical results of Western blotting of the O-glycosylation of each of the wild-type ceramidase and the mucin box-deleted mutant.

CDase was immunoprecipitated from the cell lysate of HEK293 cells prepared in Example 2, in which Δmucin or wild-type CDase was expressed, by using an anti-CDase antibody. A 100-fold dilution of anti-CDase was coupled with 10 μl of protein A-agarose (trade name, manufactured by SANTA CRUZ) in 100 μl of a reaction buffer (10 mM Tris-HCl, pH 7.5, containing 150 mM NaCl, 1% (v/v) Triton™ X-100 and 0.1% (w/v) BSA) at 4° C. for 2 hours. The product obtained was washed five times with the above reaction buffer. Thereafter, this product was mixed with a CDase sample, obtained by previously heating at 100° C. for 5 minutes in SDS sample buffer [20 mM Tris-HCl, pH 7.5, containing 1% (w/v) SDS and 1% (v/v) 2-mercaptoethanol], and incubated at 4° C. for 18 hours with gentle stirring. Subsequently, the immunoprecipitate was sedimented by centrifugation, washed five times with the above reaction buffer, suspended in 20 μl of the SDS sample buffer, and heated at 100° C. for 5 minutes. The resulting product was subjected to SDS-PAGE and Western blotting as described in Example 2. The PVDF membrane was stained with an anti-Myc antibody or an HRP-labeled PNA lectin. The results are shown in FIG. 4. PNA (peanut agglutinin) lectin is a lectin capable of specifically recognizing and binding to the Galβ1,3GalNAc sequence of O-glycan.

As shown in FIG. 4, in the case of the wild-type CDase, the 130-kDa band, but not the 113-kDa band, was stained with PNA lectin. On the other hand, in the case of Δmucin, the lectin-stained band was not detected. Therefore, it could be seen that the mucin box portion was modified by O-glycan in the Golgi apparatus of the cell, and that Δmucin certainly lacked the O-glycosylation site.

EXAMPLE 4

Figure 5:
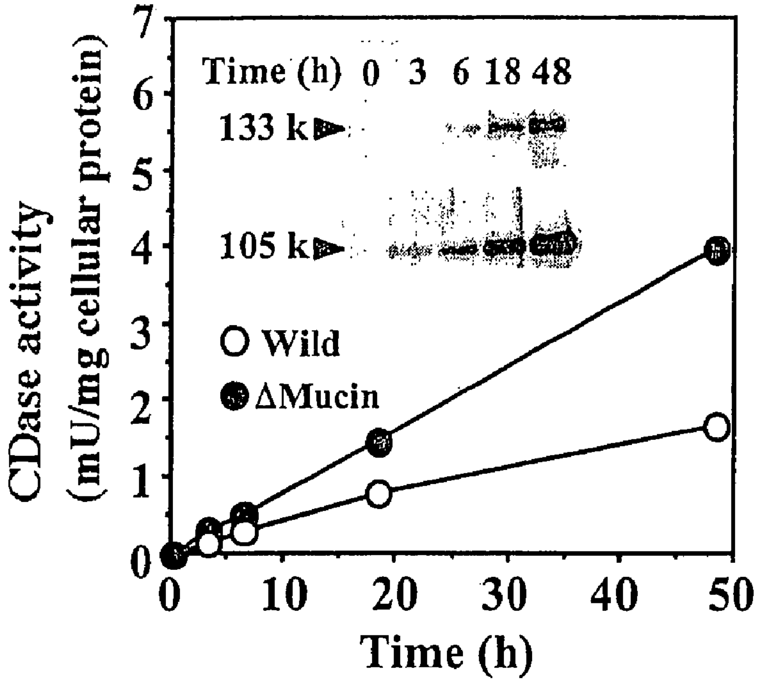
FIG. 5 shows the changes with the passage of time in the extracellular secretion of each of the wild-type ceramidase and the mucin box-deleted mutant.

Comparison of Amounts of Extracellular Secretion of Δmucin and Wild-Type CDase The CDase activity in the culture supernatant was compared with the passage of time. The results are shown in FIG. 5. At the same time, Western blotting analysis of the CDase in the supernatant was carried out. As a result, both the 130-kDa mature-type wild-type CDase and 105-kDa Δmucin were secreted extracellularly.

Figure 6:
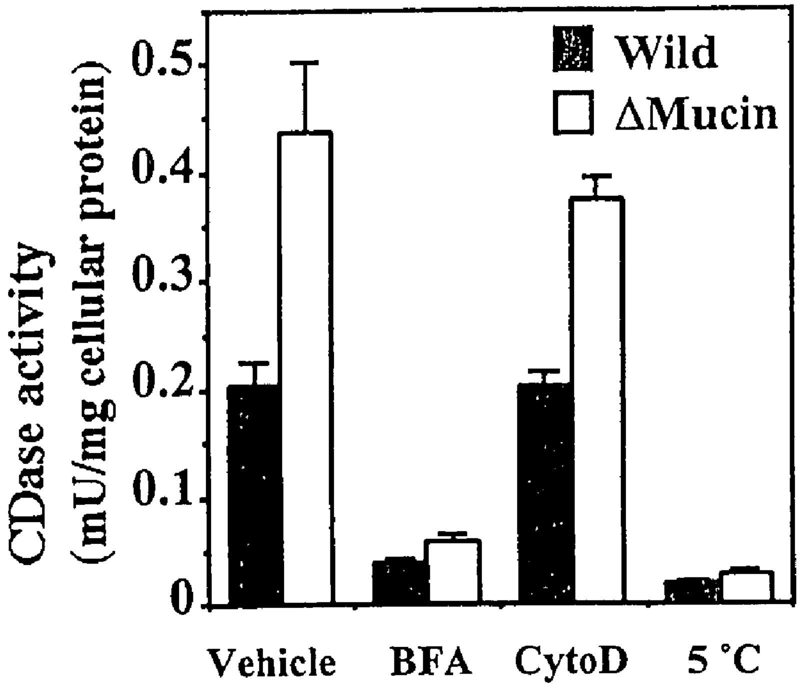
FIG. 6 shows the effects of brefeldin A (BFA), cytochalasin D (CytoD), and temperature on the secretion of ceramidase.

After 18 hours from the introduction of the expression plasmid, the cells were transferred to DMEM medium containing 10% (v/v) fetal bovine serum, previously supplemented with 10 μg/ml brefeldin A or 5 μM cytochalasin D, which was an inhibitor, and the cells were cultured at 37° C. for 1 hour. Thereafter, the cells were transferred to Opti-MEM medium (trade name, manufactured by Invitrogen) containing the same inhibitor, and cultured for additional 3 hours. In order to evaluate the influence of cultivation temperature, the transfected cells were cultured in inhibitor-free Opti-MEM medium (trade name, manufactured by Invitrogen) at 5° C. for 3 hours. The results for the determination of CDase activity in these culture supernatants are shown in FIG. 6. Although the extracellular secretion of both mature-type wild-type CDase and 105-kDa Δmucin was inhibited by brefeldin A and the low-temperature cultivation, it was not inhibited by cytochalasin D. It was thus found that CDase was processed and secreted via the classical route through the endoplasmic reticulum/Golgi apparatus regardless of the presence or absence of the mucin box.

EXAMPLE 5

Targeting of Neutral CDase to Cell Surface by Mucin Box

The plasmid for expression of GFP-tagged neutral CDase obtained in Example 1 was introduced into HEK293 cells from human embryonic kidney to express GFP-tagged neutral CDase. Thereafter, the cells were fixed and then observed for fluorescent signals of GFP using a confocal laser fluorescence microscope. In other words, the plasmid-introduced cells were cultured on a cover glass, and thereafter the cells were fixed in PBS containing 3% glutaraldehyde for 15 minutes.

The above cells were examined with a confocal laser fluorescence microscope (trade name: Digital Eclipse C1, manufactured by NIKON). The results are shown in Panel A of FIG. 7, wherein the arrow represents the expression of CDase in the cytoplasmic membrane and the arrowhead represents the expression in the endoplasmic reticulum/Golgi apparatus.

Figure 7:
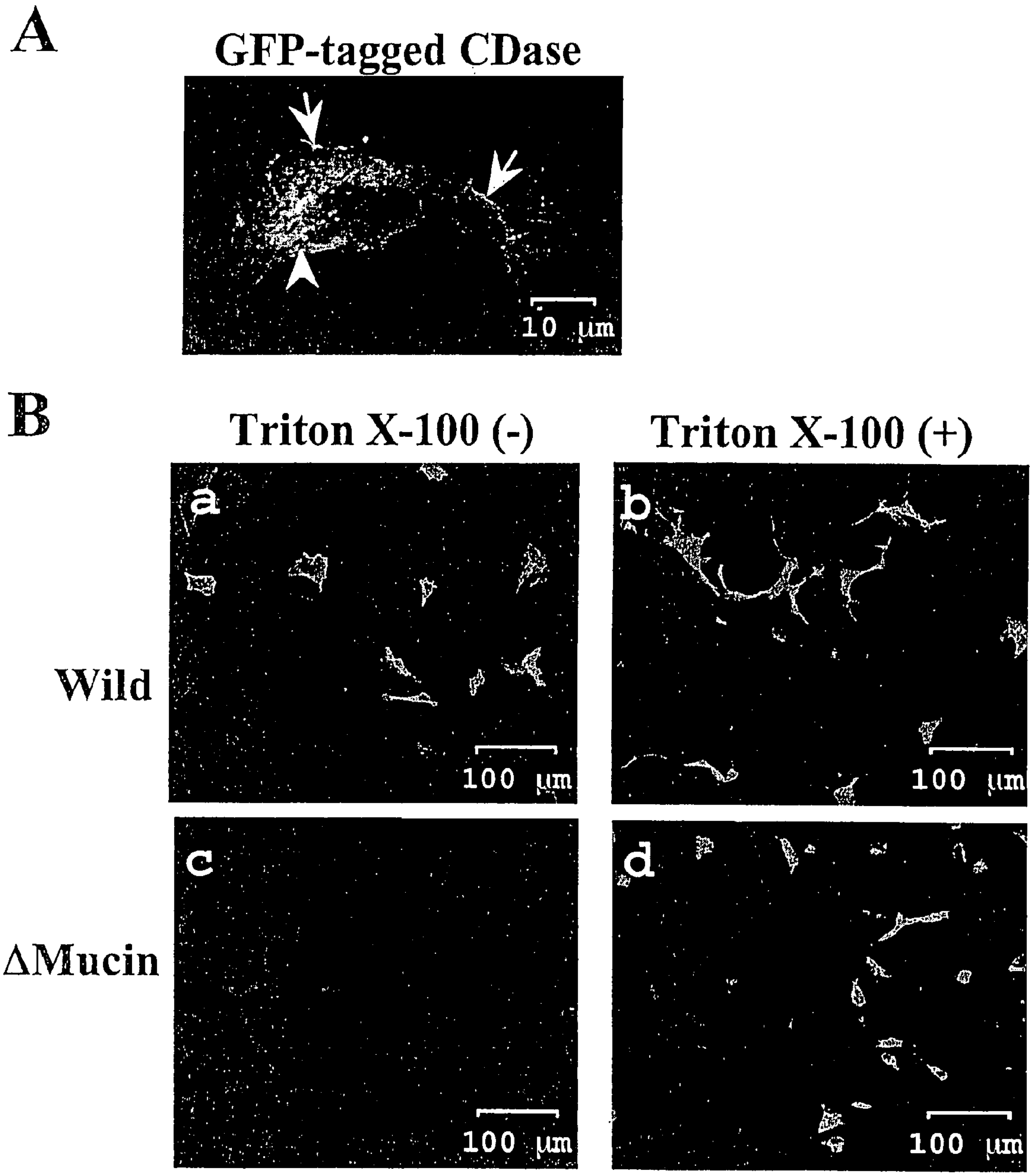
FIG. 7 is a diagram showing the examination results of expression manners of the wild-type ceramidase and the mucin box-deleted mutant. Panel A shows the observational results of expression of GFP-tagged neutral ceramidase in HEK293 cell under direct confocal laser fluorescence microscope. Panel B shows the results of immunostaining with an anti-myc antibody of expression of the wild-type ceramidase and the mucin box-deleted mutant in HEK293 cell and expression on the surface of the cytoplasmic membrane.

As shown in Panel A of FIG. 7, the CDase having its C-terminal tagged with GFP (GFP-tagged CDase) was expressed not only in the endoplasmic reticulum/Golgi apparatus but also in the plasma membrane.

Next, the cells expressing the wild-type CDase with its C-terminal tagged with myc and the cells expressing Δmucin, obtained in Example 1, were washed with PBS and with PBS containing 50 mM ammonium chloride. Also, a treatment of permeabilizing the cells with PBS containing 0.1% Triton™ X-100 was carried out, as occasion demands. Blocking was carried out for 15 minutes in PBS containing 5% (w/v) skim milk (blocking solution), and the cells on the slide glass were incubated with a primary antibody, previously 1000-fold diluted with the blocking solution, at 4° C. for 1 day, thereafter incubated with a Cy3-labeled secondary antibody at room temperature for 2 hours, and observed by immunostaining with an anti-myc antibody. The results are shown in Panel B of FIG. 7. In the figure, "a" and "b" represent HEK293 cells expressing wild-type CDase and "c" and "d" represent HEK293 cells expressing Δmucin. The treatment for permeability with Triton™ X-100 was carried out for "b" and "d," but not for "a" and "c".

As a result, as shown in Panel B of FIG. 7, a fluorescent signal of CDase on the cell surface was far more intensive with the wild-type CDase than that of Δmucin without the treatment for permeability ("a" and "c"), whereas there was little difference in signal intensity between the two molecular species with the treatment for permeability ("b" and "d").

EXAMPLE 6

Targeting of Neutral CDase to Cell Surface by Mucin Box

The wild-type CDase having its C-terminal tagged with myc and Δmucin were expressed in HEK293 cells from human embryonic kidney and Chinese hamster ovary cells expressing polyoma LT antigen (CHOP) cells and analyzed by flow cytometry.

The Chinese hamster ovary cells expressing polyoma LT antigen (CHOP) were cultured by the method described in *Journal of Biological Chemistry,* 276, 26249-26259 (2001) (all teachings of which are incorporated herein by reference).

In other words, the plasmid for expression of wild-type CDase, the plasmid for expression of Δmucin, or an empty vector (mock) was introduced into $3\times10^5$ cells, and the cells were cultured at 37° C. for 24 hours. The cells were harvested, and thereafter the harvested cells were incubated with 100 µl of an anti-myc antibody, which had been diluted 1000-folds with PBS containing 50% (v/v) FBS, on ice for 1.5 hours. The product obtained was washed twice with PBS and then incubated with 100 µl of Cy3-labeled secondary antibody (Cy3-anti-mouse IgG antibody), which had been diluted with PBS containing 50% (v/v) FBS, on ice for 1 hour. Subsequently, the resulting product was analyzed by flow cytometry (trade name: EPICS XL System-IC, manufactured by Beckman Collter). The results are shown in Panel A and Panel B of FIG. 8. Panel A shows the results for HEK293 cells and Panel B shows the results for CHOP cells.

Figure 8:
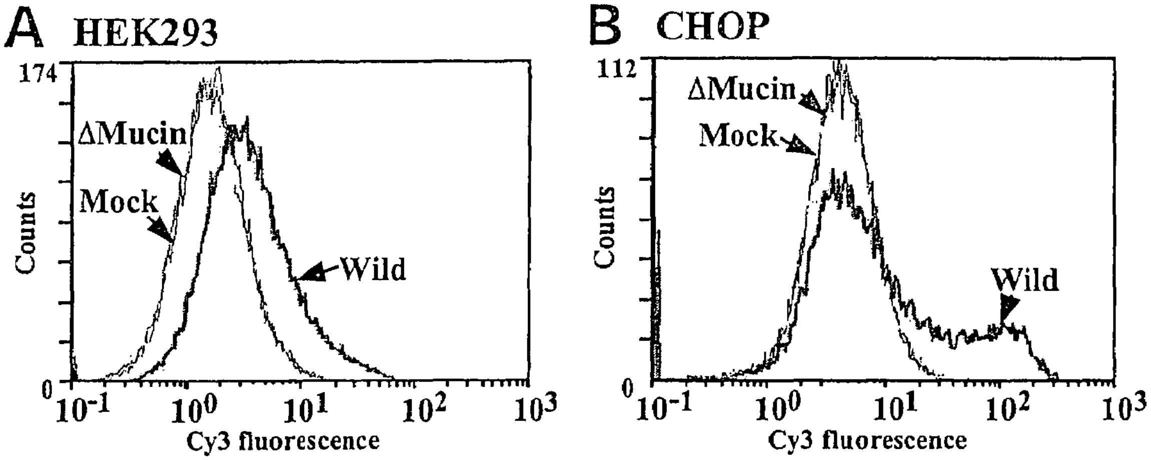
FIG. 8 shows the results from the flow cytometric analysis of a cell expressing each of the wild-type ceramidase and the mucin box-deleted mutant. Panel A shows the results of HEK293 cell and Panel B shows the results of CHOP cell.

As shown in Panel A and Panel B of FIG. 8, the wild-type CDase was expressed on the surface of the plasma membrane for both HEK293 cells and CHOP cells, whereas Δmucin was not expressed.

EXAMPLE 7

Inhibitory Effect of Mucin on Expression of CDase on Surface of Plasma Membrane The plasmid for expression of GFP-tagged neutral CDase obtained in Example 1 was introduced into $3\times10^5$ HEK293 cells from human embryonic kidney; after 4 hours, the cells were transferred to DMEM medium containing 10% (v/v) fetal bovine serum, containing 0.9 mg/ml porcine gastric mucin (Sigma), and cultured at 37° C. for 18 hours. For control, the cells cultured in a porcine gastric mucin-free medium were furnished. After the cultivation, the cells were harvested and incubated with an anti-GFP antibody in the same manner as in Example 6. Next, the product obtained was incubated with Cy3-labeled secondary antibody (Cy3-anti-rabbit IgG antibody) at 4° C. Thereafter, the product was analyzed by using flow cytometry (trade name: EPICS XL System-IC, manufactured by Beckman Collter). The results are shown in FIG. 9.

Figure 9:
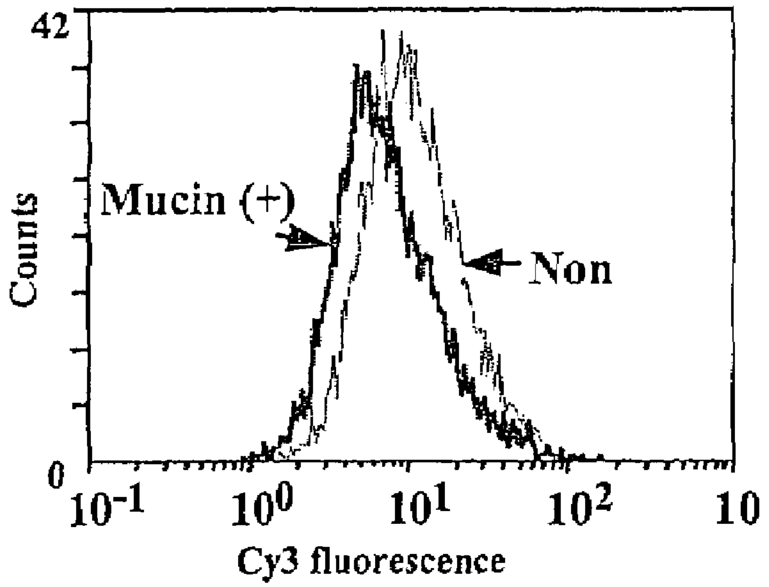
FIG. 9 shows the results from the flow cytometric analysis showing of an inhibitory effect of the mucin addition toward expression of the GFP-tagged neutral ceramidase on the surface of HEK293 cell.

As shown in FIG. 9, the expression of GFP-tagged neutral CDase on the surface of the cytoplasmic membrane was remarkably suppressed when porcine gastric mucin was added. Hence, the distribution of CDase to the surface layer of the plasma membrane of HEK293 cells was shown to be inhibited by mucin.

EXAMPLE 8

Intracellular Localization of Mucin Box-Fused GFP

The plasmid for expression of the mucin box-fused GFP prepared in Example 1 was introduced into HEK293 cells from human embryonic kidney to analyze the expressed site. A plasmid comprising the sequence encoding GFP (pEGFP-N2), a plasmid for expressing S-GFP, or a plasmid for expressing S-M-GFP was introduced into HEK293 cells in the same manner as Example 2, and the cells were cultured. Thereafter, the cells were harvested, and subjected to Western blotting using an anti-GFP antibody. The results are shown in Panel A of FIG. 10. In the figure, lane 1 shows GFP, lane 2 S-GFP, and lane 3 S-M-GFP.

Figure 10:
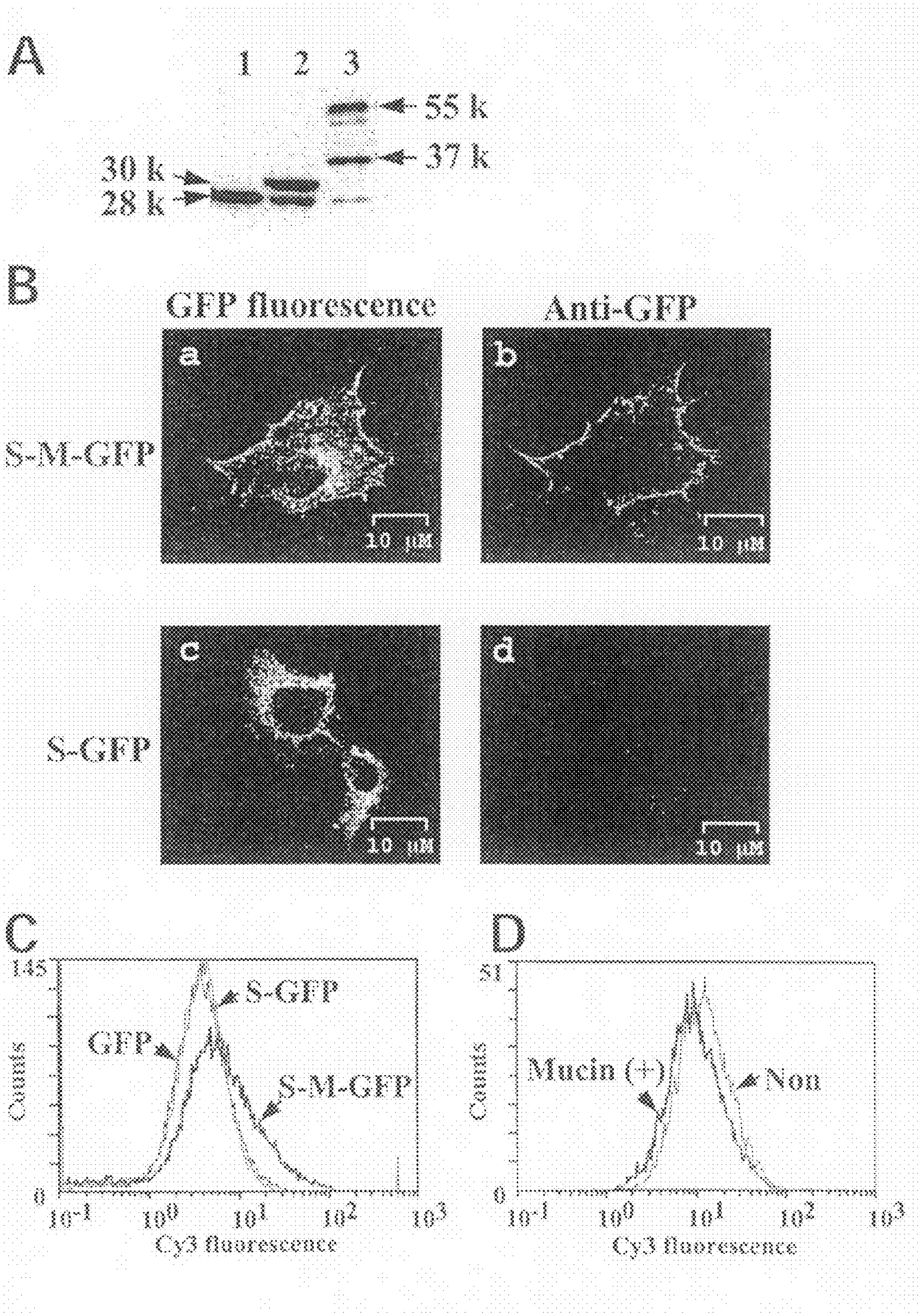
FIG. 10 shows the results of expression manners of GFP, S-GFP, and S-M-GFP and the effects of mucin thereon. Panel A shows the analytical results of Western blotting of expression of each of GFP, S-GFP, and S-M-GFP in HEK293 cell, wherein Lane 1 shows GFP, Lane 2 S-GFP, and Lane 3 S-M-GFP. Panel B shows the observational results with a fluorescence microscope after immunostaining of each of S-GFP and S-M-GFP expression in HEK293 cell. Panel C shows the results from the flow cytometric analysis showing the expression of each of GFP, S-GFP, and S-M-GFP on the surface of HEK293 cell. Panel D shows the results from the flow cytometric analysis showing the inhibitory effect by the mucin addition on the S-M-GFP expression on the surface of HEK293 cell.

As shown in Panel A of FIG. 10, mainly a 37 kDa band and a 55 kDa band were observed in the lysate of HEK293 cells in which S-M-GFP was expressed. The above 55 kDa band became low-molecular and secreted extracellularly by the addition of benzyl-GalNAc to the medium, whereas the 37 kDa band remained unchanged.

Next, the mucin box-added GFP-expressing cells were stained with an anti-GFP antibody, and thereafter observed with a confocal laser fluorescence microscope. The results are shown in Panel B of FIG. 10, wherein the panels "a" and "c" show the observation results by fluorescence of GFP (indicated as "GFP fluorescence" in the figure), and the panels "b" and "d" show the results of staining with an anti-GFP antibody (referred to as "Anti-GFP" in the figure). Also, the panels "a" and "b" of Panel B show expression of S-M-GFP, and the panels "c" and "d" show expression of S-GFP.

As shown in the panel "b" of Panel B of FIG. 10, from the results of staining with an anti-GFP antibody, S-M-GFP, which was added with both the mucin box and the secretion signal, was distributed on the surface of HEK293 cells. On the other hand, as shown in the panel "d" of Panel B of FIG. 10, S-GFP, which was added with only the secretion signal, was not expressed on the cell surface. Also, as shown in the panels "a" and "c" of Panel B of FIG. 10, from the observation results of the fluorescent signal of GFP, expression of S-GFP and expression of S-M-GFP were of the same level in the cells.

Next, expression of mucin box-fused GFP was analyzed by flow cytometry in the same manner as described above. In other words, the plasmid for expression of each of GFP, S-GFP, and S-M-GFP was introduced into $3\times10^5$ cells of HEK293 cells, and the cells were cultured for 24 hours. Thereafter, the cells were harvested, and the cells were stained with an anti-GFP antibody and a Cy3-labeled anti-rabbit IgG antibody and analyzed by flow cytometry. The results are shown in Panel C of FIG. 10.

As shown in Panel C of FIG. 10, the signal of S-M-GFP on the surface of HEK293 cells was far more intensive than that of S-GFP.

Also, the expression of S-M-GFP in the presence of porcine gastric mucin was examined in the same manner as in Example 7. The results are shown in Panel D of FIG. 10.

As shown in Panel D of FIG. 10, the expression of S-M-GFP on the surface of the cells was remarkably suppressed.

It was seen from these results that the mucin box per se which had undergone modification by O-glycan had an activity as a signal for localizing a protein on the surface of the cytoplasmic membrane.

EXAMPLE 9

Mucin Box of Neutral CDase from Mouse Organ and Serum

A membrane fraction was prepared from each of the mouse liver and kidney in accordance with the method described in *Journal of Biological Chemistry,* 275, 3462-3468 (2000) (all teachings of which are incorporated herein by reference), and the neutral CDase was solubilized by freeze-thawing. CDase activities for each of the solubilized fraction and the insoluble fraction of each organ were determined. The results are shown in Panel A of FIG. 11.

Figure 11A:
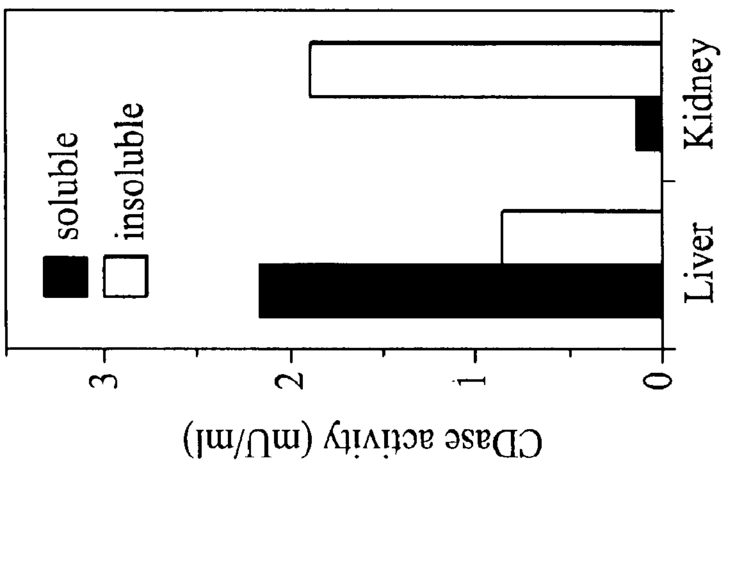
FIG. 11 shows the results of the neutral ceramidase assay in a membrane fraction and a soluble fraction for each of the mouse liver and kidney. Panel A shows the results of the neutral CDase activity in the membrane fraction and the soluble fraction of each of the mouse liver and kidney. The activity values are given as an average of two measurements. Panel B shows the analytical results of Western blotting for each of the membrane fraction (insoluble fraction) and the soluble fraction of the mouse liver, neutral CDase in the soluble fraction of the mouse kidney, and neutral CDase in serum, using an anti-neutral CDase antibody and an HRP-labeled PNA lectin of the neutral CDase.
Figure 11B:
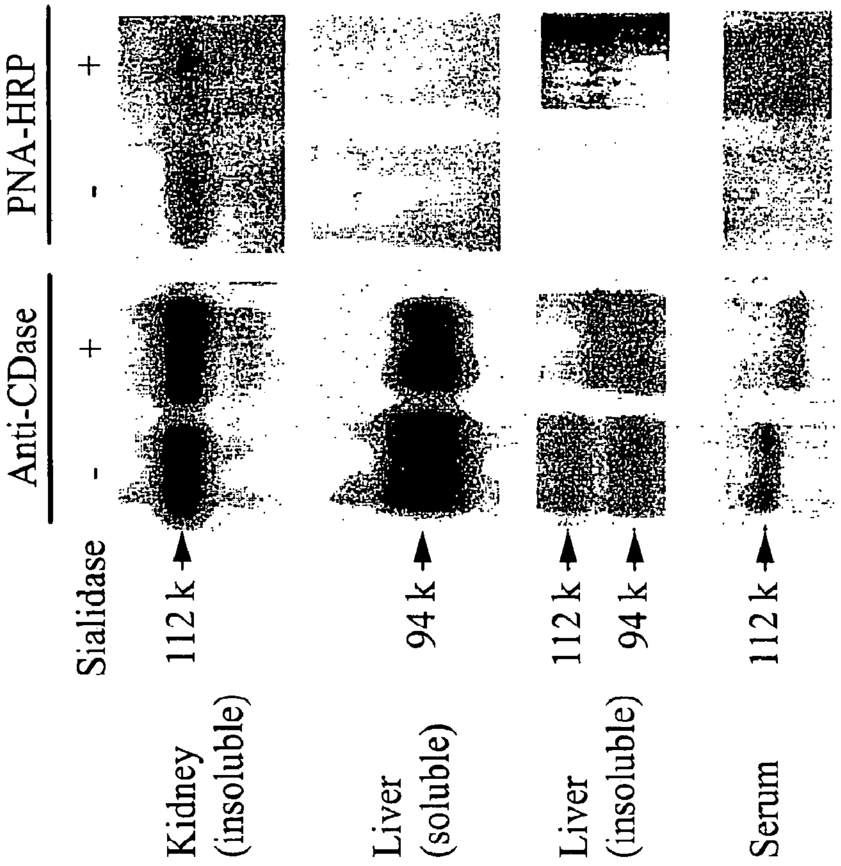

As shown in Panel A of FIG. 11, as a result of freeze-thawing, 72% of the total neutral CDase activity was found in the soluble fraction in the mouse liver, whereas 90% or more was found in the insoluble fraction in the mouse kidney.

The neutral CDase was immunoprecipitated from each of the fractions in the same manner as in Example 3, and thereafter analyzed by Western blotting using an anti-neutral CDase antibody, or lectin blotting using an HRP-labeled PNA lectin. In addition, each sample was digested at 37° C. for 18 hours with 5 mU *Vibrio cholerae* sialidase in a 500 mM acetate buffer (pH 5.0) containing 5 mM $CaCl_2$ and 0.1% (v/v) Triton™ X-100. The results are shown in Panel B of FIG. 11.

As shown in Panel B of FIG. 11, it was clarified from the results of Western blotting using an anti-neutral CDase antibody that the neutral CDase in the insoluble fraction of the kidney was a 112-kDa protein molecule, and that the enzyme in the soluble fraction of the liver was a 94-kDa molecule. Also, a 112-kDa CDase was detected in the insoluble fraction of the liver. Each of these 112-kDa CDases of the kidney and the liver was stained with PNA lectin, but the 94-kDa CDase was not. In other words, it was seen that only the CDase collected in the insoluble fraction had undergone modification by an O-glycan.

In addition, N-terminal amino acid analysis for each CDase was performed. As a result, the 94-kDa CDase was found to lack mucin box. However, it appears that there is a slight difference in O-glycosylation structures between the kidney CDase and the liver enzyme.

The liver enzyme had its molecular weight significantly changed by sialidase digestion, so that response to PNA lectin is increased, whereas the sialidase digestion was not as significantly affected in the case of the kidney CDase. Furthermore, a 112-kDa CDase stained with PNA lectin was also detected in mouse serum. This molecule is considered to be originated from the liver because its behavior to sialidase is the same as that of the enzyme in the insoluble fraction of the liver.

These results show that the modification of the neutral CDase by an O-glycan is carried out tissue-specifically, so that the localization in the plasma membrane of the enzyme is significantly affected.

EXAMPLE 10

Kit for Expression on Surface of Cytoplasmic Membrane by Mucin Box Addition

An expression plasmid was constructed so that the gene encoding the desired protein can be inserted between the sequence encoding the mucin box of the plasmid for expression of mucin box-fused GFP constructed in Example 1 and a sequence encoding GFP.

Concretely, the sequence encoding a desired protein was located downstream of the secretion signal and the mucin box sequence, and the sequence encoding GFP was located further downstream thereof. A kit for expressing the protein on the surface of the cytoplasmic membrane comprising the expression plasmid designed as described above, an anti-GFP antibody, a reagent for transfection into animal cells, cells for expression, e.g., HEK293 cells from human embryonic kidney, and an instruction manual, was constructed. In other words, a sequence encoding the secretion signal of the rat neutral CDase and a sequence encoding the mucin box sequence were prepared as described below.

PCR was carried out using a primer pair consisting of 5'-primer 5 having KpnI recognition site (SEQ ID NO: 18, 5'-AGGGTACCGAAATGGCAAAGCGAACCTTCTCC-3') and 3'-primer 6 having BamHI recognition site (SEQ ID NO: 19, 5'-CCACGGATCCCCTGAGAGGGAGGGAG-GTCTGG-3'), to prepare a fragment encoding a secretion signal sequence of the rat neutral CDase and a mucin box sequence, namely the amino acid sequence Met1-Gln78 shown in SEQ ID NO: 17. The resulting fragment was subcloned between the KpnI recognition site and the BamHI recognition site in the multi-cloning site of the vector pEGFP-N2. As described above, an expression plasmid having a nucleotide sequence encoding secretion signal and mucin box sequences downstream of the cytomegalovirus promoter, and also having a sequence encoding GFP downstream of the nucleotide sequence can be constructed. As to the resulting construct, the nucleotide sequence was determined using a DNA sequencer (trade name: Model 377, manufactured by Applied Biosystems).

By operably linking a nucleic acid encoding the desired polypeptide downstream the sequence encoding the mucin box of the resulting expression plasmid, an expression plasmid for expressing the desired polypeptide on the surface of the cytoplasmic membrane can be constructed.

According to the expression plasmid, expression of the desired polypeptide can be observed on the surface of the cytoplasmic membrane by using an anti-GFP antibody or utilizing directly a fluorescent signal from GFP.

EXAMPLE 11

Construction of Kit Used for Detecting Nucleic Acid Encoding Polypeptide Having Activity for Targeting Heterogeneous Polypeptide to Surface of Cytoplasmic Membrane An oligonucleotide probe was prepared on the basis of the nucleotide sequence shown in SEQ ID NO: 1, and primers 5 and 6 shown in SEQ ID NOs: 18 and 19, respectively, were prepared to construct the kit used for detecting a nucleic acid encoding a polypeptide having activity for targeting a heterogeneous polypeptide to the surface of the cytoplasmic membrane as described below.

Constitution of Kit (100 Runs of PCR)

| | |
|---|---|
| Primer 5 (20 pmol/μl) | 110 μl |
| Primer 6 (20 pmol/μl) | 110 μl |
| 10 × PCR Buffer | 1 ml |
| TaKaRa Taq (5 U/μl) | 50 μl |
| dNTP Mixture (2.5 mM each) | 0.8 ml |
| FITC Targeting Probe (5 pmol/μl) | 100 μl |

A nucleic acid encoding a polypeptide having an activity for targeting from the cells prepared in Example 2 to the surface of the cytoplasmic membrane could be detected by using the above kit.

EXAMPLE 12

Construction of Kit Used for Detecting Polypeptide Having Activity for Targeting Heterogeneous Peptide to Surface of Cytoplasmic Membrane Goats, rabbits, rats, mice, and other animals were immunized with a polypeptide having the amino acid sequence shown in SEQ ID NO: 2, or with the same polypeptide but modified with O-glycan, prepared by introducing an expression vector comprising the nucleotide sequence shown in SEQ ID NO: 1 into animal cells, as an antigen, to produce an anti-mucin box antibody. The following kit for detecting a polypeptide having activity for targeting a heterogeneous peptide to the surface of the cytoplasmic membrane was constructed.

Constitution of Kit (100 Runs of PCR)

| | |
|---|---|
| Anti-Mucin Box Mouse Monoclonal Antibody | 1 ml × 1 |
| FITC-Targeted Goat Anti-Mouse (IgG + IgA + IgM Antibody) | 1 ml × 1 |
| Dilution Solution | 10 ml × 1 |
| Blocking Solution | 10 ml × 1 |

An experiment was conducted in the same manner as in Example 5 using the above kit, and a polypeptide having activity for targeting to the surface of the cytoplasmic membrane could be detected.

By using this kit, the expression of the desired protein on the surface of the cytoplasmic membrane, which was expressed as a fusion protein with the mucin box can be easily confirmed. Furthermore, a ligand or receptor interacting with the desired protein expressed on the surface of the cytoplasmic membrane can be conveniently screened in the same manner as in the anti-GFP antibody by using this kit.

EXAMPLE 13

(1) Construction of Expression Plasmid and its Introduction into Cells

Expression of each of the SCDase from *Shewanella alga* G8 described in *Journal of Biological Chemistry,* 277, 17300-17307 (2002) (all teachings of which are incorporated herein by reference), the SMase from *Pseudoinonas* sp. TK4 described in *Journal of Bacteriology,* 184, 540-546 (2002) (all teachings of which are incorporated herein by reference), and the EGCase from *Rhodococcus* sp. M777 described in *Journal of Biological Chemistry,* 272, 19846-19850 (1997) (all teachings of which are incorporated herein by reference) was studied by using the method of the present invention. First, PCR was carried out with pcDNA3.1/Myc-his(+), prepared in Example 1, containing the full length CDase gene, as template DNA, using a sense primer RCS1 (SEQ ID NO: 24, 5'-AGGGTACCGAAATGGCAAAGCGAACCTTCTCC-3'), having KpnI recognition site added to a sequence corresponding to the N-terminal of rat CDase, and an antisense primer L-kCDMbox-SCD-2 (SEQ ID NO: 25, 5'-CGCCTGGGTGGTTTGCGTTTCCTGAGAGGGAGGGAGGTCTGGAGT-3'), having a sequence corresponding to the C-terminal of the mucin box portion and the N-terminal of SCDase. PCR was carried out by keeping the temperature at 96° C. for 2 minutes, and thereafter performing in 30 cycles, wherein one cycle of reaction comprises a process consisting of 98° C. for 10 seconds, 66° C. for 20 seconds, and 72° C. for 2 minutes. Thereafter, the product was kept at 72° C. for 7 minutes and cooled to 4° C.

Next, PCR was carried out using a sense primer U-kCDMbox-SCD (SEQ ID NO: 26, 5'-ACTCCAGACCTCCCTCCCTCTCAGGAAACGCAAACCACCCAGGCG-3'), having a sequence corresponding to the C-terminal of the mucin box portion and the N-terminal of SCDase, and an antisense primer L-SCD2145-XhoI (SEQ ID NO: 27, 5'-ACTCGAGTGGGCTTCTGCGCGCTCCCA-3'), having XhoI recognition site added to a sequence corresponding to the C-terminal of SCDase, with an EcoRV fragment containing the full length SCDase gene described in *Journal of Biological Chemistry,* 277, 17300-17307 (2002) (all teachings of which are incorporated herein by reference) as template DNA. The PCR conditions were the same as those mentioned above. After the purification of the amplified product by a conventional method, the product was used as the template for the subsequent PCR.

Each of the above amplified products was mixed, and PCR was carried out using the above primers RCS1 and L-SCD2145. PCR was carried out by keeping the temperature at 96° C. for 2 minutes, thereafter performing in 30 cycles, wherein one cycle of reaction comprises a process consisting of 98° C. for 10 seconds, 66° C. for 20 seconds, and 72° C. for 2.5 minutes. Thereafter, the amplified product was kept at 72° C. for 7 minutes and cooled to 4° C. The resulting amplified product was subjected to agarose gel electrophoresis, cut out from the gel and purified. The purified amplified product was then digested with the restriction endonucleases KpnI and XhoI (both manufactured by TAKARA BIO INC.) and ligated to pcDNA/Myc-His(+). *Escherichia coli* (DHα) was transformed with the above plasmid. Among the resulting transformants, 5 colonies were selected therefrom, an insert was confirmed. The sequence of the insert was determined by a conventional method. Subsequently, the transformants confirmed to contain the insert were cultured on a 100 ml scale.

The plasmid was purified from the culture using the CONCERT™ High Purity Plasmid Purification System (manufactured by Life Technology).

A plasmid for expressing a mucin box-fused type sphingolipid degrading enzyme was constructed on the basis of the nucleotide sequences of SMase (GenBank accession No. AB066097) and EGCase (GenBank accession No. U39554) in the same manner as described above.

The CHOP cells described in *Journal of Biological Chemistry,* 275, 11229-11234 (2000) (all teachings of which are incorporated herein by reference) ad COS1 cells (Health Science Research Resources Bank) were transfected with the above expression plasmid or an empty vector (mock) used as the control by using LipofectAMINE Plus (trade name, manufactured by Invitrogen). The resulting transfectant was cultured in Dulbecco's modified Eagle medium with 10% (v/v) fetal bovine serum and 60 μg/ml kanamycin on a 24-well plate at a concentration of $3\times10^4$ cells per well in an incubator in the presence of 5% $CO_2$ for 3 hours. Thereafter, the medium was exchanged, and the cells were cultured overnight. Cells for immunostaining were cultured so that the cells were adhered on the cover glass. Subsequently, the culture supernatant was collected and centrifuged at 15,000 rpm for 5 minutes.

(2) Immunofluorescent Staining

The recruitment of the mucin box-fused type sphingolipid degrading enzyme to the plasma membrane was confirmed by carrying out immunofluorescent staining of the above cells adherent to the cover glass. Concretely, the culture supernatant was aspirated, thereafter 500 μl of PBS containing 3% (v/v) para-formaldehyde was added, and this mixture was kept at room temperature for 15 minutes. Subsequently, the resulting product was washed thrice with PBS, and 500 μl of PBS containing 0.1 M glycine was added thereto, and the mixture was kept thereat for 3 minutes. After the resulting product was further washed with PBS, 500 μl of PBS containing 0.1% Triton™ X-100 was added thereto, and this mixture was kept thereat for 5 minutes. The resulting product was again washed thrice with PBS, and 500 μl of PBS containing 5% (v/v) BSA was added, thereto and the mixture was kept thereat for 15 minutes, and then washed thrice with PBS.

After the resulting product was washed, 250 μl of a 1st-Ab solution [PBS containing 1000× diluted anti-myc Ab (manufactured by Invitrogen)] was added thereto, and the mixture was kept at 4° C. overnight.

Figure 12:
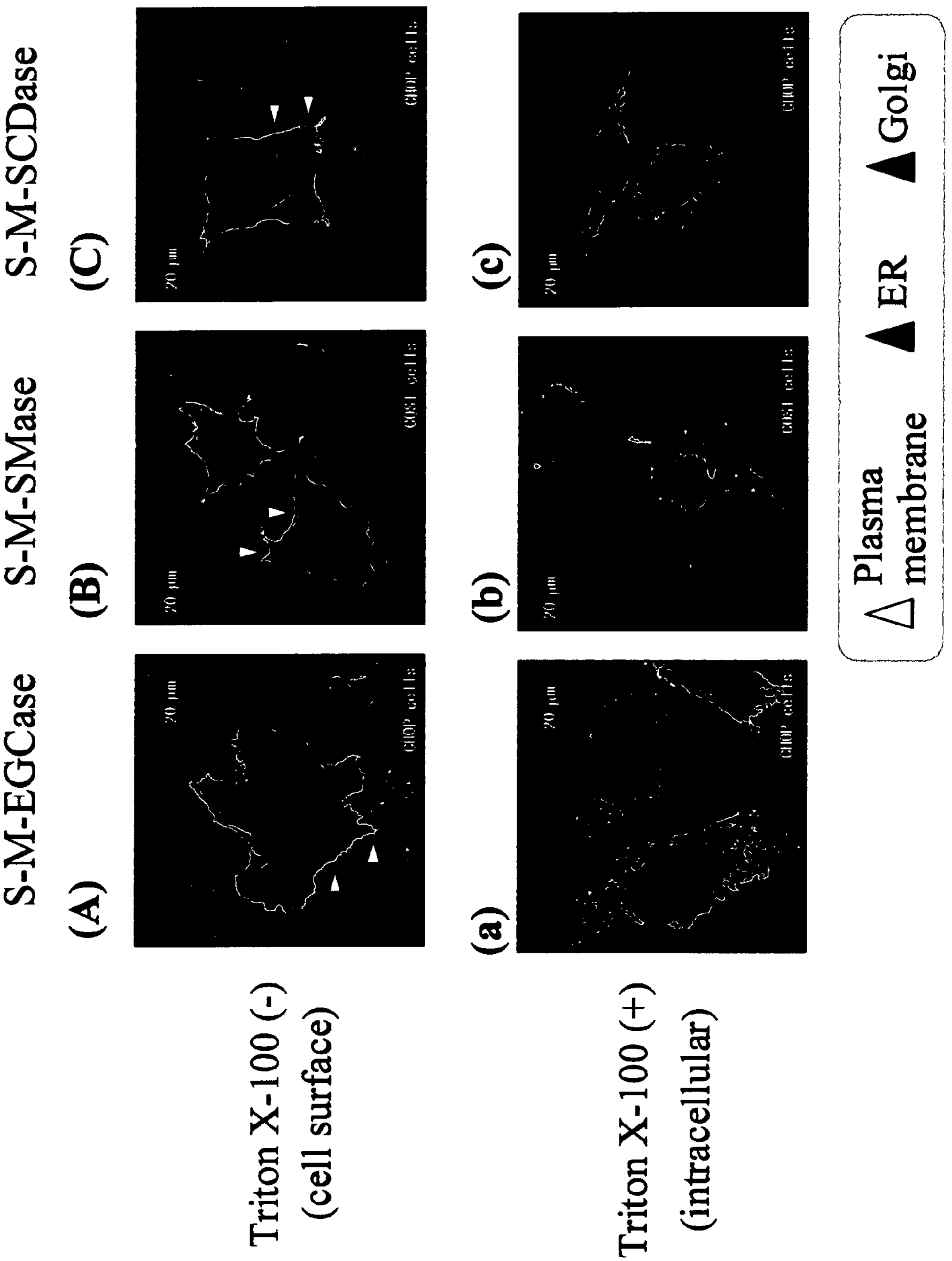
FIG. 12 shows the results of the immunofluorescent staining assay of the recruitment of sphingolipid degrading enzymes fused with mucin box to the cytoplasmic membrane. The column of "S-M-EGCase" [(A) and (a)] shows the results for EGCase fused with mucin box, the column of "S-M-SMase" [(B) and (b)] shows the results for SMase fused with mucin box, and the column of "S-M-SCDase" [(C) and (c)] shows the results for SCDase fused with mucin box. The upper rows [(A), (B), (C)] show the results for the cell surface, and the lower rows [(a), (b), (c)] show the results for inside the cells.

After the reaction with 1st-Ab, the resulting reaction product was washed thrice with PBS, and 250 μl of a 2nd-Ab solution [PBS containing 10000× diluted anti-mouse IgG HRP-labeled (manufactured by nacalai tesque)] was added thereto, and the mixture was kept at room temperature for 2 hours. Subsequently, the product was washed thrice with PBS and observed with a confocal laser microscope (manufactured by NIKON). The results are shown in FIG. 12. As shown in FIG. 12, it would be confirmed that all the mucin box-fused type sphingolipid degrading enzymes were localized on the cell surface.

(3) Confirmation of Activity of Enzymes Localized on Cell Surface

As to the mucin box-fused type sphingolipid degrading enzymes localized on the cell surface, prepared by the method of the present invention, whether or not their enzymatic activities were maintained was studied.

The activity of each enzyme was determined in the manner as described below.

(a) SCDase

The cultured cells prepared in the above (1) were suspended in 100 μl of 25 mM Tris-HCl (pH 7.5) containing 0.1% Triton™ X-100, to give a cell lysate. A 50 mM acetic acid-NaOH solution (pH 6.0) containing 5 nmol GM1a [prepared from the bovine brain by the method described in *Applied and Environmental Microbiology,* 63, 1861-1865 (1997) (all teachings of which are incorporated herein by reference)], 5 mM calcium chloride, and 0.1% Triton™ X-100 was added to 2.5 μl of the resulting cell lysate to make up a volume of 20 μl. After the resulting reaction mixture was kept at 37° C. for 30 minutes, the resulting reaction product was developed on TLC [developing solvent: chloroform: methanol: 10% acetic acid=5:4:1 (v/v/v)], and the activity was confirmed by the color development caused by an orcinol sulfate reagent as an index.

(b) SMase

The culture cells prepared in the above (1) were suspended in 100 μl of 25 mM Tris-HCl (pH 7.5) containing 0.1% (v/v) Triton™ X-100, to give a cell lysate. A 50 mM Tris-HCl solution (pH 7.5) containing 5 nmol C6-NBD-SM (manufactured by Sigma), 5 mM manganese chloride and 0.1% (v/v) Triton™ X-100 was added to 2.5 μl of the resulting lysate, to make up a volume of 20 μl. After the resulting reaction mixture was kept at 37° C. for 30 minutes, the reaction product obtained was developed on TLC [developing solvent: chloroform:methanol: 0.02% $CaCl_2$=5:4:1 (v/v/v)] and the activity was confirmed by the fluorescence derived from NBD (Ex: 475 nm, Em: 525 nm) as an index.

(c) EGCase

The culture cells prepared in the above (1) were suspended in 100 μl of 25 mM Tris-HCl (pH 7.5) containing 0.1% (v/v) Triton™ X-100, to give a cell lysate. A 50 mM acetic acid-NaOH solution (pH 5.0) containing 5 nmol GM1a and 0.2% (v/v) Triton™ X-100 was added to 2.5 μl of the resulting cell lysate, to make up a volume of 20 μl. After the resulting reaction mixture was kept at 37° C. for 30 minutes, the resulting reaction product was developed on TLC [developing solvent: chloroform:methanol: 10% acetic acid=5:4:1 (v/v/v)], and the activity was confirmed by the color development caused by using an orcinol sulfate reagent as an index.

Figure 13A:
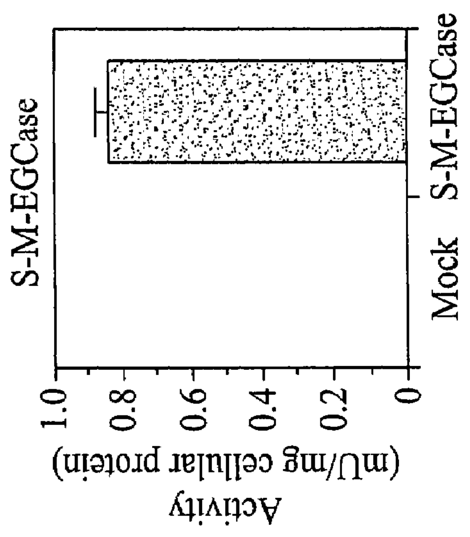
FIGS. 13A-13C show the results for the enzyme activity of the sphingolipid degrading enzymes fused with mucin box localized on the cell surface.
Figure 13B:
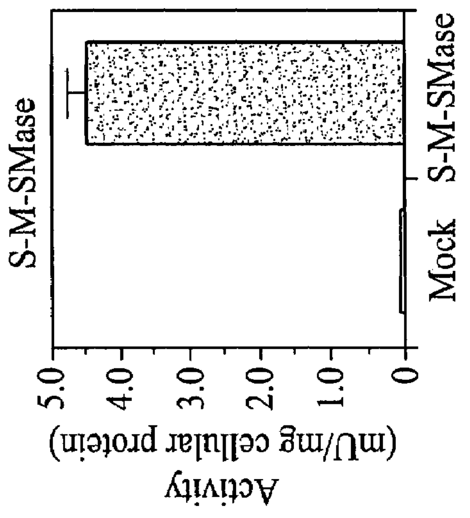
Figure 13C:
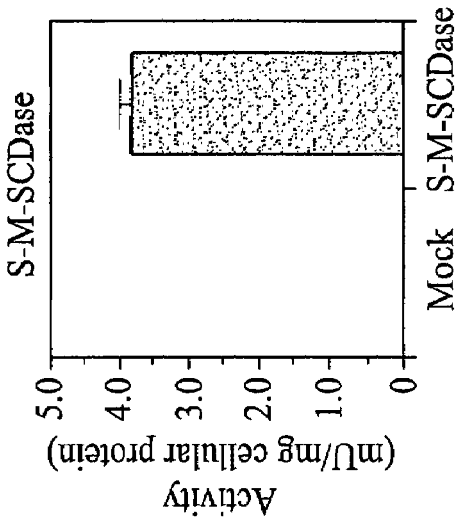

The above results are shown in FIG. 13. As shown in FIG. 13, all the enzymes could be confirmed to keep their enzymatic activities as compared to that of the control (empty vector: mock).

It could be confirmed from the above findings that the method of the present invention can be carried out irrespective of the kinds of proteins to be expressed.

Sequence Listing Free Text

SEQ ID NO: 13 is a sequence for primer.

SEQ ID NO: 14 is a sequence for primer.

SEQ ID NO: 15 is a sequence for primer.

SEQ ID NO: 16 is a sequence for primer.

SEQ ID NO: 18 is a sequence for primer.

SEQ ID NO: 19 is a sequence for primer.

SEQ ID NO: 20 is a sequence for primer.

SEQ ID NO: 24 is a sequence for primer.

SEQ ID NO: 25 is a sequence for primer.

SEQ ID NO: 26 is a sequence for primer.

SEQ ID NO: 27 is a sequence for primer.

Equivalent

The present invention may be embodied in other various forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

What is claimed is:

1. An isolated nucleic acid encoding a fusion protein formed between a heterogeneous polypeptide and a polypeptide having an activity for targeting a heterogeneous polypeptide to a surface of cytoplasmic membrane, wherein the nucleic acid encoding said polypeptide having an activity for targeting a heterogeneous polypeptide to a surface of cytoplasmic membrane has a nucleotide sequence selected from the group consisting of the following (A) to (B):

(A) a nucleotide sequence encoding an amino acid sequence selected from the group consisting of the following (a) to (b):

(a) the amino acid sequence shown in SEQ ID NO: 2; and (b) an amino acid sequence with a mutation in SEQ ID NO: 2 selected from the group consisting of the following (1) to (34);

(1) substitution of an amino acid residue at position 1 to T, (2) substitution of an amino acid residue at position 2 to T, (3) substitution of an amino acid residue at position 3 to P or T, (4) substitution of an amino acid residue at position 4 to T, (5) substitution of an amino acid residue at position 5 to Q, (6) substitution of an amino acid residue at position 6 to A, (7) substitution of an amino acid residue at position 7 to F or P, (8) substitution of an amino acid residue at position 8 to T, (9) substitution of an amino acid residue at position 9 to P,

(10) substitution of an ammo acid residue at position 11 to L, S or P,

(11) substitution of an ammo acid residue at position 12 to N, S or A,

(12) substitution of an amino acid residue at position 13 to S,

(13) substitution of an amino acid residue at position 15 to P,

(14) substitution of an amino acid residue at position 17 to S or P,

(15) substitution of an amino acid residue at position 18 to P, T or A,

(16) substitution of an amino acid residue at position 19 to P,

(17) substitution of an amino acid residue at position 20 to t,

(18) substitution of an amino acid residue at position 21 to S or I,

(19) substitution of an amino acid residue at position 23 to S or T,

(20) substitution of an amino acid residue at position 24 to P or A,

(21) substitution of an amino acid residue at position 25 to T,

(22) substitution of an amino acid residue at position 26 to I,

(23) substitution of an amino acid residue at position 27 to S,

(24) substitution of an amino acid residue at position 28 to S,

(25) substitution of an amino acid residue at position 30 to T or Q,

(26) substitution of an amino acid residue at position 31 to N, S, T, or A,

(27) substitution of an amino acid residue at position 32 to F or C,

(28) substitution of an amino acid residue at position 33 to R,

(29) substitution of an amino acid residue at position 34 to T,

(30) substitution of an amino acid residue at position 35 to E or T,

(31) substitution of an amino acid residue at position 36 to T,

(32) deletion of a sequence consisting of amino acids at positions 1 to 8,

(33) deletion of a sequence consisting of amino acids at positions 1 to 7, and

(34) deletion of a sequence consisting of amino acids at positions 32 to 36; and (B) a nucleotide sequence of a nucleic acid that hybridizes to an antisense sequence of the nucleic acid consisting of the nucleotide sequence shown in SEQ ID NO: 1 under conditions of carrying out incubation at 65° C., overnight in a solution containing 6×SSC, 0.5% SDS, 5×Denhardt's, and 100 μg/ml herring sperm DNA, and carrying out washing using a buffer with 2×SSC at a temperature of 25° C. below a $T_m$ value of the nucleic acid used, wherein a polypeptide encoded by the nucleotide sequence has an activity for targeting a heterogeneous polypeptide to a surface of cytoplasmic membrane, and wherein the nucleic acid encoding said heterogeneous polypeptide is operably linked downstream to a nucleotide sequence selected from the group consisting of said (A) to (B) via a nucleotide sequence for operably linking the nucleotide encoding a heterogeneous polypeptide.

2. A construct for introducing into a host cell for localizing a heterogeneous polypeptide on a cell surface, comprising one nucleotide sequence selected from the group consisting of the following (A) to (B):

(A) a nucleotide sequence encoding an amino acid sequence selected from the group consisting of the following (a) to (b):

(a) the amino acid sequence shown in SEQ ID NO: 2; and (b) an amino acid sequence with a mutation in SEQ ID NO: 2 selected from the group consisting of the following (1) to (34):

(1) substitution of an amino acid residue at position 1 to T, (2) substitution of an amino acid residue at position 2 to t, (3) substitution of an amino acid residue at position 3 to P or T, (4) substitution of an amino acid residue at position 4 to T, (5) substitution of an amino acid residue at position 5 to Q, (6) substitution of an amino acid residue at position 6 to A, (7) substitution of an amino acid residue at position 7 to F or P, (8) substitution of an amino acid residue at position 8 to T, (9) substitution of an amino acid residue at position 9 to P,

(10) substitution of an ammo acid residue at position 11 to L, S or P,

(11) substitution of an ammo acid residue at position 12 to N, S or A,

(12) substitution of an amino acid residue at position 13 to S,

(13) substitution of an amino acid residue at position 15 to P,

(14) substitution of an amino acid residue at position 17 to S or P,

(15) substitution of an amino acid residue at position 18 to P, T or A,

(16) substitution of an amino acid residue at position 19 to P,

(17) substitution of an amino acid residue at position 20 to T,

(18) substitution of an amino acid residue at position 21 to S or I,

(19) substitution of an amino acid residue at position 23 to S or T,

(20) substitution of an amino acid residue at position 24 to P or A,

(21) substitution of an amino acid residue at position 25 to T,

(22) substitution of an amino acid residue at position 26 to I,

(23) substitution of an amino acid residue at position 27 to S,

(24) substitution of an amino acid residue at position 28 to S,

(25) substitution of an amino acid residue at position 30 to T or Q,

(26) substitution of an amino acid residue at position 31 to N, S, T or A,

(27) substitution of an amino acid residue at position 32 to F or C,

(28) substitution of an amino acid residue at position 33 to R,

(29) substitution of an amino acid residue at position 34 to T,

(30) substitution of an amino acid residue at position 35 to E or T,

(31) substitution of an amino acid residue at position 36 to T,

(32) deletion of a sequence consisting of amino acids at positions 1 to 8,

(33) deletion of a sequence consisting of amino acids at positions 1 to 7, and

(34) deletion of a sequence consisting of amino acids at positions 32 to 36; and (B) a nucleotide sequence of a nucleic acid that hybridizes to an antisense sequence of the nucleic acid consisting of the nucleotide sequence shown in SEQ ID NO: 1 under conditions of carrying out incubation at 65° C., overnight in a solution containing 6×SSC, 0.5% SDS, 5×Denhardt's, and 100 μg/ml herring sperm DNA, and carrying out washing using a buffer with 2×SSC at a temperature of 25° C. below a $T_m$ value of the nucleic acid used, wherein a polypeptide encoded by the nucleotide sequence has an activity for targeting a heterogeneous polypeptide to a surface of cytoplasmic membrane, and wherein a nucleic acid encoding a heterogeneous polypeptide to be expressed is operably linked downstream to a .nucleotide sequence selected from the group consisting of said (A) to (B) via a nucleotide sequence for operably linking the nucleotide encoding a heterogeneous polypeptide.

3. The construct according to claim 2, wherein the heterogeneous protein is one member selected from the group consisting of enzymes, peptide hormones, growth factors, cytokines, chemokines, antibody molecules, complement molecules, serum proteins, cell adhesion factors, nucleic acid-binding proteins, neurotrophic factors, receptors and ligands.

4. A transformant harboring the construct for introducing a cell as defined in claim 3.

5. A kit for expressing a heterogeneous polypeptide to be expressed on cytoplasmic membrane, comprising the construct as defined in claim 2.

6. The kit according to claim 5, further comprising a host cell capable of carrying out an O-glycan addition as a post-translational modification.

7. A kit for detecting a ligand or receptor for a polypeptide comprising the construct according to claim 2, wherein a nucleic acid encoding a heterogeneous polypeptide to be expressed is operably linked downstream to a nucleotide sequence selected from the group consisting of said (A) to (B) via a nucleotide sequence for operably linking the nucleotide encoding a heterogeneous polypeptide.

8. A kit for detecting a ligand or receptor for a polypeptide comprising the construct according to claim 2, wherein a nucleic acid encoding a heterogeneous polypeptide to be expressed is operably linked downstream to a nucleotide sequence selected from the group consisting of said (A) to (B) via a nucleotide sequence for operably linking the nucleotide encoding a heterogeneous polypeptide, wherein the heterogeneous polypeptide is one member selected from the group consisting of enzymes, peptide hormones, growth factors, cytokines, chemokines, antibody molecules, complement molecules, serum proteins, cell adhesion factors, nucleic acid-binding proteins, neurotrophic factors, receptors and ligands.

9. An oligonucleotide probe that hybridizes to a nucleic acid consisting of the nucleotide sequence shown in SEQ ID NO: 1 under conditions of carrying out incubation at 65° C., overnight in a solution containing 6×SSC, 0.5% SDS, 5×Denhardt's, and 100 μg /ml herring sperm DNA, and carrying out washing using a buffer with 2×SSC at a temperature of 25° C. below a $T_m$ value of the nucleic acid used, wherein the oligonucleotide probe consists of 18 to 150 nucleotides in length.

10. A pair of primers consisting of an oligonulceotide that hybridizes to a nucleic acid consisting of the nucleotide sequence shown in SEQ ID NO: 1 under stringent conditions, wherein the oligonucleotide consists of 17 to 50 nucleotides in length; and an oligonucleotide that hybridizes to an antisense nucleic acid consisting of the nucleotide sequence shown in SEQ ID NO:1 under stringent conditions, wherein the oligonucleotide consists of 17 to 50 nucleotides in length; and wherein said stringent conditions are the conditions for carrying out incubation at a temperature of 25° C. below a $T_m$ value of said pair of primers overnight in a solution containing 6×SSC, 0.5% SDS, 5×Denhardt's, and 100 μg/ml herring sperm DNA, and carrying out washing using a buffer with 2×SSC at a temperature of 25° C. below a $T_m$ value of said pair of primers.

11. A kit used for detecting a nucleic acid encoding a polypeptide having an activity for targeting a heterogeneous polypeptide to a surface of cytoplasmic membrane, comprising an oligonucleotide probe that hybridizes to a nucleic acid consisting of the nucleotide sequence shown in SEQ ID NO: 1 under stringent conditions, wherein the oligonucleotide probe consists of 18 to 150 nucleotides in length and/or a pair of primers consisting of an oligonucleotide that hybridizes to a nucleic acid consisting of the nucleotide sequence shown in SEQ ID NO:1 under stringent conditions, wherein the oligonucleotide consists of 17 to 50 nucleotides in length; and an oligonucleotide that hybridizes to an antisense nucleic acid consisting of the nucleotide sequence shown in SEQ ID NO: 1 under stringent conditions, wherein the oligonucleotide consists of 17 to 50 nucleotides in length; and wherein said stringent conditions are the conditions for carrying out incubation at a temperature of 25° C. below a $T_m$ value of said oligonucleotide probe or said pair of primers overnight in a solution containing 6×SSC, 0.5% SDS, 5×Denhardt's, and 100 μg/ml herring sperm DNA, and carrying out washing using a buffer with 2×SSC at a temperature of 25° C. below a $T_m$ value of said oligonucleotide probe or said pair of primers.

* * * * *